(12) United States Patent
Yamamoto et al.

(10) Patent No.: US 7,880,006 B2
(45) Date of Patent: Feb. 1, 2011

(54) QUINOLINE DERIVATIVES AND INSECTICIDE COMPRISING THEREOF AS ACTIVE INGREDIENT

(75) Inventors: Kazumi Yamamoto, Kamakura (JP); Ryo Horikoshi, Yokohama (JP); Kazuhiko Oyama, Higashi-Murayama (JP); Hiroshi Kurihara, Ageo (JP); Shizuo Shimano, Ageo (JP); Takaaki Miyake, Saitama (JP); Hiroki Hotta, Saitama (JP); Jun Iwabuchi, Saitama (JP)

(73) Assignees: Meiji Seika Kaisha, Ltd., Tokyo-To (JP); Nippon Kayaku Co., Ltd., Tokyo-To (JP)

( * ) Notice: Subject to any disclaimer, the term of this patent is extended or adjusted under 35 U.S.C. 154(b) by 968 days.

(21) Appl. No.: 11/632,420

(22) PCT Filed: Aug. 3, 2005

(86) PCT No.: PCT/JP2005/014217
§ 371 (c)(1),
(2), (4) Date: Jan. 12, 2007

(87) PCT Pub. No.: WO2006/013896
PCT Pub. Date: Feb. 9, 2006

(65) Prior Publication Data
US 2007/0203181 A1   Aug. 30, 2007

(30) Foreign Application Priority Data
Aug. 4, 2004 (JP) .............................. 2004-228337

(51) Int. Cl.
*A61K 31/04* (2006.01)
*C07D 215/38* (2006.01)
(52) U.S. Cl. .................. 546/159; 546/162; 514/312
(58) Field of Classification Search ............... 546/153, 546/162, 159; 514/312
See application file for complete search history.

(56) References Cited

U.S. PATENT DOCUMENTS

| | | | |
|---|---|---|---|
| 4,168,311 A | 9/1979 | Studeneer et al. | |
| 5,190,952 A | 3/1993 | Minowa et al. | |
| 5,990,116 A | 11/1999 | Nussbaumer | |
| 7,067,668 B2 * | 6/2006 | Yamamoto et al. | 546/153 |
| 7,129,356 B2 * | 10/2006 | Angibaud et al. | 546/157 |
| 2003/0119863 A1 | 6/2003 | Yamamoto et al. | |
| 2004/0063944 A1 | 4/2004 | Angibaud et al. | |
| 2004/0152728 A1 | 8/2004 | Yamamoto et al. | |
| 2006/0111375 A1 | 5/2006 | Shimizu et al. | |
| 2008/0207617 A1 | 8/2008 | Miwa et al. | |

FOREIGN PATENT DOCUMENTS

| | | |
|---|---|---|
| DE | 831100 | 7/1949 |
| DE | 23 61 438 | 6/1975 |
| EP | 0 987 251 | 3/2000 |
| EP | 1 548 008 | 6/2005 |
| EP | 1 566 379 | 8/2005 |
| EP | 1 724 268 | 11/2006 |
| WO | 96/28430 | 9/1996 |
| WO | 98/55460 | 12/1998 |
| WO | 02/26713 | 4/2002 |
| WO | 02/051835 | 7/2002 |
| WO | 2004/058759 | 7/2004 |

OTHER PUBLICATIONS

Bryon Riegel et al., "The synthesis of some 4-quinolinols and 4-chloroquinolines by the ethoxymethylenemalonic ester method", J. Am. Chem. Soc., vol. 68, No. 7, 1946, pp. 1264-1266, XP002527058.
C.E. Kaslow et al., "Substituted quinolines", J. Am. Chem. Soc., vol. 70, No. 10, 1948, pp. 3350-3351, XP002527059.
C.E. Kaslow et al., "Substituted quinolineacetic acids", J. Org. Chem., vol. 16, No. 6, 1951, pp. 895-898, XP002527060.
C.E. Kaslow et al., "Phenylquinolines", J. Am. Chem, Soc., vol. 73, No. 10, 1951, pp. 4986-4987, XP002527061.
James W. Wilson et al., "Unsymmetrical p,p'-disubstituted diphenylhexanes related to hexestrol", J. Org. Chem., vol. 18, No. 1, 1953, pp. 96-105, XP002527062.
Hauser et al., "Reactions of β-keto esters with aromatic amines. Syntheses of 2- and 4-hydroxyquinoline derivatives." J. Am. Chem. Soc. vol. 70, pp. 2402-2404 (1948).
Chong et al., "Synthetic connections to the aromatic directed metalation reaction. A modified von Niementowski quinoline synthesis from anthranilamides." Tetrahedron Letters. vol. 27, No. 44, pp. 5323-5326 (1986).
Database CAPLUS on STN CAS Abstract No. 1980-146616, (Abstract of IL1975-47609)., 1980.

* cited by examiner

*Primary Examiner*—D. Margaret Seaman
(74) *Attorney, Agent, or Firm*—Wenderoth, Lind & Ponack, L.L.P.

(57) ABSTRACT

Disclosed are compounds that have excellent insecticidal activity and are usable as agricultural and horticultural insecticides. Compounds represented by formula (I) or agriculturally and horticulturally acceptable acid addition salts thereof have excellent insecticidal activity and are usable as agricultural and horticultural insecticides.

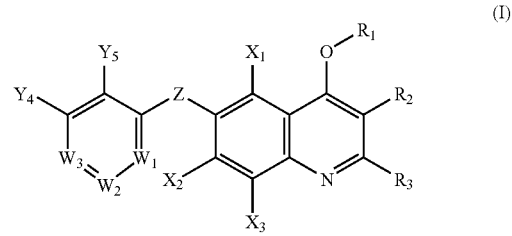

9 Claims, No Drawings

QUINOLINE DERIVATIVES AND INSECTICIDE COMPRISING THEREOF AS ACTIVE INGREDIENT

CROSS-REFERENCE OF RELATED APPLICATION

This patent application is an application claiming priority based on an early filed Japanese patent application, Japanese Patent Application No. 228337/2004 (filing date: Aug. 4, 2004). The whole disclosure of Japanese Patent Application No. 228337/2004 is incorporated herein by reference.

BACKGROUND OF THE INVENTION

1. Field of the Invention

The present invention relates to quinoline derivatives and agricultural and horticultural insecticides comprising the same as an active ingredient.

2. Background Art

Various compounds having control effect have hitherto been developed. For example, WO 98/055460 discloses quinoline derivatives having fungicidal activity, but on the other hand, it does not disclose the insecticidal activity of these derivatives. Japanese Patent No. 2633377 and U.S. Pat. No. 4,168,311 disclose quinoline derivatives having insecticidal activity. The compounds described in these publications are different from quinoline derivatives represented by formula (I) which will be described below in the structure of the substituent at the 6-position of quinoline. Regarding agricultural and horticultural insecticides, it can be said that, due to problems associated with, for example, the presence of insect species which have low sensitivity to these compounds or are difficult to be controlled, the development of novel agricultural and horticultural insecticides having excellent insecticidal activity are still desired.

SUMMARY OF THE INVENTION

The present inventors have now found that novel quinoline derivatives represented by formula (I) have significant insecticidal activity. The present invention has been made based on such finding.

Accordingly, an object of the present invention is to provide novel quinoline derivatives having significant insecticidal activity and to provide agricultural and horticultural insecticides comprising the same as an active ingredient which have reliable effect and can be safely used.

According to the first aspect of the present invention, there is provided a quinoline derivative. This derivative is a compound represented by formula (I) or an agriculturally and horticulturally acceptable acid addition salt thereof:

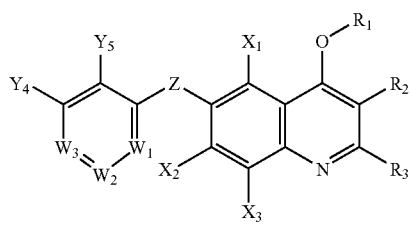

(I)

wherein
$R_1$ represents
  a hydrogen atom,
  an alkali metal,
  an alkaline earth metal,
  optionally substituted $C_{1-18}$ alkyl,
  optionally substituted $C_{2-18}$ alkenyl,
  optionally substituted $C_{2-18}$ alkynyl,
  optionally substituted $C_{3-10}$ cycloalkyl,
  optionally substituted phenyl lower alkyl,
  optionally substituted phenoxy lower alkyl,
  optionally substituted phenyl,
  optionally substituted heterocyclic group,
  $COR_4$ wherein $R_4$ represents
    optionally substituted $C_{1-18}$ alkyl,
    optionally substituted $C_{2-18}$ alkenyl,
    optionally substituted $C_{2-18}$ alkynyl,
    optionally substituted $C_{3-10}$ cycloalkyl,
    optionally substituted phenyl lower alkyl,
    optionally substituted phenoxy lower alkyl,
    optionally substituted phenyl,
    optionally substituted heterocyclic group,
  optionally substituted $C_{1-4}$ alkylthio,
  $OR_5$ wherein $R_5$ represents
    optionally substituted $C_{1-18}$ alkyl,
    optionally substituted $C_{2-18}$ alkenyl,
    optionally substituted $C_{2-18}$ alkynyl,
    optionally substituted $C_{3-10}$ cycloalkyl,
    optionally substituted phenyl lower alkyl,
    optionally substituted phenoxy lower alkyl,
    optionally substituted phenyl, or
    optionally substituted heterocyclic group, or
  $NR_6R_7$ wherein $R_6$ and $R_7$ each independently represents
    a hydrogen atom,
    optionally substituted $C_{1-18}$ alkyl, or
    optionally substituted phenyl, or
  $SO_2R_8$ wherein $R_8$ represents
    optionally substituted $C_{1-18}$ alkyl,
    optionally substituted $C_{2-18}$ alkenyl,
    optionally substituted $C_{2-18}$ alkynyl,
    optionally substituted $C_{3-10}$ cycloalkyl,
    optionally substituted phenyl lower alkyl,
    optionally substituted phenoxy lower alkyl,
    optionally substituted phenyl, or
    optionally substituted heterocyclic group,
$R_2$ represents a hydrogen atom or optionally substituted $C_{1-4}$ alkyl,
$R_3$ represents
  a hydrogen atom,
  optionally substituted $C_{1-18}$ alkyl,
  optionally substituted $C_{2-4}$ alkenyl, or
  optionally substituted $C_{1-4}$ alkoxy,
  wherein, in $R_1$, $R_2$, and $R_3$, the substituent in each of the optionally substituted groups is selected from the group consisting of halogen atom; $C_{1-4}$ alkyloxy; $C_{1-4}$ alkyloxy-$C_{1-4}$ alkyloxy; $C_{1-4}$ alkyloxycarbonyl; nitro; cyano; formyl; trifluoromethyl; trifluoromethoxy; acetyl; acetyloxy; $C_{1-4}$ alkyl, provided that this $C_{1-4}$ alkyl is not a substituent for the alkyl group; and $C_{3-6}$ cycloalkyl optionally substituted by halogen atom,
alternatively $R_2$ and $R_3$ together represent —$(CH_2)_m$— wherein m is 3 or 4,
$X_1$, $X_2$, and $X_3$ each independently represent
  a hydrogen atom,
  a halogen atom,
  $C_{1-4}$ alkyl optionally substituted by halogen atom,
  $C_{1-4}$ alkyloxy optionally substituted by halogen atom,
  $C_{1-4}$ alkylthio optionally substituted by halogen atom,
  $C_{1-4}$ alkyloxycarbonyl optionally substituted by halogen atom, nitro, or cyano, provided that $X_1$, $X_2$, and $X_3$ do not simultaneously represent a hydrogen atom, $W_1$ represents a nitrogen atom or C—$Y_1$, $W_2$ represents a nitrogen atom or C—$Y_2$, $W_3$ represents a nitrogen atom or C—$Y_3$, provided that, when $W_1$ represents a nitrogen atom, $W_2$ and $W_3$ represent C—$Y_2$ and C—$Y_3$, respectively; when $W_2$ represents a nitrogen atom, $W_1$ and $W_3$ represent C—$Y_1$ and C—$Y_3$, respectively; and when $W_3$ represents a nitrogen atom, $W_1$ and $W_2$ represent C—$Y_1$ and C—$Y_2$, respectively, $Y_1$, $Y_2$, $Y_3$, $Y_4$, and $Y_5$ each independently represent a hydrogen atom, A, or B, provided that $W_1$, $W_2$, and $W_3$ respectively represent C—$Y_1$, C—$Y_2$, and C—$Y_3$, and, when Z represents a bond, methylene optionally substituted by one or two methyl groups, or an oxygen atom, at least one of $Y_1$, $Y_2$, $Y_3$, $Y_4$, and $Y_5$ represents A, wherein A represents a group selected from the group consisting of:

$C_{1-8}$ alkyl which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{2-8}$ alkenyl which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{1-8}$ alkyloxy which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{2-8}$ alkenyloxy which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{1-8}$ alkyloxycarbonyl which is optionally substituted by one or more halogen atoms which may be the same or different, and/or $C_{1-4}$ alkyloxy substituted by one or more halogen atoms which may be the same or different;

$C_{1-8}$ alkylthio which is optionally substituted by one or more halogen atoms which may be the same or different, and/or $C_{1-4}$ alkyloxy substituted by one or more halogen atoms which may be the same or different;

$C_{2-8}$ alkenylthio which is optionally substituted by one or more halogen atoms which may be the same or different, and/or $C_{1-4}$ alkyloxy substituted by one or more halogen atoms which may be the same or different;

$C_{1-8}$ alkylsulfinyl which is optionally substituted by one or more halogen atoms which may be the same or different, and/or $C_{1-4}$ alkyloxy substituted by one or more halogen atoms which may be the same or different;

$C_{2-8}$ alkenylsulfinyl which is optionally substituted by one or more halogen atoms which may be the same or different, and/or $C_{1-4}$ alkyloxy substituted by one or more halogen atoms which may be the same or different;

$C_{1-8}$ alkylsulfonyl which is optionally substituted by one or more halogen atoms which may be the same or different, and/or $C_{1-4}$ alkyloxy substituted by one or more halogen atoms which may be the same or different;

$C_{2-8}$ alkenylsulfonyl which is optionally substituted by one or more halogen atoms which may be the same or different, and/or $C_{1-4}$ alkyloxy substituted by one or more halogen atoms which may be the same or different;

phenyl which is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different; and phenoxy which is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different, B represents a group selected from the group consisting of a halogen atom, $C_{1-4}$ alkyl, $C_{1-4}$ alkyloxy, nitro, and cyano, alternatively adjacent two of $Y_1$, $Y_2$, $Y_3$, $Y_4$, and $Y_5$ may together represent —O—$(CH_2)_n$—O— optionally substituted by halogen atom, —$(CH_2)_n$—O— optionally substituted by halogen atom, —S—$(CH_2)_n$—S— optionally substituted by halogen atom, —$(CH_2)_n$—S— optionally substituted by halogen atom, or —$(CH_2)_n$— optionally substituted by halogen atom, wherein n is 1, 2, or 3, Z represents a bond, an oxygen atom, a sulfur atom, SO, $SO_2$, -Q-, —O-Q-, —O-Q-O—, or CO, and Q represents $C_{1-4}$ alkylene which is optionally substituted by halogen atom, cyano, or $C_{1-4}$ alkyl optionally substituted by halogen atom; —$(CH_2)_p$—$CR_{10}R_{11}$—$(CH_2)_q$— wherein $R_{10}$, $R_{11}$ and the carbon atom to which they are attached to together represent $C_{3-6}$ cycloalkyl which is optionally substituted by halogen atom or $C_{1-4}$ alkyl optionally substituted by halogen atom, and p and q each independently are an integer of 0 to 3; or $C_{2-4}$ alkenylene which is optionally substituted by halogen atom, cyano, or $C_{1-4}$ alkyl optionally substituted by halogen atom.

According to the second aspect of the present invention, there is provided an agricultural and horticultural insecticide. This insecticide comprises as an active ingredient a quinoline derivative represented by formula (I) or an agriculturally and horticulturally acceptable acid addition salt thereof.

According to the third aspect of the present invention, there is provided an agricultural and horticultural insecticide. This insecticide comprises as an active ingredient a compound represented by formula (Ia) or an agriculturally and horticulturally acceptable acid addition salt thereof:

(Ia)

wherein $R_1$ represents
- a hydrogen atom,
- an alkali metal,
- an alkaline earth metal,
- optionally substituted $C_{1-18}$ alkyl,
- optionally substituted $C_{2-18}$ alkenyl,
- optionally substituted $C_{2-18}$ alkynyl,
- optionally substituted $C_{3-10}$ cycloalkyl,
- optionally substituted phenyl lower alkyl,
- optionally substituted phenoxy lower alkyl,
- optionally substituted phenyl,
- optionally substituted heterocyclic group,
- $COR_4$ wherein $R_4$ represents
  - optionally substituted $C_{1-18}$ alkyl,
  - optionally substituted $C_{2-18}$ alkenyl,
  - optionally substituted $C_{2-18}$ alkynyl,
  - optionally substituted $C_{3-10}$ cycloalkyl,
  - optionally substituted phenyl lower alkyl,
  - optionally substituted phenoxy lower alkyl,
  - optionally substituted phenyl,
  - optionally substituted heterocyclic group,
  - optionally substituted $C_{1-4}$ alkylthio,
- $OR_5$ wherein $R_5$ represents
  - optionally substituted $C_{1-18}$ alkyl,
  - optionally substituted $C_{2-18}$ alkenyl,
  - optionally substituted $C_{2-18}$ alkynyl,
  - optionally substituted $C_{3-10}$ cycloalkyl,
  - optionally substituted phenyl lower alkyl,
  - optionally substituted phenoxy lower alkyl,
  - optionally substituted phenyl, or
  - optionally substituted heterocyclic group, or
- $NR_6R_7$ wherein $R_6$ and $R_7$ each independently represents
  - a hydrogen atom,
  - optionally substituted $C_{1-18}$ alkyl, or
  - optionally substituted phenyl, or
- $SO_2R_8$ wherein $R_8$ represents
  - optionally substituted $C_{1-18}$ alkyl,
  - optionally substituted $C_{2-18}$ alkenyl,
  - optionally substituted $C_{2-18}$ alkynyl,
  - optionally substituted $C_{3-10}$ cycloalkyl,
  - optionally substituted phenyl lower alkyl,
  - optionally substituted phenoxy lower alkyl,
  - optionally substituted phenyl, or
  - optionally substituted heterocyclic group, $R_2$ represents a hydrogen atom or optionally substituted $C_{1-4}$ alkyl, $R_3$ represents
- a hydrogen atom,
- optionally substituted $C_{1-18}$ alkyl,
- optionally substituted $C_{2-4}$ alkenyl, or
- optionally substituted $C_{1-4}$ alkoxy, wherein, in $R_1$, $R_2$, and $R_3$, the substituent in each of the optionally substituted groups is selected from the group consisting of halogen atom; $C_{1-4}$ alkyloxy; $C_{1-4}$ alkyloxy-$C_{1-4}$ alkyloxy; $C_{1-4}$ alkyloxycarbonyl; nitro; cyano; formyl; trifluoromethyl; trifluoromethoxy; acetyl; acetyloxy; $C_{1-4}$ alkyl, provided that this $C_{1-4}$ alkyl is not a substituent for the alkyl group; and $C_{3-6}$ cycloalkyl optionally substituted by halogen atom, alternatively $R_2$ and $R_3$ together represent —$(CH_2)_m$— wherein m is 3 or 4, $X_1$, $X_2$, and $X_3$ each independently represent
- a hydrogen atom,
- a halogen atom,
- $C_{1-4}$ alkyl optionally substituted by halogen atom,
- $C_{1-4}$ alkyloxy optionally substituted by halogen atom,
- $C_{1-4}$ alkylthio optionally substituted by halogen atom,
- $C_{1-4}$ alkyloxycarbonyl optionally substituted by halogen atom,
- nitro, or
- cyano, provided that $X_1$, $X_2$, and $X_3$ do not simultaneously represent a hydrogen atom, $W_{11}$ represents a nitrogen atom or C—$Y_{11}$,
$W_{12}$ represents a nitrogen atom or C—$Y_{12}$,
$W_{13}$ represents a nitrogen atom or C—$Y_{13}$, provided that, when $W_{11}$ represents a nitrogen atom, $W_{12}$ and $W_{13}$ represent C—$Y_{12}$ and C—$Y_{13}$, respectively; when $W_2$ represents a nitrogen atom, $W_{11}$ and $W_{13}$ represent C—$Y_{11}$ and C—$Y_{13}$, respectively; and when $W_{13}$ represents a nitrogen atom, $W_{11}$ and $W_{12}$ represent C—$Y_{11}$ and C—$Y_{12}$, respectively, $Y_{11}$, $Y_{12}$, $Y_{13}$, $Y_{14}$, and $Y_{15}$ each independently represent a hydrogen atom, A, or B, wherein A represents a group selected from the group consisting of:

$C_{1-8}$ alkyl which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{2-8}$ alkenyl which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{1-8}$ alkyloxy which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{2-8}$ alkenyloxy which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{1-8}$ alkyloxycarbonyl which is optionally substituted by one or more halogen atoms which may be the same or different, and/or $C_{1-4}$ alkyloxy substituted by one or more halogen atoms which may be the same or different;

$C_{1-8}$ alkylthio which is optionally substituted by one or more halogen atoms which may be the same or different, and/or $C_{1-4}$ alkyloxy substituted by one or more halogen atoms which may be the same or different;

$C_{2-8}$ alkenylthio which is optionally substituted by one or more halogen atoms which may be the same or different, and/or $C_{1-4}$ alkyloxy substituted by one or more halogen atoms which may be the same or different;

$C_{1-8}$ alkylsulfinyl which is optionally substituted by one or more halogen atoms which may be the same or different, and/or $C_{1-4}$ alkyloxy substituted by one or more halogen atoms which may be the same or different;

$C_{2-8}$ alkenylsulfinyl which is optionally substituted by one or more halogen atoms which may be the same or different, and/or $C_{1-4}$ alkyloxy substituted by one or more halogen atoms which may be the same or different;

$C_{1-8}$ alkylsulfonyl which is optionally substituted by one or more halogen atoms which may be the same or different, and/or $C_{1-4}$ alkyloxy substituted by one or more halogen atoms which may be the same or different;

$C_{2-8}$ alkenylsulfonyl which is optionally substituted by one or more halogen atoms which may be the same or different, and/or $C_{1-4}$ alkyloxy substituted by one or more halogen atoms which may be the same or different;

phenyl which is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different; and phenoxy which is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different, B represents a group selected from the group consisting of a halogen atom, $C_{1-4}$ alkyl, $C_{1-4}$ alkyloxy, nitro, and cyano, alternatively adjacent two of $Y_{11}$, $Y_{12}$, $Y_{13}$, $Y_{14}$, and $Y_{15}$ may together represent —O—$(CH_2)_n$—O— optionally substituted by halogen atom, —$(CH_2)_n$—O— optionally substituted by halogen atom, —S—$(CH_2)_n$—S— optionally substituted by halogen atom, —$(CH_2)_n$—S— optionally substituted by halogen atom, or —$(CH_2)_n$— optionally substituted by halogen atom, wherein n is 1, 2, or 3, Z represents a bond, an oxygen atom, a sulfur atom, SO, $SO_2$, -Q-, —O-Q-, —O-Q-O—, or CO, and Q represents $C_{1-4}$ alkylene which is optionally substituted by halogen atom, cyano, or $C_{1-4}$ alkyl optionally substituted by halogen atom; —$(CH_2)_p$—$CR_{10}R_{11}$—$(CH_2)_q$— wherein $R_{10}$, $R_{11}$ and the carbon atom to which they are attached together represent $C_{3-6}$ cycloalkyl which is optionally substituted by halogen atom or $C_{1-4}$ alkyl optionally substituted by halogen atom, and p and q each independently are an integer of 0 to 3; or $C_{2-4}$ alkenylene which is optionally substituted by halogen atom, cyano, or $C_{1-4}$ alkyl optionally substituted by halogen atom.

The quinoline derivative according to the present invention has exellent control effect against agricultural and horticultural insect pests and thus are useful as agricultural and horticultural insecticides.

DETAILED DESCRIPTION OF THE INVENTION

Compounds Represented by Formula (I) and Formula (Ia)

The term "halogen" as used herein means a fluorine, chlorine, bromine, or iodine atom, preferably a fluorine or chlorine atom.

"Alkali metal" represented by $R_1$ includes sodium or potassium.

"Alkaline earth metal" represented by $R_1$ includes calcium or magnesium.

$C_{1-18}$ alkyl represented by $R_1$, $R_3$, $R_4$, $R_5$, $R_6$, $R_7$, or $R_8$ may be either a straight-chain or branched-chain configuration, preferably $C_{1-10}$ alkyl, more preferably $C_{1-4}$ alkyl. The $C_{1-18}$ alkyl group may be substituted. Substituents in this case include a halogen atom, $C_{1-4}$ alkyloxy, $C_{1-4}$ alkyloxy-$C_{1-4}$ alkyloxy, $C_{1-4}$ alkyloxycarbonyl, nitro, cyano, formyl, trifluoromethoxy, acetyl, acetyloxy, or $C_{3-6}$ cycloalkyl optionally substituted by halogen atom. Preferred examples thereof include a halogen atom, $C_{1-4}$ alkyloxy, $C_{1-4}$ alkyloxy-$C_{1-4}$ alkyloxy, $C_{1-4}$ alkyloxycarbonyl, cyano, acetyloxy, or $C_{3-6}$ cycloalkyl optionally substituted by halogen atom. The substituent in $R_1$ is more preferably $C_{1-4}$ alkyloxy-$C_{1-4}$ alkyloxy or $C_{1-4}$ alkyloxycarbonyl. The substituent in $R_3$ is more preferably a halogen atom or acetyloxy. The substituent in $R_4$ is more preferably $C_{1-4}$ alkyloxy or acetyloxy. The substituent in $R_5$ is more preferably a halogen atom or $C_{1-4}$ alkyloxy. The substituent in $R_6$, $R_7$, or $R_8$ is more preferably a halogen atom, $C_{1-4}$ alkyloxy, or acetyloxy.

Specific examples of $C_{1-18}$ alkyl represented by $R_1$, $R_3$, $R_4$, $R_5$, $R_6$, $R_7$, or $R_8$ include methyl, ethyl, propyl, i-propyl, n-butyl, i-butyl, s-butyl, t-butyl, n-pentyl, (2- or 3-methyl)butyl, 2,3-dimethylpropyl, n-hexyl, (2,3- or 4-methyl)pentyl, (2,3-,2,4- or 3,4-dimethyl)butyl, 2,3,4-trimethylpropyl, n-heptyl, n-octyl, nonyl, decyl, undecyl, dodecyl, tridecyl, tetradecyl, pentadecyl, hexadecyl, heptadecyl, octadecyl, chloromethyl, trichloromethyl, trifluoromethyl, (1- or 2-)chloroethyl,2,2,2-trifluoroethyl, pentafluoroethyl, 2-trifluoromethoxyethyl, cyanomethyl, 2-cyanoethyl, cyclopropylmethyl, cyclopropylethyl, cyclopropylpropyl, 1-methylcyclopropylmethyl,2-(1-methylcyclopropyl)ethyl, 3-(1-methylcyclopropyl)propyl,2,2-dimethylcyclopropylmethyl, 2-(2,2-dimethylcyclopropyl)ethyl,3-(2,2-dimethylcyclopropyl)propyl, 2,2-dichlorocyclopropylmethyl, 2-(2,2-dichlorocyclopropyl)ethyl, 3-(2,2-dichlorocyclopropyl)propyl,2,2-difluorocyclopropylmethyl, 2-(2,2-difluorocyclopropyl)ethyl,or 3-(2,2-difluorocyclopropyl)propyl.

$C_{1-4}$ alkyl represented by $R_2$ may be in either a straight-chain or branched-chain configuration. The $C_{1-4}$ alkyl group may be substituted, and examples of substituents include a halogen atom, $C_{1-4}$ alkyloxy, nitro, cyano, formyl, trifluoromethoxy, acetyl, acetyloxy, or $C_{3-6}$ cycloalkyl optionally substituted by halogen atom, preferably a halogen atom or cyano.

Specific examples of $C_{1-4}$ alkyl represented by $R_2$ include methyl, ethyl, propyl, i-propyl, n-butyl, i-butyl, s-butyl, t-butyl, chloromethyl, trichloromethyl, trifluoromethyl, (1- or 2-)chloroethyl, 2,2,2-trifluoroethyl, pentafluoroethyl, 2-trifluoromethoxyethyl, cyanomethyl, or 2-cyanoethyl.

$C_{2-18}$ alkenyl represented by $R_1$, $R_4$, $R_5$, or $R_8$ may be in either a straight-chain or branched-chain configuration, preferably $C_{2-10}$ alkenyl, more preferably $C_{2-4}$ alkenyl. The $C_{2-18}$ alkenyl group may be substituted, and examples of substituent include a halogen atom, $C_{1-4}$ alkyloxy, nitro, cyano, formyl, trifluoromethoxy, acetyl, acetyloxy, or $C_{3-6}$ cycloalkyl optionally substituted by halogen atom. The substituent in $R_4$ or $R_5$ is preferably a halogen atom, $C_{1-4}$ alkyloxy, nitro, cyano, formyl, trifluoromethoxy, acetyl, or acetyloxy. The substituent in $R_1$, $R_4$, $R_5$, or $R_8$ is more preferably a halogen atom.

Specific examples of $C_{2-18}$ alkenyl represented by $R_1$, $R_4$, $R_5$, or $R_8$ include vinyl, (1- or 2-)propenyl, (1-, 2- or 3-)butenyl, (1-, 2-, 3- or 4-)pentenyl, (1-, 2-, 3-, 4- or 5-)hexenyl, (1-, 2-, 3-, 4-, 5- or 6-)heptenyl, (1-, 2-, 3-, 4-, 5-, 6- or 7-)octenyl, (1-, 2-, 3-, 4-, 5-, 6-, 7- or 8-)nonenyl, (1-, 2-, 3-, 4-, 5-, 6-, 7-, 8- or 9-)decenyl, (1-, 2-, 3-, 4-, 5-, 6-, 7-, 8-, 9- or 10-)undecenyl,(1-, 2-, 3-, 4-, 5-, 6-, 7-, 8-, 9-, 10- or 11-)dodecenyl,(1-, 2-, 3-, 4-, 5-, 6-, 7-, 8-, 9-, 10-, 11- or 12-)tridecenyl, (1-, 2-, 3-, 4-, 5-, 6-, 7-, 8-, 9-, 10-, 11-, 12- or 13-)tetradecenyl, (1-, 2-, 3-, 4-, 5-, 6-, 7-, 8-, 9-, 10-, 11-, 12-, 13- or 14-)pentadecenyl, (1-, 2-, 3-, 4-, 5-, 6-, 7-, 8-, 9-, 10-, 11-, 12-, 13-, 14- or 15-)hexadecenyl, (1-, 2-, 3-, 4-, 5-, 6-, 7-, 8-, 9-, 10-, 11-, 12-, 13-, 14-, 15- or 16-)heptadecenyl, (1-, 2-, 3-, 4-, 5-, 6-, 7-, 8-, 9-, 10-, 11-, 12-, 13-, 14-, 15-, 16- or 17-)octadecenyl, 1-methyl vinyl, 1-methyl-1-propenyl, 2-methyl-1-propenyl, 1,2-dimethyl-1-propenyl, 1-methyl-1- butenyl, 1-methyl-2-butenyl, 2-fluoro vinyl, 2-chloro vinyl, 2,2-difluoro vinyl, 2,2-dichloro vinyl, or 2-trifluoromethoxy vinyl.

$C_{2-4}$ alkenyl represented by $R_3$ may be in either a straight-chain or branched-chain configuration. The $C_{2-4}$ alkenyl group may be substituted, and examples of substituents include a halogen atom, $C_{1-4}$ alkyloxy, nitro, cyano, formyl, trifluoromethoxy, acetyl, acetyloxy, or $C_{3-6}$ cycloalkyl optionally substituted by halogen atom, preferably a halogen atom.

$C_{2-18}$ alkynyl represented by $R_1$, $R_4$, $R_5$, or $R_8$ may be in either a straight-chain or branched-chain configuration, preferably $C_{2-10}$ alkynyl, more preferably $C_{2-4}$ alkynyl. The $C_{2-18}$ alkynyl group may be substituted, and examples of substituent include a halogen atom, $C_{1-4}$ alkyloxy, nitro, cyano, formyl, trifluoromethoxy, acetyl, acetyloxy, or $C_{3-6}$ cycloalkyl optionally substituted by halogen atom.

Specific examples of $C_{2-18}$ alkynyl represented by $R_1$, $R_4$, $R_5$ or $R_8$ include ethynyl, (1- or 2-)propynyl, (1-, 2- or 3-)butynyl, (1-, 2-, 3- or 4-)pentynyl, (1-, 2-, 3-, 4- or 5-)hexynyl, (1-, 2-, 3-, 4-, 5- or 6-)heptynyl, (1-, 2-, 3-, 4-, 5-, 6- or 7-)octynyl, (1-, 2-, 3-, 4-, 5-, 6-, 7- or 8-)nonynyl, (1-, 2-, 3-, 4-, 5-, 6-, 7-, 8- or 9-)decynyl, (1-, 2-, 3-, 4-, 5-, 6-, 7-, 8-, 9- or 10-)undecynyl, (1-, 2-, 3-, 4-, 5-, 6-, 7-, 8-, 9-, 10- or 11-)dodecynyl, (1-, 2-, 3-, 4-, 5-, 6-, 7-, 8-, 9-, 10-, 11- or 12-)tridecynyl, (1-, 2-, 3-, 4-, 5-, 6-, 7-, 8-, 9-, 10-, 11-, 12- or 13-)tetradecynyl, (1-, 2-, 3-, 4-, 5-, 6-, 7-, 8-, 9-, 10-, 11-, 12-, 13- or 14-)pentadecynyl, (1-, 2-, 3-, 4-, 5-, 6-, 7-, 8-, 9-, 10-, 11-, 12-, 13-, 14- or 15-)hexadecynyl, (1-, 2-, 3-, 4-, 5-, 6-, 7-, 8-, 9-, 10-, 11-, 12-, 13-, 14-, 15- or 16-)heptadecynyl, or (1-, 2-, 3-, 4-, 5-, 6-, 7-, 8-, 9-, 10-, 11-, 12-, 13-, 14-, 15-, 16- or 17-)octadecynyl.

$C_{3-10}$ cycloalkyl represented by $R_1$, $R_4$, $R_5$ or $R_8$ is preferably $C_{3-6}$ cycloalkyl. The $C_{3-10}$ cycloalkyl group may be substituted, and examples of substituents include a halogen atom, $C_{1-4}$ alkyloxy, nitro, cyano, formyl, trifluoromethyl, trifluoromethoxy, acetyl, acetyloxy, $C_{1-4}$ alkyl, or $C_{3-6}$ cycloalkyl optionally substituted by halogen atom, preferably a halogen atom or $C_{1-4}$ alkyl.

Specific examples of $C_{3-10}$ cycloalkyl represented by $R_1$, $R_4$, $R_5$ or $R_8$ include cyclopropyl, cyclobutyl, cyclopentyl, cyclohexyl, cycloheptyl, cyclooctyl, cyclononyl, cyclodecyl, 1-methylcyclopropyl, 2-methylcyclopropyl, 1-methyl-2-ethylcyclopropyl, 2-chlorocyclopropyl, 2-fluorocyclopropyl, 2,2-dimethylcyclopropyl, 2,2-dichlorocyclopropyl, 2,2-difluorocyclopropyl, 1-methyl-2-chlorocyclopropyl, 1-methyl-2-fluorocyclopropyl, 1-methyl-2,2-dimethylcyclopropyl, 1-methyl-2,2-dichlorocyclopropyl, 1-methyl-2,2-difluorocyclopropyl, 1-methylcyclobutyl, 2-methylcyclobutyl, 2-chlorocyclobutyl, 2-fluorocyclobutyl, 2,2-dimethylcyclobutyl, 2,2-dichlorocyclobutyl, 2,2-difluorocyclobutyl, 1-methylcyclopentyl, 2-methylcyclopentyl, 3-methylcyclopentyl, 3-chlorocyclopentyl, 3-fluorocyclopentyl, 3,3-dimethylcyclopentyl, 3,3-dichlorocyclopentyl, 3,3-difluorocyclopentyl, 1-methylcyclohexyl, or 2,2-dimethylcyclohexyl.

Preferably, phenyl lower alkyl represented by $R_1$, $R_4$, $R_5$ or $R_8$ is $C_{1-4}$ alkyl containing phenyl. The phenyl group in the phenyl lower alkyl group may be substituted, and examples of substituents include a halogen atom, $C_{1-4}$ alkyl, $C_{1-4}$ alkyloxy, nitro, cyano, formyl, trifluoromethyl, trifluoromethoxy, acetyl, acetyloxy, or $C_{3-6}$ cycloalkyl optionally substituted by halogen atom.

Specific examples of phenyl lower alkyl represented by $R_1$, $R_4$, $R_5$ or $R_8$ include benzyl, (1- or 2-)phenylethyl, (1-, 2- or 3-)phenylpropyl, (1-, 2-, 3- or 4-)phenylbutyl.

Preferably, phenoxy lower alkyl represented by $R_1$, $R_4$, $R_5$ or $R_8$ is phenoxy-containing $C_{1-4}$ alkyl. In this case, the phenyl group in the phenoxy lower alkyl group may be substituted, and examples of substituents include halogen atom, $C_{1-4}$ alkyl, $C_{1-4}$ alkyloxy, nitro, cyano, formyl, trifluoromethyl, trifluoromethoxy, acetyl, acetyloxy, or $C_{3-6}$ cycloalkyl optionally substituted by halogen atom.

Specific examples of phenoxy lower alkyl represented by $R_1$, $R_4$, $R_5$ or $R_8$ include phenoxymethyl, (1- or 2-)phenoxyethyl, (1-, 2- or 3-)phenoxypropyl, or (1-, 2-, 3- or 4-)phenoxybutyl. The phenyl group may be substituted, and preferred substituents include a halogen atom, $C_{1-4}$ alkyl, $C_{1-4}$ alkyloxy, nitro, cyano, formyl, trifluoromethoxy, acetyl, or acetyloxy.

Phenyl represented by $R_1$, $R_4$, $R_5$, $R_6$, $R_7$ or $R_8$ may be substituted, and preferred substituents include a halogen atom, $C_{1-4}$ alkyl, $C_{1-4}$ alkyloxy, nitro, cyano, formyl, trifluoromethyl, trifluoromethoxy, acetyl, acetyloxy, or $C_{3-6}$ cycloalkyl optionally substituted by halogen atom.

The heterocyclic group represented by $R_1$, $R_4$, $R_5$ or $R_8$ is preferably a five- or six-membered saturated heterocyclic or aromatic ring containing one S, O, or N as a heteroatom, a five- or six-membered saturated heterocyclic or aromatic ring containing two N as a heteroatom, a five- or six-membered saturated heterocyclic or aromatic ring containing O or S and one N as heteroatoms, more preferably a cyclic group selected is from the group consisting of thienyl, furyl, pyrrolyl, imidazolyl, pyrazolyl, isothiazolyl, isoxazolyl, thiazolyl, oxazolyl, pyridyl, and pyrimidinyl. The heterocyclic group may be substituted, and examples of substituents include a halogen atom, $C_{1-4}$ alkyl, $C_{1-4}$ alkyloxy, nitro, cyano, formyl, trifluoromethyl, trifluoromethoxy, acetyl, acetyloxy, or $C_{3-6}$ cycloalkyl optionally substituted by halogen atom.

Specific examples of the heterocyclic group represented by $R_1$, $R_4$, $R_5$ or $R_8$ include (2- or 3-)thienyl, (2- or 3-)furyl, (1-, 2- or 3-)pyrrolyl, (1- or 2-)imidazolyl, (1-, 3-, 4- or 5-)pyrazolyl, (3-, 4- or 5-)isothiazolyl, (3-, 4- or 5-)isoxazolyl, (2-, 4- or 5-)thiazolyl, (2-, 4- or 5-)oxazolyl, (2-, 3- or 4-)pyridyl, or (2-, 4-, 5- or 6-)pyrimidinyl.

$C_{1-4}$ alkylthio represented by $R_4$ may be in either a straight-chain or branched-chain configuration. The $C_{1-4}$ alkylthio group may be substituted, and examples of substituents include a halogen atom, $C_{1-4}$ alkyloxy, nitro, cyano, formyl, trifluoromethoxy, acetyl, acetyloxy, or $C_{3-6}$ cycloalkyl optionally substituted by halogen atom, preferably a halogen atom.

$C_{1-4}$ alkoxy represented by $R_3$ may be in either a straight-chain or branched-chain configuration. The $C_{1-4}$ alkoxy group may be substituted, and examples of substituents include a halogen atom, $C_{1-4}$ alkyloxy, nitro, cyano, formyl, trifluoromethoxy, acetyl, acetyloxy, or $C_{3-6}$ cycloalkyl optionally substituted by halogen atom, preferably a halogen atom.

Specific examples of $C_{1-4}$ alkyl optionally substituted by halogen atom represented by $X_1$, $X_2$, and $X_3$ include methyl, ethyl, n-propyl, n-butyl, iso-propyl, iso-butyl, s-butyl, t-butyl, trifluoromethyl, trichloromethyl, difluoromethyl, dichloromethyl, trifluoroethyl, trichloroethyl, tetrafluoroethyl, or tetrachloroethyl, preferably methyl, ethyl, trifluoromethyl, trichloromethyl, difluoromethyl, dichloromethyl, trifluoroethyl, trichloroethyl, pentafluoroethyl, or pentachloroethyl, more preferably methyl, ethyl, trifluoromethyl, or difluoromethyl.

Specific examples of $C_{1-4}$ alkyloxy optionally substituted by halogen atom represented by $X_1$, $X_2$, and $X_3$ include methoxy, ethoxy, n-propyloxy, n-butyloxy, iso-propyloxy, iso-butyloxy, s-butyloxy, t-butyloxy, trifluoromethoxy, trichloromethoxy, difluoromethoxy, dichloromethoxy, trifluoroethoxy, trichloroethoxy, pentafluoroethoxy, or pentachloroethoxy, preferably methoxy, ethoxy, trifluoromethoxy, trichloromethoxy, difluoromethoxy, dichloromethoxy, trifluoroethoxy, trichloroethoxy, pentafluoroethoxy, or pentachloroethoxy, more preferably methoxy, ethoxy, trifluoromethoxy, or difluoromethoxy.

Specific examples of $C_{1-4}$ alkylthio optionally substituted by halogen atom represented by $X_1$, $X_2$, and $X_3$ include methylthio, ethylthio, n-propylthio, n-butylthio, iso-propylthio, iso-butylthio, s-butylthio, t-butylthio, trifluoromethylthio, trichloromethylthio, difluoromethylthio, dichloromethylthio, trifluoroethylthio, trichloroethylthio, pentafluoroethylthio, or pentachloroethylthio, preferably methylthio, ethylthio, trifluoromethylthio, trichloromethylthio, difluoromethylthio, dichloromethylthio, trifluoroethylthio, trichloroethylthio, tetrafluoroethylthio, or tetrachloroethylthio, more preferably methylthio, ethylthio, trifluoromethylthio, or difluoromethylthio.

Specific examples of $C_{1-4}$ alkyloxycarbonyl optionally substituted by halogen atom represented by $X_1$, $X_2$, and $X_3$ include methoxycarbonyl, ethoxycarbonyl, n-propyloxycarbonyl, n-butyloxycarbonyl, iso-propyloxycarbonyl, iso-butyloxycarbonyl, s-butyloxycarbonyl, t-butyloxycarbonyl, trifluoromethoxycarbonyl, trichloromethoxycarbonyl, difluoromethoxycarbonyl, dichloromethoxycarbonyl, trifluoroethoxycarbonyl, trichloroethoxycarbonyl, tetrafluoroethoxycarbonyl, tetrachloroethoxycarbonyl, pentafluoroethoxycarbonyl, or pentachloroethoxycarbonyl, preferably methoxycarbonyl, ethoxycarbonyl, trifluoromethoxycarbonyl, trichloromethoxycarbonyl, difluoromethoxycarbonyl, dichloromethoxycarbonyl, trifluoroethoxycarbonyl, trichloroethoxycarbonyl, pentafluoroethoxycarbonyl, or pentachloroethoxycarbonyl, more preferably methoxycarbonyl, ethoxycarbonyl, trifluoromethoxycarbonyl, or difluoromethoxycarbonyl.

Preferably, $W_1$, $W_2$, and $W_3$ represent C—$Y_1$, C—$Y_2$, and C—$Y_3$, respectively, and, preferably, $W_{11}$, $W_{12}$, and $W_{13}$ represent C—$Y_{11}$, C—$Y_{12}$, and C—$Y_{13}$, respectively.

$C_{1-8}$ alkyl represented by $Y_1$, $Y_2$, $Y_3$, $Y_4$, and $Y_5$, or $Y_{11}$, $Y_{12}$, $Y_{13}$, $Y_{14}$, and $Y_{15}$ is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different. The $C_{1-8}$ alkyl group is preferably substituted by one or more halogen atoms which may be the same or different, and/or $C_{1-4}$ alkyloxy substituted by one or more halogen atoms which may be the same or different, more preferably by one or more halogen atoms which may be the same or different. Specific examples of $C_{1-8}$ alkyl include chloromethyl, (1- or 2-)chloroethyl, (1-, 2- or 3-)chloro-n-propyl, (1-, 2-, 3- or 4-)chloro-n-butyl, (1-, 2-, 3-, 4- or 5-)chloro-n-pentyl, (1-, 2-, 3-, 4-, 5- or 6-)chloro-n-hexyl, (1-, 2-, 3-, 4-, 5-, 6- or 7-)chloro-n-heptyl, (1-, 2-, 3-, 4-, 5-, 6-, 7- or 8-)chloro-n-octyl, fluoromethyl, (1- or 2-)fluoroethyl, (1-, 2- or 3-)fluoro-n-propyl, (1-, 2-, 3- or 4-)fluoro-n-butyl, (1-, 2-, 3-, 4- or 5-)fluoro-n-pentyl, (1-, 2-, 3-, 4-, 5- or 6-)fluoro-n-hexyl, (1-, 2-, 3-, 4-, 5-, 6- or 7-)fluoro-n-heptyl, (1-, 2-, 3-, 4-, 5-, 6-, 7- or 8-)fluoro-n-octyl, dichloromethyl, difluoromethyl, trichloromethyl, trifluoromethyl, trichloroethyl, trifluoroethyl, pentachloroethyl, pentafluoroethyl, 3,3,3-trichloropropyl, 3,3,3-trifluoropropyl, 2,2,3,3-tetrachloropropyl, 2,2,3,3-tetrafluoropropyl, ditrifluoromethylmethyl, 2,2-ditrifluoromethylethyl, heptafluoro-iso-propyl, nonafluoro-iso-butyl, chloromethoxymethyl, (1- or 2-)chloromethoxyethyl, (1-, 2- or 3-)chloromethoxy-n-propyl, (1-, 2-, 3- or 4-)chloromethoxy-n-butyl, (1-, 2-, 3-, 4- or 5-)chloromethoxy-n-pentyl, (1-, 2-, 3-, 4-, 5- or 6-)chloromethoxy-n-hexyl, (1-, 2-, 3-, 4-, 5-, 6- or 7-)chloromethoxy-n-heptyl, (1-, 2-, 3-, 4-, 5-, 6-, 7- or 8-)chloromethoxy-n-octyl, fluoromethoxymethyl, (1- or 2-)fluoromethoxyethyl, (1-, 2- or 3-)fluoromethoxy-n-propyl, (1-, 2-, 3- or 4-)fluoromethoxy-n-butyl, (1-, 2-, 3-, 4- or 5-)fluoromethoxy-n-pentyl, (1-, 2-, 3-, 4-, 5- or 6-)fluoromethoxy-n-hexyl, (1-, 2-, 3-, 4-, 5-, 6- or 7-)fluoromethoxy-n-heptyl, (1-, 2-, 3-, 4-, 5-, 6-, 7- or 8-)fluoromethoxy-n-octyl, dichloromethoxymethyl, difluoromethoxymethyl, trichloromethoxymethyl, trifluoromethoxymethyl, trichloromethoxyethyl, trifluoromethoxyethyl, pentachloroethoxymethyl, pentafluoroethoxymethyl, pentachloroethoxyethyl, pentafluoroethoxyethyl, 3,3,3-trichloropropyloxymethyl, 3,3,3-trifluoropropyloxymethyl, 3,3,3-trichloropropyloxyethyl, 3,3,3-trifluoropropyloxyethyl, 2,2,3,3-tetrachloropropyloxymethyl, 2,2,3,3-tetrafluoropropyloxymethyl, or trifluoromethoxy-1,1,2-trifluoroethyl, preferably chloromethyl, (1- or 2-)chloroethyl, (1-, 2- or 3-)chloro-n-propyl, fluoromethyl, (1- or 2-)fluoroethyl, (1-, 2- or 3-)fluoro-n-propyl, dichloromethyl, difluoromethyl, trichloromethyl, trifluoromethyl, trichloroethyl, trifluoroethyl, pentachloroethyl, pentafluoroethyl, 3,3,3-trichloropropyl, 3,3,3-trifluoropropyl,2,2,3,3-tetrachloropropyl, 2,2,3,3-tetrafluoropropyl, ditrifluoromethylmethyl, 2,2-ditrifluoromethylethyl, heptafluoro-iso-propyl, chloromethoxymethyl, (1- or 2-)chloromethoxyethyl, (1-, 2- or 3-)-chloromethoxy-n-propyl, (1-, 2-, 3- or 4-)chloromethoxy-n-butyl, fluoromethoxymethyl, (1- or 2-)fluoromethoxyethyl, (1-, 2- or 3-)-fluoromethoxy-n-propyl, (1-, 2-, 3- or 4-)fluoromethoxy-n-butyl, dichloromethoxymethyl, difluoromethoxymethyl, trichloromethoxymethyl, trifluoromethoxymethyl, trichloromethoxyethyl, trifluoromethoxyethyl, pentachloroethoxymethyl, pentafluoroethoxymethyl, pentachloroethoxyethyl, pentafluoroethoxyethyl, 3,3,3-trichloropropyloxymethyl, 3,3,3-trifluoropropyloxymethyl, 3,3,3-trichloropropyloxyethyl, 3,3,3-trifluoropropyloxyethyl, 2,2,3,3-tetrachloropropyloxymethyl, 2,2,3,3-tetrafluoropropyloxymethyl, or trifluoromethoxy-1,1,2-trifluoroethyl, more preferably trifluoromethyl, trifluoroethyl, tetrafluoroethyl, 3,3,3-trifluoropropyl, 2,2,3,3-tetrafluoropropyl, difluoromethoxymethyl, trifluoromethoxymethyl, trifluoromethoxyethyl, pentafluoroethoxymethyl, pentafluoroethoxyethyl, 3,3,3-trifluoropropyloxymethyl, 3,3,3-trifluoropropyloxyethyl, 2,2,3,3-tetrafluoropropyloxymethyl, or trifluoromethoxy-1,1,2-trifluoroethyl.

$C_{2-8}$ alkenyl represented by $Y_1$, $Y_2$, $Y_3$, $Y_4$, and $Y_5$, or $Y_{11}$, $Y_{12}$, $Y_{13}$, $Y_{14}$, and $Y_{15}$ is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different, preferably substituted by one or more halogen atoms which may be the same or different. Specific examples of $C_{2-8}$ alkenyl include 2-chloro-3,3,3-trifluoro-1-propenyl.

$C_{1-8}$ alkyloxy represented by $Y_1$, $Y_2$, $Y_3$, $Y_4$, and $Y_5$, or $Y_{11}$, $Y_{12}$, $Y_{13}$, $Y_{14}$, and $Y_{15}$ is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different. This $C_{1-8}$ alkyloxy group is preferably substituted by one or more halogen atoms which may be the same or different, and/or $C_{1-4}$ alkyloxy substituted by one or more halogen atoms which may be the same or different. In one embodiment, this $C_{1-8}$ alkyloxy group is substituted by one or more halogen atoms which may be the same or different. Specific examples of $C_{1-8}$ alkyloxy include chloromethyloxy, (1- or 2-)chloroethyloxy, (1-, 2- or 3-)chloro-n-propyloxy, (1-, 2-, 3- or 4-)chloro-n-butyloxy, (1-, 2-, 3-,4- or 5-)chloro-n-pentyloxy, (1-, 2-, 3-, 4-, 5- or 6-)chloro-n-hexyloxy, (1-, 2-, 3-, 4-, 5-, 6- or 7-)chloro-n-heptyloxy, (1-, 2-, 3-, 4-, 5-, 6-, 7- or 8-)-chloro-n-octyloxy, fluoromethyloxy,(1- or 2-)fluoroethyloxy, (1-, 2- or 3-)-fluoro-n-propyloxy, (1-, 2-, 3- or 4-)fluoro-n-butyloxy, (1-, 2-, 3-, 4- or 5-)fluoro-n-pentyloxy, (1-, 2-, 3-, 4-, 5- or 6-)fluoro-n-hexyloxy, (1-, 2-, 3-, 4-, 5-, 6- or 7-)fluoro-n-heptyloxy, (1-, 2-, 3-, 4-, 5-, 6-, 7- or 8-)fluoro-n-octyloxy, dichloromethyloxy, difluoromethyloxy, trichloromethyloxy, trifluoromethyloxy, trichloroethyloxy, trifluoroethyloxy, pentachloroethyloxy, pentafluoroethyloxy, 3,3,3-trichloropropyloxy, 3,3,3-trifluoropropyloxy, 2,2,3,3-tetrachloropropyloxy, 2,2,3,3-tetrafluoropropyloxy, ditrifluoromethylmethyloxy, 2,2-ditrifluoromethylethyloxy, heptafluoro-iso-propyloxy, nonafluoro-iso-butyloxy, chloromethoxymethoxy, (1- or 2-)chloromethoxymethoxy, (1-, 2- or 3-)chloromethoxy-n-propyloxy, (1-, 2-, 3- or 4-)chloromethoxy-n-butyloxy, (1-, 2-, 3-, 4- or 5-)chloromethoxy-n-pentyloxy, (1-, 2-, 3-, 4-, 5- or 6-)chloromethoxy-n-hexyloxy, (1-, 2-, 3-, 4-, 5-, 6- or 7-)-chloromethoxy-n-heptyloxy, (1-, 2-, 3-, 4-, 5-, 6-, 7- or 8-)-chloromethoxy-n-octyloxy, fluoromethoxymethoxy, (1- or 2-)-fluoromethoxyethoxy, (1-, 2- or 3-)fluoromethoxy-n-propyloxy, (1-, 2-, 3- or 4-)fluoromethoxy-n-butyloxy, (1-, 2-, 3-, 4- or 5-)fluoromethoxy-n-pentyloxy, (1-, 2-, 3-, 4-, 5- or 6-)fluoromethoxy-n-hexyloxy, (1-, 2-, 3-, 4-, 5-, 6- or 7-)fluoromethoxy-n-heptyloxy, (1-, 2-, 3-, 4-, 5-, 6-, 7- or 8-)-fluoromethoxy-n-octyloxy, dichloromethoxymethoxy, difluoromethoxymethoxy, trichloromethoxymethoxy, trifluoromethoxymethoxy, trichloromethoxyethoxy, trifluoromethoxyethoxy, pentachloroethoxymethoxy, pentafluoroethoxymethoxy, pentachloroethoxyethoxy, pentafluoroethoxyethoxy, 3,3,3-trichloropropyloxymethoxy, 3,3,3-trifluoropropyloxymethoxy, 3,3,3-trichloropropyloxyethoxy, 3,3,3-trifluoropropyloxyethoxy, 2,2,3,3-tetrachloropropyloxymethoxy, 2,2,3,3-tetrafluoropropyloxymethoxy, 1,1,2,2,3,3,3-heptafluoropropyloxy-1,2,2-trifluoroethoxy, 1,1,2,2,3,3,3-heptafluoropropyloxy-1,1,2-trifluoroethoxy, or trifluoromethoxy-1,1,2-trifluoroethoxy, preferably chloromethyloxy, (1- or 2-)chloroethyloxy, (1-, 2- or 3-)chloro-n-propyloxy, fluoromethyloxy, (1- or 2-)fluoroethyloxy, (1-, 2- or 3-)fluoro-n-propyloxy, dichloromethyloxy, difluoromethyloxy, trichloromethyloxy, trifluoromethyloxy, trichloroethyloxy, trifluoroethyloxy, pentachloroethyloxy, pentafluoroethyloxy, 3,3,3-trichloropropyloxy, 3,3,3-trifluoropropyloxy, 2,2,3,3-tetrachloropropyloxy, 2,2,3,3-tetrafluoropropyloxy, ditrifluoromethylmethyloxy, 2,2-ditrifluoromethylethyloxy, heptafluoro-iso-propyloxy, chloromethoxymethoxy, (1- or 2-)chloromethoxyethoxy, (1-, 2- or 3-)-chloromethoxy-n-propyloxy, (1-, 2-, 3- or 4-)chloromethoxy-n-butyloxy, fluoromethoxymethoxy, (1- or 2-)fluoromethoxyethoxy, (1-, 2-or 3-)-fluoromethoxy-n-propyloxy, (1-, 2-, 3- or 4-)fluoromethoxy-n-butyloxy, dichloromethoxymethoxy, difluoromethoxymethoxy, trichloromethoxymethoxy, trifluoromethoxymethoxy, trichloromethoxyethoxy, trifluoromethoxyethoxy, pentachloroethoxymethoxy, pentafluoroethoxymethoxy, pentachloroethoxyethoxy, pentafluoroethoxyethoxy, 3,3,3-trichloropropyloxymethoxy, 3,3,3-trifluoropropyloxymethoxy, 3,3,3-trichloropropyloxyethoxy, 3,3,3-trifluoropropyloxyethoxy, 2,2,3,3-tetrachloropropyloxymethoxy, 2,2,3,3-tetrafluoropropyloxymethoxy, 1,1,2,2,3,3,3-heptafluoropropyloxy-1,2,2-trifluoroethoxy, 1,1,2,2,3,3,3-heptafluoropropyloxy-1,1,2-trifluoroethoxy, or trifluoromethoxy-1,1,2-trifluoroethoxy, more preferably trifluoromethyloxy, trifluoroethyloxy, pentafluoroethyloxy, 3,3,3-trifluoropropyloxy, 2,2,3,3-tetrafluoropropyloxy, difluoromethoxymethoxy, trifluoromethoxymethoxy, trifluoromethoxyethoxy, pentafluoroethoxymethoxy, pentafluoroethoxyethoxy, 3,3,3-trifluoropropyloxymethoxy, 3,3,3-trifluoropropyloxyethoxy, 2,2,3,3-tetrafluoropropyloxymethoxy, 1,1,2,2,3,3,3-heptafluoropropyloxy-1,2,2-trifluoroethoxy, 1,1,2,2,3,3,3-heptafluoropropyloxy-1,1,2-trifluoroethoxy, or trifluoromethoxy-1,1,2-trifluoroethoxy.

$C_{2-8}$ alkenyloxy represented by $Y_1$, $Y_2$, $Y_3$, $Y_4$, and $Y_5$, or $Y_{11}$, $Y_{12}$, $Y_{13}$, $Y_{14}$, and $Y_{15}$ is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different. Specific examples of $C_{2-8}$ alkenyloxy include 3,3-dichloro-2-propenyloxy or 3-chloro-4,4,4-trifluoro-2-butenyloxy.

$C_{1-8}$ alkyloxycarbonyl represented by $Y_1$, $Y_2$, $Y_3$, $Y_4$, and $Y_5$, or $Y_{11}$, $Y_{12}$, $Y_{13}$, $Y_{14}$, and $Y_{15}$ is optionally substituted by one or more halogen atoms which may be the same or different, and/or $C_{1-4}$ alkyloxy substituted by one or more halogen atoms which may be the same or different. Specific examples of $C_{1-8}$ alkyloxycarbonyl include ethyloxycarbonyl.

$C_{1-8}$ alkylthio represented by $Y_1$, $Y_2$, $Y_3$, $Y_4$, and $Y_5$, or $Y_{11}$, $Y_{12}$, $Y_{13}$, $Y_{14}$, and $Y_{15}$ is optionally sbustituted by one or more halogen atoms which may be the same or different, and/or $C_{1-4}$ alkyloxy substituted by one or more halogen atoms which may be the same or different. This $C_{1-8}$ alkylthio group is preferably $C_{1-8}$ alkylthio substituted by one or more halogen atoms which may be the same or different. Specific examples of $C_{1-8}$ alkylthio include methylthio, ethylthio, n-propylthio, n-butylthio, iso-propylthio, iso-butylthio, s-butylthio, t-butylthio, n-pentylthio, (2- or 3-methyl)butylthio, 2,3-dimethylpropylthio, n-hexylthio, (2 or 3 or 4-methyl)pentylthio, (2,3- or 2,4- or 3,4-dimethyl)butylthio, 2,3,4-trimethylpropylthio, n-heptylthio, n-octylthio, trifluoromethylthio, trichloromethylthio, difluoromethylthio, dichloromethylthio, trifluoroethylthio, trichloroethylthio, pentafluoroethylthio, pentachloroethylthio, chloromethoxymethylthio, (1- or 2-)chloromethoxyethylthio, (1-, 2- or 3-)chloromethoxy-n-propylthio, (1-, 2-, 3- or 4-)chloromethoxy-n-butylthio, (1-, 2-, 3-, 4- or 5-)chloromethoxy-n-pentylthio, (1-, 2-, 3-, 4-, 5- or 6-)chloromethoxy-n-hexylthio, (1-, 2-, 3-, 4-, 5-, 6- or 7-)chloromethoxy-n-heptylthio, (1-, 2-, 3-, 4-, 5-, 6-, 7- or 8-)-chloromethoxy-n-octylthio, fluoromethoxymethylthio, (1- or 2-)-fluoromethoxyethylthio, (1-, 2- or 3-)fluoromethoxy-n-propylthio, (1-, 2-, 3- or 4-)fluoromethoxy-n-butylthio, (1-, 2-, 3-, 4- or 5-)fluoromethoxy-n-pentylthio, (1-, 2-, 3-, 4-, 5- or 6-)fluoromethoxy-n-hexylthio, (1-, 2-, 3-, 4-, 5-, 6- or 7-)fluoromethoxy-n-heptylthio, (1-, 2-, 3-, 4-, 5-, 6-, 7- or 8-)-fluoromethoxy-n-octylthio, dichloromethoxymethylthio, difluoromethoxymethylthio, trichloromethoxymethylthio, trifluoromethoxymethylthio, trichloromethoxyethylthio, trifluoromethoxyethylthio, pentachloroethoxymethylthio, pentafluoroethoxymethylthio, pentachloroethoxyethylthio, pentafluoroethoxyethylthio, 3,3,3-trichloropropyloxymethylthio, 3,3,3-trifluoropropyloxymethylthio, 3,3,3-trichloropropyloxyethylthio, 3,3,3-trifluoropropyloxyethylthio, 2,2,3,3-tetrachloropropyloxymethylthio, 2,2,3,3-tetrafluoropropyloxymethylthio, or trifluoromethoxy-1,1,2-trifluoroethylthio, preferably methylthio, ethylthio, trifluoromethylthio, trichloromethylthio, difluoromethylthio, dichloromethylthio, trifluoroethylthio, trichloroethylthio, tetrafluoroethylthio, tetrachloroethylthio, chloromethoxymethylthio, (1- or 2-)chloromethoxyethylthio, (1-, 2- or 3-)chloromethoxy-n-propylthio, (1-, 2-, 3- or 4-)chloromethoxy-n-butylthio, fluoromethoxymethylthio, (1- or 2-)-fluoromethoxyethylthio, (1-, 2- or 3-)fluoromethoxy-n-propylthio, (1-, 2-, 3- or 4-)fluoromethoxy-n-butylthio, dichloromethoxymethylthio, difluoromethoxymethylthio, trichloromethoxymethylthio, trifluoromethoxymethylthio, trichloromethoxyethylthio, trifluoromethoxyethylthio, pentachloroethoxymethylthio, pentafluoroethoxymethylthio, pentachloroethoxyethylthio, pentafluoroethoxyethylthio, 3,3,3-trichloropropyloxymethylthio, 3,3,3-trifluoropropyloxymethylthio, 3,3,3-trichloropropyloxyethylthio, 3,3,3-trifluoropropyloxyethylthio, 2,2,3,3-tetrachloropropyloxymethylthio, 2,2,3,3-tetrafluoropropyloxymethylthio, or trifluoromethoxy-1,1,2-trifluoroethylthio, more preferably methylthio, ethylthio, trifluoromethylthio, difluoromethylthio, difluoromethoxymethylthio, trifluoromethoxymethylthio, trifluoromethoxyethylthio, pentafluoroethoxymethylthio, pentafluoroethoxyethylthio, 3,3,3-trifluoropropyloxymethylthio, 3,3,3-trifluoropropyloxyethylthio, 2,2,3,3-tetrafluoropropyloxymethylthio, or trifluoromethoxy-1,1,2-trifluoroethylthio.

$C_{2-8}$ alkenylthio represented by $Y_1, Y_2, Y_3, Y_4$, and $Y_5$, or $Y_{11}, Y_{12}, Y_{13}, Y_{14}$, and $Y_{15}$ is optionally substituted by one or more halogen atoms which may be the same or different, and/or $C_{1-4}$ alkyloxy substituted by one or more halogen atoms which may be the same or different. Specific examples of $C_{2-8}$ alkenylthio include 3,4,4-fluoro-3-butenylthio and 3,3-dichloro-2-propenylthio.

$C_{1-8}$ alkylsulfinyl represented by $Y_1, Y_2, Y_3, Y_4$, and $Y_5$, or $Y_{11}, Y_{12}, Y_{13}, Y_{14}$, and $Y_{15}$ is optionally substituted by one or more halogen atoms which may be the same or different and/or $C_{1-4}$ alkyloxy substituted by one or more halogen atoms which may be the same or different.

$C_{2-8}$ alkenylsulfinyl represented by $Y_1, Y_2, Y_3, Y_4$, and $Y_5$, or $Y_{11}, Y_{12}, Y_{13}, Y_{14}$, and $Y_{15}$ is optionally substituted by one or more halogen atoms which may be the same or different, and/or $C_{1-4}$ alkyloxy substituted by one or more halogen atoms which may be the same or different.

$C_{1-8}$ alkylsulfonyl represented by $Y_1, Y_2, Y_3, Y_4$, and $Y_5$, or $Y_{11}, Y_{12}, Y_{13}, Y_{14}$, and $Y_{15}$ is optionally substituted by one or more halogen atoms which may be the same or different, and/or $C_{1-4}$ alkyloxy substituted by one or more halogen atoms which may be the same or different. This $C_{1-8}$ alkylsulfonyl group is preferably substituted by one or more halogen atoms which may be the same or different. Specific examples of $C_{1-8}$ alkylsulfonyl include trifluoromethylsulfonyl.

$C_{2-8}$ alkenylsulfonyl represented by $Y_1, Y_2, Y_3, Y_4$, and $Y_5$, or $Y_{11}, Y_{12}, Y_{13}, Y_{14}$, and $Y_{15}$ is optionally substituted by one or more halogen atoms which may be the same or different, and/or $C_{1-4}$ alkyloxy substituted by one or more halogen atoms which may be the same or different.

Phenyl represented by $Y_1, Y_2, Y_3, Y_4$, and $Y_5$, or $Y_{11}, Y_{12}, Y_{13}, Y_{14}$, and $Y_{15}$ is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different. This phenyl group is preferably substituted by one or more halogen atoms which may be the same or different, or $C_{1-4}$ alkyl substituted by one or more halogen atoms which may be the same or different. Specific examples of phenyl include 4-trifluoromethyl-phenyl.

Phenoxy represented by $Y_1, Y_2, Y_3, Y_4$, and $Y_5$, or $Y_{11}, Y_{12}, Y_{13}, Y_{14}$, and $Y_{15}$ is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different. This phenoxy group is preferably substituted by one or more halogen atoms which may be the same or different, or $C_{1-4}$ alkyl substituted by one or more halogen atoms which may be the same or different. Specific examples of phenoxy include 4-trifluoromethyl-phenoxy.

Two of $Y_1, Y_2, Y_3, Y_4$, and $Y_5$ adjoining each other, or two of $Y_{11}, Y_{12}, Y_{13}, Y_{14}$, and $Y_{15}$ adjoining each other together may represent —O—$(CH_2)_n$—O— optionally substituted by halogen atom, —$(CH_2)_n$—O— optionally substituted by halogen atom, —S—$(CH_2)_n$—S— optionally substituted by halogen atom, —$(CH_2)_n$—S— optionally substituted by halogen atom, or —$(CH_2)_n$— optionally substituted by halogen atom, preferably —O—$(CH_2)_n$—O— optionally substitutied by halogen atom. In this case, n is 1, 2, or 3, preferably 1 or 2. Specific examples of such groups include —O—$(CF_2)_2$—O—, —O—$(CH_2)_2$—O—, —$(CF_2)_2$—O—, —O—$(CF_2)_2$—$(CH_2)$—, —S—$(CF_2)_2$—S—, —$(CF_2)_2$—S—, and —$(CF_2)_3$—, preferably —O—$(CF_2)_2$—O—.

Z represents a bond (a single bond), an oxygen atom, a sulfur atom, SO, $SO_2$, -Q-, —O-Q-, —O-Q-O—, or CO. In this case, Q represents $C_{1-4}$ alkylene optionally substituted by halogen atom, cyano, or $C_{1-4}$ alky optionally substituted by halogen atom; —$(CH_2)_p$—$CR_{10}R_{11}$—$(CH_2)_q$— wherein $R_{10}$ and $R_{11}$ together combine with the carbon atom to which they are attached to represent $C_{3-6}$ cycloalkyl optionally substituted by halogen atom or $C_{1-4}$ alkyl optionally substituted by halogen atom, p and q are each independently an integer of 0 to 3; or $C_{2-4}$ alkenylene optionally substituted by halogen atom, cyano, or $C_{1-4}$ alkyl optionally substituted by halogen atom. Preferably, Q represents $C_{1-4}$ alkylene optionally substituted by halogen atom, cyano, or $C_{1-4}$ alkyl optionally substituted by halogen atom. Specific examples of Q include methylene, ethylene, propylene, and 2,2-dimethylpropylene. When Z represents a bond (a single bond), in formula (I) or formula (Ia), two ring parts are attached directry (without through any atom). Z preferably represents a bond (a single bond), an oxygen atom, a sulfur atom, SO, $SO_2$, $CH_2$, $OCH_2$, $O(CH_2)_3O$, or CO, more preferably an oxygen atom, a sulfur atom, SO, $SO_2$, $CH_2$, $OCH_2$, or CO, more preferably an oxygen atom, $OCH_2$, or $O(CH_2)_3O$, still more preferably an oxygen atom.

In a preferred embodiment of the present invention, $R_1$ represents a hydrogen atom; an alkali metal; an alkaline earth metal; optionally substituted $C_{1-18}$ alkyl; $COR_4$ wherein $R_4$ represents optionally substituted $C_{1-18}$ alkyl, optionally substituted $C_{2-18}$ alkenyl, optionally substituted $C_{3-10}$ cycloalkyl, optionally substituted $C_{1-4}$ alkylthio, $OR_5$ wherein $R_5$ represents optionally substituted $C_{1-18}$ alkyl, optionally substituted $C_{2-18}$ alkenyl, or optionally substituted phenyl, or $NR_6R_7$ wherein $R_6$ and $R_7$ each independently represent a hydrogen atom, or optionally substituted $C_{1-18}$ alkyl, or $SO_2R_8$ wherein $R_8$ represents optionally substituted $C_{1-18}$ alkyl. More preferably, $R_1$ represents a hydrogen atom; an alkali metal; an alkaline earth metal; $C_{1-18}$ alkyl optionally substituted by $C_{1-4}$ alkyloxycarbonyl or $C_{1-4}$ alkyloxy-$C_{1-4}$ alkyloxy; $COR_4$ wherein $R_4$ represents $C_{1-18}$ alkyl optionally substituted by $C_{1-4}$ alkyloxy or acetyloxy, $C_{2-18}$ alkenyl, $C_{3-10}$ cycloalkyl, $C_{1-4}$ alkylthio, $OR_5$ wherein $R_5$ represents $C_{1-18}$ alkyl optionally substituted by halogen atom or $C_{1-4}$ alkyloxy, $C_{2-18}$ alkenyl, or phenyl; or $NR_6R_7$ wherein $R_6$ and $R_7$ each independently represent a hydrogen atom or $C_{1-18}$ alkyl; or $SO_2R_8$ wherein $R_8$ represents $C_{1-18}$ alkyl. Still more preferably, $R_1$ represents a hydrogen atom, $COR_4$ wherein $R_4$ represents $C_{1-4}$ alkyl, $OR_5$ wherein $R_5$ represents $C_{1-4}$ alkyl, or $NR_6R_7$ wherein $R_6$ and $R_7$ each independently represent a hydrogen atom or $C_{1-18}$ alkyl. Particularly preferably, $R_1$ represents $COR_4'$ or $COOR_5$ wherein $R_4'$ and $R_5$ represent $C_{1-4}$ alkyl.

In another preferred embodiment, $R_1$ represents a hydrogen atom; an alkali metal; an alkaline earth metal; or $COR_4$ wherein $R_4$ represents optionally substituted $C_{1-18}$ alkyl, optionally substituted $C_{2-18}$ alkenyl, $C_{1-4}$ alkylthio, or $OR_5$ wherein $R_5$ represents optionally substituted $C_{1-18}$ alkyl, or optionally substituted $C_{2-18}$ alkenyl, optionally substituted phenyl. More preferably $R_1$ represents a hydrogen atom; an alkali metal; an alkaline earth metal; or $COR_4$ wherein $R_4$ represents $C_{1-18}$ alkyl, $C_{2-18}$ alkenyl, $C_{1-4}$ alkylthio, or $OR_5$ wherein $R_5$ represents $C_{1-18}$ alkyl optionally substituted by halogen atom or $C_{1-4}$ alkyloxy, $C_{2-18}$ alkenyl, or phenyl. Still more preferably, $R_1$ represents a hydrogen atom or $COR_4$ wherein $R_4$ represents $C_{1-4}$ alkyl or $OR_5$ wherein $R_5$ represents $C_{1-4}$ alkyl.

In a preferred embodiment of the present invention, $R_2$ represents a hydrogen atom or optionally substituted $C_{1-4}$ alkyl, more preferably a hydrogen atom or $C_{1-4}$ alkyl, still more preferably $C_{1-4}$ alkyl.

In a preferred embodiment of the present invention, $R_3$ represents optionally substituted $C_{1-18}$ alkyl, or $R_2$ and $R_3$ together represent —$(CH_2)_m$— wherein m is 3 or 4. More preferably, $R_3$ represents $C_{1-18}$ alkyl optionally substituted by halogen atom or acetyloxy, or $R_2$ and $R_3$ together form —$(CH_2)_m$— wherein m is 3 or 4. More preferably, $R_3$ represents $C_{1-4}$ alkyl, or $R_2$ and $R_3$ together represent —$(CH_2)_m$— wherein m is 3 or 4, more preferably $C_{1-4}$ alkyl.

In a preferred embodiment of the present invention, $X_1$, $X_2$, and $X_3$ each independently represent a hydrogen atom, a halogen atom, $C_{1-4}$ alkyl optionally substituted by halogen atom, $C_{1-4}$ alkyloxy optionally substituted by halogen atom, $C_{1-4}$ alkyloxycarbonyl optionally substituted by halogen atom, nitro, or cyano, provided that $X_1$, $X_2$, and $X_3$ do not simultaneously represent a hydrogen atom. More preferably, $X_1$, $X_2$, and $X_3$ each independently represent a hydrogen atom, a halogen atom, $C_{1-4}$ alkyl optionally substituted by halogen atom, $C_{1-4}$ alkyloxy, $C_{1-4}$ alkyloxycarbonyl, nitro, or cyano, provided that $X_1$, $X_2$, and $X_3$ do not simultaneously represent a hydrogen atom. Still more preferably, $X_1$ and $X_2$ each independently represent a hydrogen atom, a halogen atom, $C_{1-4}$ alkyl optionally substituted by halogen atom, $C_{1-4}$ alkyloxy, or $C_{1-4}$ alkyloxycarbonyl, provided that $X_1$ and $X_2$ do not simultaneously represent a hydrogen atom, and $X_3$ represents a hydrogen atom. Particularly preferably, $X_1$ and $X_2$ each independently represent a hydrogen atom, or $C_{1-4}$ alkyl optionally substituted by halogen atom, provided that $X_1$ and $X_2$ do not simultaneously represent a hydrogen atom, and $X_3$ represents a hydrogen atom.

In another preferred embodiment, $X_1$, $X_2$, and $X_3$ each independently represent a hydrogen atom, a halogen atom, $C_{1-4}$ alkyl optionally substituted by halogen atom, $C_{1-4}$ alkyloxy, nitro, or cyano, provided that $X_1$, $X_2$, and $X_3$ do not simultaneously represent a hydrogen atom. More preferably, $X_1$ and $X_2$ each independently represent a hydrogen atom, or $C_{1-4}$ alkyl optionally substituted by halogen atom, and $X_3$ represents a hydrogen atom.

In a preferred embodiment of the present invention, Z represents a bond, an oxygen atom, a sulfur atom, SO, $SO_2$, $CH_2$, $OCH_2$, $O(CH_2)_3O$, or CO, more preferably an oxygen atom, $OCH_2$, or $O(CH_2)_3O$. More preferably, Z represents an oxygen atom.

In a preferred embodiment of the present invention, when $W_1$, $W_2$, and $W_3$ represent C—$Y_1$, C—$Y_2$, and C—$Y_3$, respectively, or when $W_{11}$, $W_{12}$, and $W_{13}$ represent C—$Y_{11}$, C—$Y_{12}$, and C—$Y_{13}$, respectively, $Y_1$, $Y_2$, $Y_3$, $Y_4$, and $Y_5$, or $Y_{11}$, $Y_{12}$, $Y_{13}$, $Y_{14}$, and $Y_{15}$ each independently represent a hydrogen atom, the following A' or B', provided that, when Z represents a bond, methylene optionally substituted by one or two methyl, or an oxygen atom, at least one of $Y_1$, $Y_2$, $Y_3$, $Y_4$, and $Y_5$ represents a group selected from A', or adjacent two of $Y_1$, $Y_2$, $Y_3$, $Y_4$, and $Y_5$, or adjacent two of $Y_{11}$, $Y_{12}$, $Y_{13}$, $Y_{14}$, and $Y_{15}$ may together represent —O—$(CH_2)_n$—O—, wherein n is 1 or 2, substituted by halogen atom.

Here, wherein A' represents a group selected from the group consisting of: $C_{1-8}$ alkyl substituted by one or more halogen atoms which may be the same or different; $C_{1-8}$ alkyloxy substituted by one or more halogen atoms which may be the same or different, and/or $C_{1-4}$ alkyloxy substituted by one or more halogen atoms which may be the same or different; $C_{1-8}$ alkyloxycarbonyl; $C_{1-8}$ alkylthio substituted by one or more halogen atoms which may be the same or different; $C_{1-8}$ alkylsulfonyl substituted by one or more halogen atoms which may be the same or different; phenyl substituted by one or more halogen atoms which may be the same or different, or $C_{1-4}$ alkyl substituted by one or more halogen atoms which may be the same or different; and phenoxy substituted by one or more halogen atoms which may be the same or different, or $C_{1-4}$ alkyl substituted by one or more halogen atoms which may be the same or different. In one embodiment, A' represents a group selected from the group consisting of: $C_{1-8}$ alkyl substituted by one or more halogen atoms which may be the same or different; $C_{1-8}$ alkyloxy substituted by one or more halogen atoms which may be the same or different; $C_{1-8}$ alkylthio substituted by one or more halogen atoms which may be the same or different; $C_{1-8}$ alkylsulfonyl subsituted by one or more halogen atoms which may be the same or different; phenyl substituted by one or more halogen atoms which may be the same or different, or $C_{1-4}$ alkyl substituted by one or more halogen atoms which may be the same or different; and phenoxy substituted by one or more halogen atoms which may be the same or different, or $C_{1-4}$ alkyl substituted by one or more halogen atoms which may be the same or different. B' represents a group selected from the group consisting of a halogen atom, $C_{1-4}$ alkyl, $C_{1-4}$ alkyloxy, and cyano.

In a further preferred embodiment of the present invention, when $W_1$, $W_2$, and $W_3$ represent C—$Y_1$, C—$Y_2$, and C—$Y_3$, respectively, or when $W_{11}$, $W_{12}$, and $W_{13}$ represent C—$Y_{11}$, C—$Y_{12}$, and C—$Y_{13}$, respectively, $Y_1$, $Y_2$, $Y_3$, $Y_4$, and $Y_5$, or $Y_{11}$, $Y_{12}$, $Y_{13}$, $Y_{14}$, and $Y_{15}$ each independently represent a hydrogen atom; $C_{1-8}$ alkyl substituted by one or more halogen atoms which may be the same or different, $C_{1-8}$ alkyloxy substituted by one or more halogen atoms which may be the same or different, and/or $C_{1-4}$ alkyloxy substituted by one or more halogen atoms which may be the same or different; $C_{1-8}$ alkylthio substituted by one or more halogen atoms which may be the same or different; or a halogen atom, provided that at least one of $Y_1$, $Y_2$, $Y_3$, $Y_4$, and $Y_5$ represents a group other than a hydrogen atom and a halogen atom. Alternatively, two of $Y_1$, $Y_2$, $Y_3$, $Y_4$, and $Y_5$, or two of $Y_{11}$, $Y_{12}$, $Y_{13}$, $Y_{14}$, and $Y_{15}$ adjoining each other together represent —O—$(CH_2)_n$—O—, wherein n is 1 or 2, substituted by one or more halogen atoms. In one embodiment, $Y_1$, $Y_2$, $Y_3$, $Y_4$, and $Y_5$, or $Y_{11}$, $Y_{12}$, $Y_{13}$, $Y_{14}$, and $Y_{15}$ each independently represent a hydrogen atom;

$C_{1-8}$ alkyloxy substituted by one or more halogen atoms which may be the same or different; or a halogen atom, provided that at least one of $Y_1$, $Y_2$, $Y_3$, $Y_4$, and $Y_5$ represents $C_{1-8}$ alkyloxy substituted by halogen atom, or two of $Y_1$, $Y_2$, $Y_3$, $Y_4$, and $Y_5$, or $Y_{11}$, $Y_{12}$, $Y_{13}$, $Y_{14}$, and $Y_{15}$ adjoining each other together represent —O—$(CH_2)_n$—O—, wherein n is 1 or 2, substituted by one or more halogen atoms.

In a preferred embodiment of the present invention, when any one of $W_1$, $W_2$, and $W_3$ represents a nitrogen atom and the remaining two groups represent the corresponding C—$Y_1$, C—$Y_2$, or C—$Y_3$, or when any one of $W_{11}$, $W_{12}$, and $W_{13}$ represents a nitrogen atom and the remaining two groups represent the corresponding C—$Y_{11}$, C—$Y_{12}$, or C—$Y_{13}$, $Y_1$, $Y_2$, $Y_3$, $Y_4$, and $Y_5$, or $Y_{11}$, $Y_{12}$, $Y_{13}$, $Y_{14}$, and $Y_{15}$ each independently represent a hydrogen atom; $C_{1-8}$ alkyl substituted by one or more halogen atoms which may be the same or different; or a halogen atom.

In a preferred embodiment of the present invention, when $W_1$, $W_2$, and $W_3$ represent C—$Y_1$, C—$Y_2$, and C—$Y_3$, respectively, and Z represents a sulfur atom, at least one of $Y_1$, $Y_2$, $Y_3$, $Y_4$, and $Y_5$ represents A. When $W_{11}$, $W_{12}$ and $W_{13}$ represent C—$Y_{11}$, C—$Y_{12}$, and C—$Y_{13}$ and Z represents an oxygen atom or a sulfur atom, preferably at least one of $Y_{11}$, $Y_{12}$, $Y_{13}$, $Y_{14}$, and $Y_{15}$ represent A.

In a preferred embodiment of the present invention, a group of preferred compounds represented by formula (I) include those wherein
$R_1$ represents
a hydrogen atom,
an alkali metal,
an alkaline earth metal,
optionally substituted $C_{1-18}$ alkyl,
$COR_4$ wherein $R_4$ represents optionally substituted $C_{1-18}$ alkyl; optionally substituted $C_{2-18}$ alkenyl; optionally substituted $C_{3-10}$ cycloalkyl; optionally substituted $C_{1-4}$ alkylthio; $OR_5$ wherein $R_5$ represents optionally substituted $C_{1-18}$ alkyl, optionally substituted $C_{2-18}$ alkenyl, or optionally substituted phenyl; or $NR_6R_7$ wherein $R_6$ and $R_7$ each independently represent a hydrogen atom or optionally substituted $C_{1-18}$ alkyl, or
$SO_2R_8$ wherein $R_8$ represents optionally substituted $C_{1-18}$ alkyl,
$R_2$ represents a hydrogen atom or optionally substituted $C_{1-4}$ alkyl,
$R_3$ represents optionally substituted $C_{1-18}$ alkyl,
alternatively $R_2$ and $R_3$ together represent —$(CH_2)_m$— wherein m is 3 or 4,
$X_1$, $X_2$, and $X_3$ each independently represent a hydrogen atom, a halogen atom, $C_{1-4}$ alkyl optionally substituted by halogen atom, $C_{1-4}$ alkyloxy optionally substituted by halogen atom, $C_{1-4}$ alkyloxycarbonyl optionally substituted by halogen atom, nitro, or cyano,
provided that $X_1$, $X_2$, and $X_3$ do not simultaneously represent a hydrogen atom, and
Z represents a bond, an oxygen atom, a sulfur atom, SO, $SO_2$, $CH_2$, $OCH_2$, $O(CH_2)_3O$, or CO.

In another preferred embodiment of the present invention, a group of preferred compounds represented by formula (I) include those wherein
$R_1$ represents
a hydrogen atom,
an alkali metal,
an alkaline earth metal,
$C_{1-18}$ alkyl optionally substituted by $C_{1-4}$ alkyloxycarbonyl or $C_{1-4}$ alkyloxy-$C_{1-4}$ alkyloxy,
$COR_4$ wherein $R_4$ represents $C_{1-18}$ alkyl optionally substituted by $C_{1-4}$ alkyloxy or acetyloxy; $C_{2-18}$ alkenyl; $C_{3-10}$ cycloalkyl; $C_{1-4}$ alkylthio; $OR_5$ wherein $R_5$ represents $C_{1-18}$ alkyl optionally substituted by halogen atom or $C_{1-4}$ alkyloxy, $C_{2-18}$ alkenyl, or phenyl; or $NR_6R_7$ wherein $R_6$ and $R_7$ each independently represent a hydrogen atom or $C_{1-18}$ alkyl, or
$SO_2R_8$ wherein $R_8$ represents $C_{1-18}$ alkyl,
$R_2$ represents a hydrogen atom or $C_{1-4}$ alkyl,
$R_3$ represents $C_{1-18}$ alkyl optionally substituted by halogen atom or acetyloxy,
alternatively $R_2$ and $R_3$ together represent —$(CH_2)_m$— wherein m is 3 or 4,
$X_1$, $X_2$, and $X_3$ each independently represent a hydrogen atom, a halogen atom, $C_{1-4}$ alkyl optionally substituted by halogen atom, $C_{1-4}$ alkyloxy, $C_{1-4}$ alkyloxycarbonyl, nitro, or cyano,
provided that $X_1$, $X_2$, and $X_3$ do not simultaneously represent a hydrogen atom, and
Z represents a bond, an oxygen atom, a sulfur atom, SO, $SO_2$, $CH_2$, $OCH_2$, $O(CH_2)_3O$, or CO.

In still another preferred embodiment of the present invention, a group of preferred compounds represented by formula (I) include those wherein
$W_1$, $W_2$, and $W_3$ represent C—$Y_1$, C—$Y_2$, and C—$Y_3$, respectively,
$Y_1$, $Y_2$, $Y_3$, $Y_4$, and $Y_5$ each independently represent a hydrogen atom, A', or B',
provided that, when Z represents a bond, methylene optionally substituted by one or two methyl, or an oxygen atom, at least one of $Y_1$, $Y_2$, $Y_3$, $Y_4$, and $Y_5$ represents A',
wherein A' represents a group selected from the group consisting of:
$C_{1-8}$ alkyl which is substituted by one or more halogen atoms which may be the same or different;
$C_{1-18}$ alkyloxy which is substituted by one or more halogen atoms which may be the same or different, and/or $C_{1-4}$ alkyloxy substituted by one or more halogen atoms which may be the same or different;
$C_{1-18}$ alkyloxycarbonyl;
$C_{1-8}$ alkylthio which is substituted by one or more halogen atoms which may be the same or different;
$C_{1-18}$ alkylsulfonyl which is subsituted by one or more halogen atoms which may be the same or different;
phenyl which is substituted by one or more halogen atoms which may be the same or different, or $C_{1-4}$ alkyl substituted by one or more halogen atoms which may be the same or different; and
phenoxy which is substituted by one or more halogen atoms which may be the same or different, or $C_{1-4}$ alkyl substituted by one or more halogen atoms which may be the same or different,
B' represents a group selected from the group consisting of a halogen atom, $C_{1-4}$ alkyl, $C_{1-4}$ alkyloxy, and cyano, alternatively adjacent two of $Y_1$, $Y_2$, $Y_3$, $Y_4$, and $Y_5$ may together represent —O—$(CH_2)_n$—O— substituted by one or more halogen atoms, wherein n is 1 or 2.

In a further preferred embodiment of the present invention, a group of preferred compounds represented by formula (I) include those
wherein
any one of $W_1$, $W_2$, and $W_3$ represents a nitrogen atom, and the other two groups represent the corresponding C—$Y_1$, C—$Y_2$, or C—$Y_3$, and
$Y_1$, $Y_2$, $Y_3$, $Y_4$, and $Y_5$ each independently represent a hydrogen atom; $C_{1-8}$ alkyl substituted by one or more halogen atoms which may be the same or different; or a halogen atom.

In a still further preferred embodiment of the present invention, a group of preferred compounds represented by formula (I) include those wherein
$R_1$ represents a hydrogen atom; or $COR_4$ wherein $R_4$ represents $C_{1-4}$ alkyl, $OR_5$ wherein $R_5$ represents $C_{1-4}$ alkyl, or $NR_6R_7$ wherein $R_6$ and $R_7$ each independently represent a hydrogen atom or $C_{1-18}$ alkyl,
$R_2$ represents $C_{1-4}$ alkyl,
$R_3$ represents $C_{1-4}$ alkyl,
alternatively $R_2$ and $R_3$ together represent —$(CH_2)_m$— wherein m is 3 or 4,
$X_1$ and $X_2$ each independently represent a hydrogen atom, a halogen atom, $C_{1-4}$ alkyl optionally substituted by halogen atom, $C_{1-4}$ alkyloxy, or $C_{1-4}$ alkyloxycarbonyl,
provided that $X_1$ and $X_2$ do not simultaneously represent a hydrogen atom,
$X_3$ represents a hydrogen atom, and
Z represents an oxygen atom, $OCH_2$, or $O(CH_2)_3O$.

In another preferred embodiment of the present invention, a group of preferred compounds represented by formula (I) include those wherein
$W_1$, $W_2$, and $W_3$ represent C—$Y_1$, C—$Y_2$, and C—$Y_3$, respectively, and $Y_1$, $Y_2$, $Y_3$, $Y_4$, and $Y_5$ each independently represent a hydrogen atom; $C_{1-8}$ alkyl which is substituted by one or more halogen atoms which may be the same or different; $C_{1-8}$ alkyloxy which is substituted by one or more halogen atoms which may be the same or different, and/or $C_{1-4}$ alkyloxy substituted by one or more halogen atoms which may be the same or different; $C_{1-8}$ alkylthio which is substituted by one or more halogen atoms which may be the same or different; or a halogen atom,
provided that at least one of $Y_1$, $Y_2$, $Y_3$, $Y_4$, and $Y_5$ represents $C_{1-8}$ alkyl which is substituted by one or more halogen atoms which may be the same or different; $C_{1-8}$ alkyloxy which is substituted by one or more halogen atoms which may be the same or different, and/or $C_{1-4}$ alkyloxy substituted by one or more halogen atoms which may be the same or different; or $C_{1-8}$ alkylthio which is substituted by one or more halogen atoms which may be the same or different,
alternatively adjacent two of $Y_1$, $Y_2$, $Y_3$, $Y_4$, and $Y_5$ may together represent —O—$(CH_2)_n$—O— substituted by one or more halogen atoms, wherein n is 1 or 2.

In still another preferred embodiment of the present invention, a group of preferred compounds represented by formula (I) include those wherein
$R_1$ represents
a hydrogen atom,
an alkali metal,
an alkaline earth metal,
optionally substituted $C_{1-18}$ alkyl,
$COR_4$ wherein $R_4$ represents optionally substituted $C_{1-18}$ alkyl; optionally substituted $C_{2-18}$ alkenyl; optionally substituted $C_{3-10}$ cycloalkyl; optionally substituted $C_{1-4}$ alkylthio; $OR_5$ wherein $R_5$ represents optionally substituted $C_{1-18}$ alkyl, optionally substituted $C_{2-18}$ alkenyl, or optionally substituted phenyl; or $NR_6R_7$ wherein $R_6$ and $R_7$ each independently represent a hydrogen atom or optionally substituted $C_{1-18}$ alkyl, or
$SO_2R_8$ wherein $R_8$ represents optionally substituted $C_{1-18}$ alkyl,
$R_2$ represents a hydrogen atom or optionally substituted $C_{1-4}$ alkyl,
$R_3$ represents optionally substituted $C_{1-18}$ alkyl,
alternatively $R_2$ and $R_3$ together represent —$(CH_2)_m$— wherein m is 3 or 4,
$X_1$, $X_2$, and $X_3$ each independently represent a hydrogen atom, a halogen atom, $C_{1-4}$ alkyl optionally substituted by halogen atom, $C_{1-4}$ alkyloxy optionally substituted by halogen atom, $C_{1-4}$ alkyloxycarbonyl optionally substituted by halogen atom, nitro, or cyano,
provided that $X_1$, $X_2$, and $X_3$ do not simultaneously represent a hydrogen atom, and
$W_1$, $W_2$, and $W_3$ represent C—$Y_1$, C—$Y_2$, and C—$Y_3$, respectively,
$Y_1$, $Y_2$, $Y_3$, $Y_4$, and $Y_5$ each independently represent a hydrogen atom, A', or B',
provided that, when Z represents a bond, methylene optionally substituted by one or two methyl, or an oxygen atom, at least one of $Y_1$, $Y_2$, $Y_3$, $Y_4$, and $Y_5$ represents A',
wherein A' represents a group selected from the group consisting of:
$C_{1-8}$ alkyl which is substituted by one or more halogen atoms which may be the same or different;
$C_{1-8}$ alkyloxy which is substituted by one or more halogen atoms which may be the same or different, and/or $C_{1-4}$ alkyloxy substituted by one or more halogen atoms which may be the same or different;
$C_{1-8}$ alkyloxycarbonyl;
$C_{1-8}$ alkylthio which is substituted by one or more halogen atoms which may be the same or different;
$C_{1-8}$ alkylsulfonyl which is subsituted by one or more halogen atoms which may be the same or different;
phenyl which is substituted by one or more halogen atoms which may be the same or different, or $C_{1-4}$ alkyl substituted by one or more halogen atoms which may be the same or different; and
phenoxy which is substituted by one or more halogen atoms which may be the same or different, or $C_{1-4}$ alkyl substituted by one or more halogen atoms which may be the same or different,
B' represents a group selected from the group consisting of a halogen atom, $C_{1-4}$ alkyl, $C_{1-4}$ alkyloxy, and cyano,
alternatively adjacent two of $Y_1$, $Y_2$, $Y_3$, $Y_4$, and $Y_5$ may together represent —O—$(CH_2)_n$—O— substituted by one or more halogen atoms, wherein n is 1 or 2, and
Z represents a bond, an oxygen atom, a sulfur atom, SO, $SO_2$, $CH_2$, $OCH_2$, $O(CH_2)_3O$, or CO.

In a further preferred embodiment of the present invention, a group of preferred compounds represented by formula (I) include those wherein
$R_1$ represents
a hydrogen atom,
an alkali metal,
an alkaline earth metal,
optionally substituted $C_{1-18}$ alkyl,
$COR_4$ wherein $R_4$ represents optionally substituted $C_{1-18}$ alkyl; optionally substituted $C_{2-18}$ alkenyl; optionally substituted $C_{3-10}$ cycloalkyl; optionally substituted $C_{1-4}$ alkylthio; $OR_5$ wherein $R_5$ represents optionally substituted $C_{1-18}$ alkyl, optionally substituted $C_{2-18}$ alkenyl, or optionally substituted phenyl; or $NR_6R_7$ wherein $R_6$ and $R_7$ each independently represent a hydrogen atom or optionally substituted $C_{1-18}$ alkyl, or
$SO_2R_8$ wherein $R_8$ represents optionally substituted $C_{1-18}$ alkyl,
$R_2$ represents a hydrogen atom or optionally substituted $C_{1-4}$ alkyl,
$R_3$ represents optionally substituted $C_{1-18}$ alkyl, alternatively $R_2$ and $R_3$ together represent —$(CH_2)_m$— wherein m is 3 or 4,
$X_1$, $X_2$, and $X_3$ each independently represent a hydrogen atom, a halogen atom, $C_{1-4}$ alkyl optionally substituted by halogen atom, $C_{1-4}$ alkyloxy optionally substituted by halogen atom, $C_{1-4}$ alkyloxycarbonyl optionally substituted by halogen atom, nitro, or cyano, provided that $X_1$, $X_2$, and $X_3$ do not simultaneously represent a hydrogen atom, and any one of $W_1$, $W_2$, and $W_3$ represents a nitrogen atom, and the other two groups represent the corresponding $C—Y_1$, $C—Y_2$, or $C—Y_3$, and $Y_1, Y_2, Y_3, Y_4$, and $Y_5$ each independently represent a hydrogen atom; $C_{1-8}$ alkyl substituted by one or more halogen atoms which may be the same or different; or a halogen atom, and Z represents a bond, an oxygen atom, a sulfur atom, SO, $SO_2$, $CH_2$, $OCH_2$, $O(CH_2)_3O$, or CO.

In a still further preferred embodiment of the present invention, a group of preferred compounds represented by formula (I) include those wherein $R_1$ represents a hydrogen atom; or $COR_4$ wherein $R_4$ represents $C_{1-4}$ alkyl, $OR_5$ wherein $R_5$ represents $C_{1-4}$ alkyl, or $NR_6R_7$ wherein $R_6$ and $R_7$ each independently represent a hydrogen atom or $C_{1-18}$ alkyl, $R_2$ represents $C_{1-4}$ alkyl, $R_3$ represents $C_{1-4}$ alkyl, alternatively $R_2$ and $R_3$ together represent $—(CH_2)_m—$ wherein m is 3 or 4, $X_1$ and $X_2$ each independently represent a hydrogen atom, a halogen atom, $C_{1-4}$ alkyl optionally substituted by halogen atom, $C_{1-4}$ alkyloxy, or $C_{1-4}$ alkyloxycarbonyl, provided that $X_1$ and $X_2$ do not simultaneously represent a hydrogen atom, $X_3$ represents a hydrogen atom, $W_1$, $W_2$, and $W_3$ represent $C—Y_1$, $C—Y_2$, and $C—Y_3$, respectively, $Y_1, Y_2, Y_3, Y_4$, and $Y_5$ each independently represent a hydrogen atom; $C_{1-8}$ alkyl which is substituted by one or more halogen atoms which may be the same or different; $C_{1-8}$ alkyloxy which is substituted by one or more halogen atoms which may be the same or different, and/or $C_{1-4}$ alkyloxy substituted by one or more halogen atoms which may be the same or different; $C_{1-8}$ alkylthio which is substituted by one or more halogen atoms which may be the same or different; or a halogen atom, provided that at least one of $Y_1, Y_2, Y_3, Y_4$, and $Y_5$ represents $C_{1-8}$ alkyl which is substituted by one or more halogen atoms which may be the same or different; $C_{1-8}$ alkyloxy which is substituted by one or more halogen atoms which may be the same or different, and/or $C_{1-4}$ alkyloxy substituted by one or more halogen atoms which may be the same or different; or $C_{1-8}$ alkylthio which is substituted by one or more halogen atoms which may be the same or different, alternatively adjacent two of $Y_1, Y_2, Y_3, Y_4$, and $Y_5$ may together represent $—O—(CH_2)_n—O—$ substituted by one or more halogen atoms, wherein n is 1 or 2, and Z represents an oxygen atom, $OCH_2$, or $O(CH_2)_3O$.

In another preferred embodiment of the present invention, a group of preferred compounds represented by formula (I) include those wherein $R_1$ represents $COR_4'$ or $COOR_5$ wherein $R_4'$ and $R_5$ represent $C_{1-4}$ alkyl, $R_2$ represents $C_{1-4}$ alkyl, $R_3$ represents $C_{1-4}$ alkyl, $X_1$ and $X_2$ each independently represent a hydrogen atom, or $C_{1-4}$ alkyl optionally substituted by halogen atom, provided that $X_1$ and $X_2$ do not simultaneously represent a hydrogen atom, $X_3$ represents a hydrogen atom, $W_1$, $W_2$, and $W_3$ represent $C—Y_1$, $C—Y_2$, and $C—Y_3$, respectively, $Y_1, Y_2, Y_3, Y_4$, and $Y_5$ each independently represent a hydrogen atom; $C_{1-8}$ alkyloxy which is substituted by one or more halogen atoms which may be the same or different, and/or $C_{1-4}$ alkyloxy substituted by one or more halogen atoms which may be the same or different; or a halogen atom, provided that at least one of $Y_1, Y_2, Y_3, Y_4$, and $Y_5$ represents $C_{1-8}$ alkyloxy which is substituted by one or more halogen atoms which may be the same or different, and/or $C_{1-4}$ alkyloxy substituted by one or more halogen atoms which may be the same or different, alternatively adjacent two of $Y_1, Y_2, Y_3, Y_4$, and $Y_5$ may together represent $—O—(CH_2)_n—O—$ substituted by one or more halogen atoms, wherein n is 1 or 2, and Z represents an oxygen atom.

Further, in a preferred embodiment of the present invention, a group of compounds of formula (I) wherein $W_1$, $W_2$, and $W_3$ represent $C—Y_1$, $C—Y_2$, and $C—Y_3$, respectively, include compounds of formula (II) or agriculturally and horticulturally acceptable acid addition salts thereof:

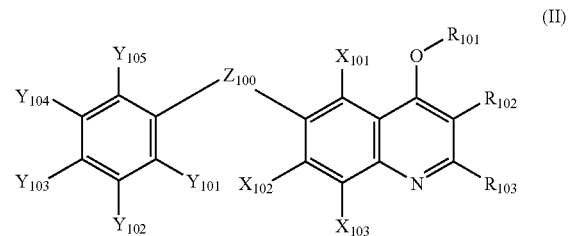

(II)

wherein $R_{101}$ represents
a hydrogen atom,
an alkali metal,
an alkaline earth metal, or
$COR_{104}$ wherein $R_{104}$ represents
optionally substituted $C_{1-18}$ alkyl,
optionally substituted $C_{2-18}$ alkenyl,
optionally substituted $C_{2-18}$ alkynyl,
optionally substituted $C_{3-10}$ cycloalkyl,
optionally substituted phenyl lower alkyl,
optionally substituted phenoxy lower alkyl,
optionally substituted phenyl,
optionally substituted heterocyclic group,
$C_{1-4}$ alkylthio,
$OR_{105}$ wherein $R_{105}$ represents
optionally substituted $C_{1-18}$ alkyl,
optionally substituted $C_{2-18}$ alkenyl,
optionally substituted $C_{2-18}$ alkynyl,
optionally substituted $C_{3-10}$ cycloalkyl,
optionally substituted phenyl lower alkyl,
optionally substituted phenoxy lower alkyl,
optionally substituted phenyl, or
optionally substituted heterocyclic group, or
$NR_{106}R_{107}$ wherein $R_{106}$ and $R_{107}$ each independently represents
a hydrogen atom,
optionally substituted $C_{1-18}$ alkyl, or
optionally substituted phenyl, $R_{102}$ represents a hydrogen atom or optionally substituted $C_{1-4}$ alkyl, $R_{103}$ represents
a hydrogen atom,
optionally substituted $C_{1-18}$ alkyl, optionally substituted $C_{2-4}$ alkenyl,
or optionally substituted $C_{1-4}$ alkoxy,
wherein, in $R_{101}$, $R_{102}$, and $R_{103}$, the substituent in each of the optionally substituted groups is selected from the group consisting of halogen atom; $C_{1-4}$ alkyloxy; nitro; cyano; formyl; trifluoromethyl; trifluoromethoxy; acetyl; acetyloxy; $C_{1-4}$ alkyl, provided that this $C_{1-4}$ alkyl is not a substituent for the alkyl group; and $C_{3-6}$ cycloalkyl optionally substituted by halogen atom,
alternatively $R_{102}$ and $R_{103}$ together represent —$(CH_2)_m$— wherein m is 3 or 4,
$X_{101}$, $X_{102}$, and $X_{103}$ each independently represent
a hydrogen atom,
a halogen atom,
$C_{1-4}$ alkyl optionally substituted by halogen atom,
$C_{1-4}$ alkyloxy optionally substituted by halogen atom,
$C_{1-4}$ alkylthio optionally substituted by halogen atom,
nitro, or
cyano,
provided that $X_{101}$, $X_{102}$, and $X_{103}$ do not simultaneously represent a hydrogen atom,
$Y101$, $Y_{102}$, $Y_{103}$, $Y_{104}$, and $Y_{105}$ each independently represent a hydrogen atom, $A_{100}$, or $B_{100}$,
provided that, when $Z_{100}$ represents an oxygen atom, at least one of $Y_{101}$, $Y_{102}$, $Y_{103}$, $Y_{104}$, and $Y_{105}$ represents $A_{100}$, wherein $A_{100}$ represents a group selected from the group consisting of:
$C_{1-8}$ alkyl which is substituted by one or more halogen atoms which may be the same or different or $C_{1-4}$ alkyloxy substituted by one or more halogen atoms which may be the same or different;
$C_{1-8}$ alkyloxy which is substituted by one or more halogen atoms which may be the same or different or $C_{1-4}$ alkyloxy substituted by one or more halogen atoms which may be the same or different;
$C_{1-8}$ alkylthio which is optionally substituted by one or more halogen atoms which may be the same or different or $C_{1-4}$ alkyloxy substituted by one or more halogen atoms which may be the same or different;
$C_{1-8}$ alkylsulfinyl which is optionally substituted by one or more halogen atoms which may be the same or different or $C_{1-4}$ alkyloxy substituted by one or more halogen atoms which may be the same or different;
$C_{1-8}$ alkylsulfonyl which is optionally substituted by one or more halogen atoms which may be the same or different or $C_{1-4}$ alkyloxy substituted by one or more halogen atoms which may be the same or different;
phenyl which is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different; and
phenoxy which is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different,
$B_{100}$ represents a group selected from the group consisting of a halogen atom, $C_{1-4}$ alkyl, $C_{1-4}$ alkyloxy, nitro, and cyano,
alternatively adjacent two of $Y_{101}$, $Y_{102}$, $Y_{103}$, $Y_{104}$, and $Y_{105}$ may together represent —O—$(CH_2)_n$—O— optionally substituted by halogen atom, wherein n is 1 or 2, and
$Z_{100}$ represents an oxygen atom, a sulfur atom, SO, $SO_2$, $OCH_2$, CO, or $CH_2$.

In a preferred embodiment of the present invention, a group of preferred compounds represented by formula (II) include those wherein $R_{101}$ represents
a hydrogen atom,
an alkali metal,
an alkaline earth metal, or
$COR_{104}$ wherein $R_{104}$ represents optionally substituted $C_{1-18}$ alkyl; optionally substituted $C_{2-18}$ alkenyl; $C_{1-4}$ alkylthio; or $OR_{105}$ in which $R_{105}$ is optionally substituted $C_{1-18}$ alkyl, optionally substituted $C_{2-18}$ alkenyl, or optionally substituted phenyl,
$R_{102}$ represents a hydrogen atom or optionally substituted $C_{1-4}$ alkyl,
$R_{103}$ represents optionally substituted $C_{1-18}$ alkyl, alternatively $R_{102}$ and $R_{103}$ together represent —$(CH_2)_m$— wherein m is 3 or 4, and
$X_{101}$, $X_{102}$, and $X_{103}$ each independently represent a hydrogen atom, a halogen atom, $C_{1-4}$ alkyl optionally substituted by halogen atom, $C_{1-4}$ alkyloxy optionally substituted by halogen atom, nitro, or cyano,
provided that $X_{101}$, $X_{102}$, and $X_{103}$ do not simultaneously represent a hydrogen atom.

In another preferred embodiment of the present invention, a group of preferred compounds represented by formula (II) include those wherein
$R_{101}$ represents
a hydrogen atom,
an alkali metal,
an alkaline earth metal, or
$COR_{104}$ wherein $R_{104}$ represents $C_{1-18}$ alkyl; $C_{2-18}$ alkenyl; $C_{1-4}$ alkylthio; or $OR_{105}$ in which $R_{105}$ represents $C_{1-18}$ alkyl optionally substituted by halogen atom or $C_{1-4}$ alkyloxy; $C_{2-18}$ alkenyl; or phenyl,
$R_{102}$ represents a hydrogen atom or $C_{1-4}$ alkyl,
$R_{103}$ represents $C_{1-18}$ alkyl optionally substituted by halogen atom or acetyloxy,
alternatively $R_{102}$ and $R_{103}$ together represent —$(CH_2)_m$— wherein m is 3 or 4,
$X_{101}$, $X_{102}$, and $X_{103}$ each independently represent a hydrogen atom, a halogen atom, $C_{1-4}$ alkyl optionally substituted by halogen atom, $C_{1-4}$ alkyloxy, nitro, or cyano,
provided that $X_{101}$, $X_{102}$, and $X_{103}$ do not simultaneously represent a hydrogen atom.

In another preferred embodiment of the present invention, a group of preferred compounds represented by formula (II) include those wherein
$Y_{101}$, $Y_{102}$, $Y_{103}$, $Y_{104}$, and $Y_{105}$ each independently represent a hydrogen atom, $A_{100}'$ or $B_{100}'$,
provided that, when $Z_{100}$ represents an oxygen atom, at least one of $Y_{101}$, $Y_{102}$, $Y_{103}$, $Y_{104}$, and $Y_{105}$ represents $A_{100}'$,
wherein $A_{100}'$ represents a group selected from the group consisting of:
$C_{1-8}$ alkyl which is substituted by one or more halogen atoms which may be the same or different;
$C_{1-8}$ alkyloxy which is substituted by one or more halogen atoms which may be the same or different;
$C_{1-8}$ alkylthio which is substituted by one or more halogen atoms which may be the same or different;
$C_{1-8}$ alkylsulfonyl which is substituted by one or more halogen atoms which may be the same or different;
phenyl which is substituted by one or more halogen atoms which may be the same or different, or $C_{1-4}$ alkyl substituted by one or more halogen atoms which may be the same or different; and
phenoxy which is substituted by one or more halogen atoms which may be the same or different, or $C_{1-4}$ alkyl substituted by one or more halogen atoms which may be the same or different, $B_{100}'$ represents a group selected from the group consisting of a halogen atom, $C_{1-4}$ alkyl, $C_{1-4}$ alkyloxy, and cyano, alternatively adjacent two of $Y_{101}$, $Y_{102}$, $Y_{103}$, $Y_{104}$, and $Y_{105}$ may together represent —O—$(CH_2)_n$—O— substituted by one or more halogen atoms, wherein n is 1 or 2.

In another preferred embodiment of the present invention, a group of preferred compounds represented by formula (II) include those wherein $R_{101}$ represents a hydrogen atom; or $COR_{104}$ wherein $R_{104}$ represents $C_{1-4}$ alkyl or $OR_{105}$ wherein $R_{105}$ represents $C_{1-4}$ alkyl, $R_{102}$ represents $C_{1-4}$ alkyl, $R_{103}$ represents $C_{1-4}$ alkyl, alternatively $R_{102}$ and $R_{103}$ together represents —$(CH_2)_m$— wherein m is 3 or 4, $X_{101}$ and $X_{102}$ each independently represent a hydrogen atom, or $C_{1-4}$ alkyl optionally substituted by halogen atom, provided that they do not simultaneously represent a hydrogen atom, $X_{103}$ represents a hydrogen atom, and $Z_{100}$ represents an oxygen atom.

In another preferred embodiment of the present invention, a group of preferred compounds represented by formula (II) include those wherein $Y_{101}$, $Y_{102}$, $Y_{103}$, $Y_{104}$, and $Y_{105}$ each independently represent a hydrogen atom; or $C_{1-18}$ alkyloxy which is substituted by one or more halogen atoms which may be the same or different, or a halogen atom, provided that at least one of $Y_{101}$, $Y_{102}$, $Y_{103}$, $Y_{104}$, and $Y_{105}$ represents $C_{1-4}$ alkyloxy in which the $C_{1-8}$ alkyloxy group is substituted by one or more halogen atoms which may be the same or different, alternatively adjacent two of $Y_{101}$, $Y_{102}$, $Y_{103}$, $Y_{104}$, and $Y_{105}$ may together represent —O—$(CH_2)_n$—O— substituted by one or more halogen atoms, wherein n is 1 or 2.

In a further preferred embodiment of the present invention, a group of preferred compounds represented by formula (II) include those wherein $R_{101}$ represents a hydrogen atom, an alkali metal, an alkaline earth metal, or $COR_{104}$ wherein $R_{104}$ represents optionally substituted $C_{1-18}$ alkyl; optionally substituted $C_{2-18}$ alkenyl; $C_{1-4}$ alkylthio; or $OR_{105}$ wherein $R_{105}$ represents optionally substituted $C_{1-18}$ alkyl, optionally substituted $C_{2-18}$ alkenyl, or optionally substituted phenyl, $R_{102}$ represents a hydrogen atom or optionally substituted $C_{1-4}$ alkyl, and $R_{103}$ represents optionally substituted $C_{1-18}$ alkyl, alternatively $R_{102}$ and $R_{103}$ together represent —$(CH_2)_m$— wherein m is 3 or 4, $X_{101}$, $X_{102}$, and $X_{103}$ each independently represent a hydrogen atom, a halogen atom, $C_{1-4}$ alkyl optionally substituted by halogen atom, $C_{1-4}$ alkyloxy optionally substituted by halogen atom, nitro, or cyano, provided that $X_{101}$, $X_{102}$, and $X_{103}$ do not simultaneously represent a hydrogen atom, $Y_{101}$, $Y_{102}$, $Y_{103}$, $Y_{104}$, and $Y_{105}$ each independently represent a hydrogen atom, $A_{100}'$ or $B_{100}'$, provided that, when $Z_{100}$ represents an oxygen atom, at least one of $Y_{101}$, $Y_{102}$, $Y_{103}$, $Y_{104}$, and $Y_{105}$ represents $A_{100}'$, wherein $A_{100}'$ represents a group selected from the group consisting of:

$C_{1-8}$ alkyl which is optionally substituted by one or more halogen atoms which may be the same or different;

$C_{1-8}$ alkyloxy which is substituted by one or more halogen atoms which may be the same or different;

$C_{1-8}$ alkylthio which is optionally substituted by one or more halogen atoms which may be the same or different;

$C_{1-8}$ alkylsulfonyl which is substituted by one or more halogen atoms which may be the same or different;

phenyl which is substituted by one or more halogen atoms which may be the same or different, or $C_{1-4}$ alkyl substituted by one or more halogen atoms which may be the same or different; and phenoxy which is substituted by one or more halogen atoms which may be the same or different, or $C_{1-4}$ alkyl substituted by one or more halogen atoms which may be the same or different, $B_{100}'$ represents a group selected from the group consisting of a halogen atom, $C_{1-4}$ alkyl, $C_{1-4}$ alkyloxy, and cyano, alternatively adjacent two of $Y_{101}$, $Y_{102}$, $Y_{103}$, $Y_{104}$, and $Y_{105}$ may together represent —O—$(CH_2)_n$—O— substituted by one or more halogen atoms, wherein n is 1 or 2.

Further, in a still further preferred embodiment of the present invention, a group of preferred compounds represented by formula (II) include those wherein $R_{101}$ represents a hydrogen atom; or $COR_{104}$ wherein $R_{104}$ represents $C_{1-4}$ alkyl, or $OR_{105}$ wherein $R_{105}$ represents $C_{1-4}$ alkyl, $R_{102}$ represents $C_{1-4}$ alkyl, $R_{103}$ represents $C_{1-4}$ alkyl, alternatively $R_{102}$ and $R_{103}$ together represent —$(CH_2)_m$— wherein m is 3 or 4, $X_{101}$ and $X_{102}$ each independently represent a hydrogen atom, or $C_{1-4}$ alkyl optionally substituted by halogen atom, provided that they do not simultaneously represent a hydrogen atom, $X_{103}$ represents a hydrogen atom, $Z_{100}$ represents an oxygen atom, and $Y_{101}$, $Y_{102}$, $Y_{103}$, $Y_{104}$, and $Y_{105}$ each independently represent a hydrogen atom; $C_{1-8}$ alkyloxy substituted by one or more halogen atoms which may be the same or different; or a halogen atom, provided that at least one of $Y_{101}$, $Y_{102}$, $Y_{103}$, $Y_{104}$, and $Y_{105}$ represents $C_{1-4}$ alkyloxy in which the $C_{1-8}$ alkyloxy is substituted by one or more halogen atoms which may be the same or different, alternatively adjacent two of $Y_{101}$, $Y_{102}$, $Y_{103}$, $Y_{104}$, and $Y_{105}$ may together represent —O—$(CH_2)_n$—O— substituted by one or more halogen atoms, wherein n is 1 or 2.

Further, in a preferred embodiment of the present invention, a group of compounds represented by formula (Ia) wherein $W_{11}$, $W_{12}$, and $W_{13}$ represent C—$Y_{11}$, C—$Y_{12}$, and C—$Y_{13}$, respectively, include compounds represented by formula (IIa) or agriculturally and horticulturally acceptable acid addition salt thereof:

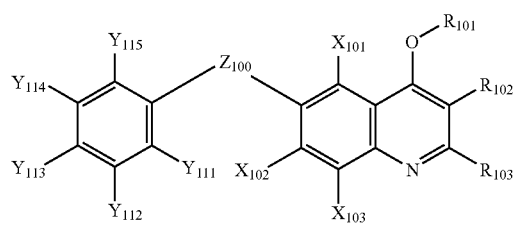

(IIa)

wherein
$R_{101}$ represents
  a hydrogen atom,
  an alkali metal,
  an alkaline earth metal, or
  $COR_{104}$ wherein $R_{104}$ represents
    optionally substituted $C_{1-18}$ alkyl,
    optionally substituted $C_{2-18}$ alkenyl,
    optionally substituted $C_{2-18}$ alkynyl,
    optionally substituted $C_{3-10}$ cycloalkyl,
    optionally substituted phenyl lower alkyl,
    optionally substituted phenoxy lower alkyl,
    optionally substituted phenyl,
    optionally substituted heterocyclic group,
    $C_{1-4}$ alkylthio,
  $OR_{105}$ wherein $R_{105}$ represents
    optionally substituted $C_{1-18}$ alkyl,
    optionally substituted $C_{2-18}$ alkenyl,
    optionally substituted $C_{2-18}$ alkynyl,
    optionally substituted $C_{3-10}$ cycloalkyl,
    optionally substituted phenyl lower alkyl,
    optionally substituted phenoxy lower alkyl,
    optionally substituted phenyl, or
    optionally substituted heterocyclic group, or
  $NR_{106}R_{107}$ wherein $R_{106}$ and $R_{107}$ each independently represent a hydrogen atom, optionally substituted $C_{1-18}$ alkyl, or optionally substituted phenyl,
$R_{102}$ represents a hydrogen atom, or optionally substituted $C_{1-4}$ alkyl,
$R_{103}$ represents
  a hydrogen atom,
  optionally substituted $C_{1-18}$ alkyl,
  optionally substituted $C_{2-4}$ alkenyl,
  or optionally substituted $C_{1-4}$ alkoxy,
  wherein, in $R_{101}$, $R_{102}$, and $R_{103}$, the substituent in each of the optionally substituted groups is selected from the group consisting of halogen atom; $C_{1-4}$ alkyloxy; nitro; cyano; formyl; trifluoromethyl; trifluoromethoxy; acetyl; acetyloxy; $C_{1-4}$ alkyl, provided that this $C_{1-4}$ alkyl is not a substituent for the alkyl group; and $C_{3-6}$ cycloalkyl optionally substituted by halogen atom,
  alternatively $R_{102}$ and $R_{103}$ together represent —$(CH_2)_m$— wherein m is 3 or 4,
$X_{101}$, $X_{102}$, and $X_{103}$ each independently represent a hydrogen atom, a halogen atom, $C_{1-4}$ alkyl optionally substituted by halogen atom, $C_{1-4}$ alkyloxy optionally substituted by halogen atom, $C_{1-4}$ alkylthio optionally substituted by halogen atom, nitro, or cyano, provided that $X_{101}$, $X_{102}$, and $X_{103}$ do not simultaneously represent a hydrogen atom,
$Y_{111}$, $Y_{112}$, $Y_{113}$, $Y_{114}$, and $Y_{115}$ each independently represent a hydrogen atom, $A_{100}$, or $B_{100}$,
  wherein $A_{100}$ represents a group selected from the group consisting of:
    $C_{1-8}$ alkyl which is substituted by one or more halogen atoms which may be the same or different, or $C_{1-4}$ alkyloxy substituted by one or more halogen atoms which may be the same or different;
    $C_{1-8}$ alkyloxy which is substituted by one or more halogen atoms which may be the same or different, or $C_{1-4}$ alkyloxy substituted by one or more halogen atoms which may be the same or different;
    $C_{1-8}$ alkylthio which is optionally substituted by one or more halogen atoms which may be the same or different, or $C_{1-4}$ alkyloxy substituted by one or more halogen atoms which may be the same or different;
    $C_{1-8}$ alkylsulfinyl which is optionally substituted by one or more halogen atoms which may be the same or different, or $C_{1-4}$ alkyloxy substituted by one or more halogen atoms which may be the same or different;
    $C_{1-8}$ alkylsulfonyl which is optionally substituted by one or more halogen atoms which may be the same or different, or $C_{1-4}$ alkyloxy substituted by one or more halogen atoms which may be the same or different;
    phenyl which is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different; and
    phenoxy which is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different,
  $B_{100}$ represents a group selected from the group consisting of a halogen atom, $C_{1-4}$ alkyl, $C_{1-4}$ alkyloxy, nitro, and cyano,
  alternatively adjacent two of $Y_{111}$, $Y_{112}$, $Y_{113}$, $Y_{114}$, and $Y_{115}$ may together represent —O—$(CH_2)_n$—O— optionally substituted by halogen atom, wherein n is 1 or 2, and
$Z_{100}$ represents an oxygen atom, a sulfur atom, SO, $SO_2$, $OCH_2$, CO, or $CH_2$.

Further, specific examples of compounds of formula (I) or formula (Ia) include compounds shown in Tables 1 to 14 below.

TABLE 1

| Compound No. | R1 | R2 | R3 | X1 | X2 | X3 | Z | W1 | | W2 | | W3 | | Y4 | Y5 |
|---|---|---|---|---|---|---|---|---|---|---|---|---|---|---|---|
| | | | | | | | | Y1 | | Y2 | | Y3 | | | |
| 1 | H | Me | Me | Cl | H | H | O | C | H | C | H | C | Cl | H | H |
| 2 | Ac | Me | Me | Cl | H | H | O | C | H | C | H | C | Cl | H | H |
| 3 | COOMe | Me | Me | Cl | H | H | O | C | H | C | H | C | Cl | H | H |
| 4 | COtBu | Me | Me | Cl | H | H | O | C | H | C | H | C | Cl | H | H |
| 5 | Ac | Et | Me | Cl | H | H | O | C | H | C | H | C | Cl | H | H |
| 6 | Ac | Bu | Me | Cl | H | H | O | C | H | C | H | C | Cl | H | H |
| 7 | Ac | H | Me | Cl | H | H | O | C | H | C | H | C | Cl | H | H |
| 8 | Ac | Me | Et | Cl | H | H | O | C | H | C | H | C | Cl | H | H |
| 9 | COOMe | Me | Et | Cl | H | H | O | C | H | C | H | C | Cl | H | H |
| 10 | Ac | H | I—Pr | Cl | H | H | O | C | H | C | H | C | Cl | H | H |
| 11 | Ac | Me | Bu | Cl | H | H | O | C | H | C | H | C | Cl | H | H |
| 12 | Ac | H | CF3 | Cl | H | H | O | C | H | C | H | C | Cl | H | H |
| 13 | Ac | Me | CH2—OAc | Cl | H | H | O | C | H | C | H | C | Cl | H | H |
| 14 | Ac | Me | Me | CN | H | H | O | C | H | C | H | C | Cl | H | H |

TABLE 1-continued

| Compound No. | R1 | R2 | R3 | X1 | X2 | X3 | Z | W1 Y1 | | W2 Y2 | | W3 Y3 | | Y4 | Y5 |
|---|---|---|---|---|---|---|---|---|---|---|---|---|---|---|---|
| 15 | Ac | Me | Me | F | H | H | O | C | H | C | H | C | Cl | H | H |
| 16 | Ac | Me | Me | Me | H | H | O | C | H | C | H | C | Cl | H | H |
| 17 | COOMe | Me | Et | Me | H | H | O | C | H | C | H | C | Cl | H | H |
| 18 | H | Me | Me | CF3 | H | H | O | C | H | C | H | C | Cl | H | H |
| 19 | Ac | Me | Me | CF3 | H | H | O | C | H | C | H | C | Cl | H | H |
| 20 | COOMe | Me | Et | CF3 | H | H | O | C | H | C | H | C | Cl | H | H |
| 21 | Ac | Me | Me | H | CF3 | H | O | C | H | C | H | C | Cl | H | H |
| 22 | Ac | Me | Me | H | Cl | H | O | C | H | C | H | C | Cl | H | H |
| 23 | COOMe | Me | Me | H | Cl | H | O | C | H | C | H | C | Cl | H | H |
| 24 | COtBu | Me | Me | H | Cl | H | O | C | H | C | H | C | Cl | H | H |
| 25 | Ac | Et | Me | H | Cl | H | O | C | H | C | H | C | Cl | H | H |
| 26 | Ac | Bu | Me | H | Cl | H | O | C | H | C | H | C | Cl | H | H |
| 27 | Ac | H | Me | H | Cl | H | O | C | H | C | H | C | Cl | H | H |
| 28 | Ac | Me | Et | H | Cl | H | O | C | H | C | H | C | Cl | H | H |
| 29 | Ac | H | I—Pr | H | Cl | H | O | C | H | C | H | C | Cl | H | H |
| 30 | Ac | Me | Bu | H | Cl | H | O | C | H | C | H | C | Cl | H | H |
| 31 | Ac | Me | Me | H | F | H | O | C | H | C | H | C | Cl | H | H |
| 32 | Ac | Me | Me | H | Me | H | O | C | H | C | H | C | Cl | H | H |
| 33 | COOMe | Me | Et | H | Me | H | O | C | H | C | H | C | Cl | H | H |
| 34 | Ac | Me | Me | H | OMe | H | O | C | H | C | H | C | Cl | H | H |
| 35 | Ac | Me | Me | H | H | CF3 | O | C | H | C | H | C | Cl | H | H |
| 36 | Ac | Me | Me | Me | Me | H | O | C | H | C | H | C | Cl | H | H |
| 37 | COOMe | Me | Et | Me | Me | H | O | C | H | C | H | C | Cl | H | H |
| 38 | Ac | Me | I—Pr | Cl | H | H | O | C | H | C | H | C | Cl | H | H |
| 39 | Ac | Me | Me | NO2 | H | H | O | C | H | C | H | C | Cl | H | H |
| 40 | Ac | Me | Me | Cl | H | H | O | C | H | C | Cl | C | H | H | H |
| 41 | Ac | Me | Me | H | Cl | H | O | C | H | C | Cl | C | H | H | H |
| 42 | Ac | Me | Me | Cl | H | H | O | C | Cl | C | H | C | H | H | H |
| 43 | Ac | Me | Me | H | Cl | H | O | C | Cl | C | H | C | H | H | H |
| 44 | Ac | Me | Me | Cl | H | H | O | C | H | C | H | C | CN | H | H |
| 45 | Ac | Me | Me | H | Cl | H | O | C | H | C | H | C | CN | H | H |
| 46 | Ac | Me | Me | Cl | H | H | O | C | H | C | H | C | F | H | H |
| 47 | Ac | Me | Me | H | Cl | H | O | C | H | C | H | C | F | H | H |
| 48 | Ac | Me | Me | Cl | H | H | O | C | H | C | H | C | Me | H | H |
| 49 | Ac | Me | Me | H | Cl | H | O | C | H | C | H | C | Me | H | H |
| 50 | Ac | Me | Me | Cl | H | H | O | C | H | C | H | C | OMe | H | H |
| 51 | Ac | Me | Me | H | Cl | H | O | C | H | C | H | C | OMe | H | H |

TABLE 2

| Compound No. | R1 | R2 | R3 | X1 | X2 | X3 | Z | W1 Y1 | | W2 Y2 | | W3 Y3 | | Y4 | Y5 |
|---|---|---|---|---|---|---|---|---|---|---|---|---|---|---|---|
| 52 | Ac | Me | Me | Cl | H | H | O | C | H | C | OMe | C | H | H | H |
| 53 | Ac | Me | Me | H | Cl | H | O | C | H | C | OMe | C | H | H | H |
| 54 | Ac | Me | Me | Cl | H | H | O | C | OMe | C | H | C | H | H | H |
| 55 | Ac | Me | Me | H | Cl | H | O | C | OMe | C | H | C | H | H | H |
| 56 | Ac | Me | Me | Cl | H | H | O | C | H | C | H | C | CF3 | H | H |
| 57 | COOMe | Me | Et | Cl | H | H | O | C | H | C | H | C | CF3 | H | H |
| 58 | Ac | Me | Me | Me | H | H | O | C | H | C | H | C | CF3 | H | H |
| 59 | Ac | Me | Et | Me | H | H | O | C | H | C | H | C | CF3 | H | H |
| 60 | COOMe | Me | Et | Me | H | H | O | C | H | C | H | C | CF3 | H | H |
| 61 | Ac | Me | Me | CF3 | H | H | O | C | H | C | H | C | CF3 | H | H |
| 62 | Ac | Me | Et | CF3 | H | H | O | C | H | C | H | C | CF3 | H | H |
| 63 | COOMe | Me | Et | CF3 | H | H | O | C | H | C | H | C | CF3 | H | H |
| 64 | Ac | Me | Me | H | Cl | H | O | C | H | C | H | C | CF3 | H | H |
| 65 | Ac | Me | Me | H | Me | H | O | C | H | C | H | C | CF3 | H | H |
| 66 | Ac | Me | Et | H | Me | H | O | C | H | C | H | C | CF3 | H | H |
| 67 | COOMe | Me | Et | H | Me | H | O | C | H | C | H | C | CF3 | H | H |
| 68 | Ac | Me | Me | H | CF3 | H | O | C | H | C | H | C | CF3 | H | H |
| 69 | Ac | Me | Me | Me | Me | H | O | C | H | C | H | C | CF3 | H | H |
| 70 | Ac | Me | Et | Me | Me | H | O | C | H | C | H | C | CF3 | H | H |
| 71 | COOMe | Me | Et | Me | Me | H | O | C | H | C | H | C | CF3 | H | H |
| 72 | Ac | Me | Me | Cl | H | H | O | C | H | C | CF3 | C | H | H | H |
| 73 | COOMe | Me | Et | Cl | H | H | O | C | H | C | CF3 | C | H | H | H |
| 74 | Ac | Me | Me | Me | H | H | O | C | H | C | CF3 | C | H | H | H |
| 75 | COOMe | Me | Et | Me | H | H | O | C | H | C | CF3 | C | H | H | H |
| 76 | Ac | Me | Me | CF3 | H | H | O | C | H | C | CF3 | C | H | H | H |
| 77 | COOMe | Me | Et | CF3 | H | H | O | C | H | C | CF3 | C | H | H | H |
| 78 | Ac | Me | Me | H | Me | H | O | C | H | C | CF3 | C | H | H | H |
| 79 | COOMe | Me | Et | H | Me | H | O | C | H | C | CF3 | C | H | H | H |

TABLE 2-continued

| Compound No. | R1 | R2 | R3 | X1 | X2 | X3 | Z | W1 | | W2 | | W3 | | Y4 | Y5 |
|---|---|---|---|---|---|---|---|---|---|---|---|---|---|---|---|
| | | | | | | | | Y1 | | Y2 | | Y3 | | | |
| 80 | Ac | Me | Me | H | CF3 | H | O | C | H | C | CF3 | C | H | H | H |
| 81 | Ac | Me | Me | Me | Me | H | O | C | H | C | CF3 | C | H | H | H |
| 82 | COOMe | Me | Et | Me | Me | H | O | C | H | C | CF3 | C | H | H | H |
| 83 | Ac | Me | Me | Cl | H | H | O | C | H | C | H | C | OCF3 | H | H |
| 84 | COOCH3 | Me | Et | Cl | H | H | O | C | H | C | H | C | OCF3 | H | H |
| 85 | H | Me | Me | Me | H | H | O | C | H | C | H | C | OCF3 | H | H |
| 86 | Ac | Me | Me | Me | H | H | O | C | H | C | H | C | OCF3 | H | H |
| 87 | COOCH3 | Me | Et | Me | H | H | O | C | H | C | H | C | OCF3 | H | H |
| 88 | Ac | Me | Et | Me | H | H | O | C | H | C | H | C | OCF3 | H | H |
| 89 | H | Me | Me | CF3 | H | H | O | C | H | C | H | C | OCF3 | H | H |
| 90 | Ac | Me | Me | CF3 | H | H | O | C | H | C | H | C | OCF3 | H | H |
| 91 | COEt | Me | Me | CF3 | H | H | O | C | H | C | H | C | OCF3 | H | H |
| 92 | CO-nBu | Me | Me | CF3 | H | H | O | C | H | C | H | C | OCF3 | H | H |
| 93 | CO-n-Oc | Me | Me | CF3 | H | H | O | C | H | C | H | C | OCF3 | H | H |
| 94 | CO-iPr | Me | Me | CF3 | H | H | O | C | H | C | H | C | OCF3 | H | H |
| 95 | CO-iBu | Me | Me | CF3 | H | H | O | C | H | C | H | C | OCF3 | H | H |
| 96 | CO-cPr | Me | Me | CF3 | H | H | O | C | H | C | H | C | OCF3 | H | H |
| 97 | CO-cBu | Me | Me | CF3 | H | H | O | C | H | C | H | C | OCF3 | H | H |
| 98 | CO—CH=CH2 | Me | Me | CF3 | H | H | O | C | H | C | H | C | OCF3 | H | H |
| 99 | CO—C(CH3)=CH2 | Me | Me | CF3 | H | H | O | C | H | C | H | C | OCF3 | H | H |
| 100 | CO—C(CH3)=CH(CH3 | Me | Me | CF3 | H | H | O | C | H | C | H | C | OCF3 | H | H |
| 101 | COOCH3 | Me | Me | CF3 | H | H | O | C | H | C | H | C | OCF3 | H | H |
| 102 | COOEt | Me | Me | CF3 | H | H | O | C | H | C | H | C | OCF3 | H | H |
| 103 | COO-nBu | Me | Me | CF3 | H | H | O | C | H | C | H | C | OCF3 | H | H |

TABLE 3

| Compound No. | R1 | R2 | R3 | X1 | X2 | X3 | Z | W1 | | W2 | | W3 | | Y4 | Y5 |
|---|---|---|---|---|---|---|---|---|---|---|---|---|---|---|---|
| | | | | | | | | Y1 | | Y2 | | Y3 | | | |
| 104 | COO-nOc | Me | Me | CF3 | H | H | O | C | H | C | H | C | OCF3 | H | H |
| 105 | COOPh | Me | Me | CF3 | H | H | O | C | H | C | H | C | OCF3 | H | H |
| 106 | COO-iBu | Me | Me | CF3 | H | H | O | C | H | C | H | C | OCF3 | H | H |
| 107 | COO—CH2CH=CH2 | Me | Me | CF3 | H | H | O | C | H | C | H | C | OCF3 | H | H |
| 108 | COO—CH2CCl3 | Me | Me | CF3 | H | H | O | C | H | C | H | C | OCF3 | H | H |
| 109 | COO—(CH2)2OCH3 | Me | Me | CF3 | H | H | O | C | H | C | H | C | OCF3 | H | H |
| 110 | COSCH3 | Me | Me | CF3 | H | H | O | C | H | C | H | C | OCF3 | H | H |
| 111 | H | Me | Et | CF3 | H | H | O | C | H | C | H | C | OCF3 | H | H |
| 112 | COOMe | Me | Et | CF3 | H | H | O | C | H | C | H | C | OCF3 | H | H |
| 113 | Ac | Me | Et | CF3 | H | H | O | C | H | C | H | C | OCF3 | H | H |
| 114 | Ac | —(CH2)3— | | CF3 | H | H | O | C | H | C | H | C | OCF3 | H | H |
| 115 | Ac | —(CH2)4— | | CF3 | H | H | O | C | H | C | H | C | OCF3 | H | H |
| 116 | Ac | Me | Me | H | Cl | H | O | C | H | C | H | C | OCF3 | H | H |
| 117 | H | Me | Me | H | Me | H | O | C | H | C | H | C | OCF3 | H | H |
| 118 | Ac | Me | Me | H | Me | H | O | C | H | C | H | C | OCF3 | H | H |
| 119 | H | Me | Et | H | Me | H | O | C | H | C | H | C | OCF3 | H | H |
| 120 | COOCH3 | Me | Et | H | Me | H | O | C | H | C | H | C | OCF3 | H | H |
| 121 | Ac | Me | Et | H | Me | H | O | C | H | C | H | C | OCF3 | H | H |
| 122 | Ac | Me | Me | H | CF3 | H | O | C | H | C | H | C | OCF3 | H | H |
| 123 | COOMe | Me | Et | H | CF3 | H | O | C | H | C | H | C | OCF3 | H | H |
| 124 | Ac | Me | CF3 | H | CF3 | H | O | C | H | C | H | C | OCF3 | H | H |
| 125 | Ac | —(CH2)3— | | H | CF3 | H | O | C | H | C | H | C | OCF3 | H | H |
| 126 | Ac | —(CH2)4— | | H | CF3 | H | O | C | H | C | H | C | OCF3 | H | H |
| 127 | Ac | Me | Me | Cl | Cl | H | O | C | H | C | H | C | OCF3 | H | H |
| 128 | COOMe | Me | Me | Cl | Cl | H | O | C | H | C | H | C | OCF3 | H | H |
| 129 | Ac | Me | Et | Cl | Cl | H | O | C | H | C | H | C | OCF3 | H | H |
| 130 | COOMe | Me | Et | Cl | Cl | H | O | C | H | C | H | C | OCF3 | H | H |
| 131 | H | Me | Me | Me | Me | H | O | C | H | C | H | C | OCF3 | H | H |
| 132 | Ac | Me | Me | Me | Me | H | O | C | H | C | H | C | OCF3 | H | H |
| 133 | COOMe | Me | Me | Me | Me | H | O | C | H | C | H | C | OCF3 | H | H |
| 134 | Ac | Me | Et | Me | Me | H | O | C | H | C | H | C | OCF3 | H | H |
| 135 | COOMe | Me | Et | Me | Me | H | O | C | H | C | H | C | OCF3 | H | H |
| 136 | Ac | Me | Me | CF3 | Cl | H | O | C | H | C | H | C | OCF3 | H | H |
| 137 | Ac | Me | Me | CF3 | H | Me | O | C | H | C | H | C | OCF3 | H | H |
| 138 | Ac | Me | Me | Cl | CF3 | H | O | C | H | C | H | C | OCF3 | H | H |
| 139 | Ac | Me | Me | Cl | H | H | O | C | H | C | OCF3 | C | H | H | H |
| 140 | COOMe | Me | Et | Cl | H | H | O | C | H | C | OCF3 | C | H | H | H |
| 141 | Ac | Me | Me | Me | H | H | O | C | H | C | OCF3 | C | H | H | H |
| 142 | COOMe | Me | Et | Me | H | H | O | C | H | C | OCF3 | C | H | H | H |
| 143 | Ac | Me | Me | CF3 | H | H | O | C | H | C | OCF3 | C | H | H | H |
| 144 | COOMe | Me | Et | CF3 | H | H | O | C | H | C | OCF3 | C | H | H | H |

TABLE 3-continued

| Compound No. | R1 | R2 | R3 | X1 | X2 | X3 | Z | W1 Y1 | | W2 Y2 | | W3 Y3 | | Y4 | Y5 |
|---|---|---|---|---|---|---|---|---|---|---|---|---|---|---|---|
| 145 | Ac | Me | Me | H | Me | H | O | C | H | C | OCF3 | C | H | H | H |
| 146 | COOMe | Me | Et | H | Me | H | O | C | H | C | OCF3 | C | H | H | H |
| 147 | Ac | Me | Me | H | CF3 | H | O | C | H | C | OCF3 | C | H | H | H |
| 148 | H | Me | Me | Me | Me | H | O | C | H | C | OCF3 | C | H | H | H |
| 149 | Ac | Me | Me | Me | Me | H | O | C | H | C | OCF3 | C | H | H | H |
| 150 | COOMe | Me | Et | Me | Me | H | O | C | H | C | OCF3 | C | H | H | H |
| 151 | Ac | Me | Me | Cl | H | H | O | C | H | C | H | C | SCF3 | H | H |
| 152 | COOCH3 | Me | Et | Cl | H | H | O | C | H | C | H | C | SCF3 | H | H |
| 153 | Ac | Me | Me | Me | H | H | O | C | H | C | H | C | SCF3 | H | H |
| 154 | COOCH3 | Me | Et | Me | H | H | O | C | H | C | H | C | SCF3 | H | H |
| 155 | Ac | Me | Et | Me | H | H | O | C | H | C | H | C | SCF3 | H | H |

TABLE 4

| Compound No. | R1 | R2 | R3 | X1 | X2 | X3 | Z | W1 Y1 | | W2 Y2 | | W3 Y3 | | Y4 | Y5 |
|---|---|---|---|---|---|---|---|---|---|---|---|---|---|---|---|
| 156 | Ac | Me | Me | CF3 | H | H | O | C | H | C | H | C | SCF3 | H | H |
| 157 | COOCH3 | Me | Et | CF3 | H | H | O | C | H | C | H | C | SCF3 | H | H |
| 158 | Ac | Me | Et | CF3 | H | H | O | C | H | C | H | C | SCF3 | H | H |
| 159 | Ac | Me | Me | H | Cl | H | O | C | H | C | H | C | SCF3 | H | H |
| 160 | Ac | Me | Me | H | Me | H | O | C | H | C | H | C | SCF3 | H | H |
| 161 | COOCH3 | Me | Et | H | Me | H | O | C | H | C | H | C | SCF3 | H | H |
| 162 | Ac | Me | Et | H | Me | H | O | C | H | C | H | C | SCF3 | H | H |
| 163 | Ac | Me | Me | H | CF3 | H | O | C | H | C | H | C | SCF3 | H | H |
| 164 | Ac | Me | Me | Me | Me | H | O | C | H | C | H | C | SCF3 | H | H |
| 165 | COOCH3 | Me | Et | Me | Me | H | O | C | H | C | H | C | SCF3 | H | H |
| 166 | Ac | Me | Et | Me | Me | H | O | C | H | C | H | C | SCF3 | H | H |
| 167 | Ac | Me | Me | CF3 | H | H | O | C | H | C | H | C | SO2CF3 | H | H |
| 168 | Ac | Me | Me | H | CF3 | H | O | C | H | C | H | C | SO2CF3 | H | H |
| 169 | Ac | Me | Me | Cl | H | H | O | C | H | C | SCF3 | C | H | H | H |
| 170 | COOCH3 | Me | Et | Cl | H | H | O | C | H | C | SCF3 | C | H | H | H |
| 171 | Ac | Me | Me | Me | H | H | O | C | H | C | SCF3 | C | H | H | H |
| 172 | COOCH3 | Me | Et | Me | H | H | O | C | H | C | SCF3 | C | H | H | H |
| 173 | Ac | Me | Me | CF3 | H | H | O | C | H | C | SCF3 | C | H | H | H |
| 174 | COOCH3 | Me | Et | CF3 | H | H | O | C | H | C | SCF3 | C | H | H | H |
| 175 | Ac | Me | Me | H | Me | H | O | C | H | C | SCF3 | C | H | H | H |
| 176 | COOCH3 | Me | Et | H | Me | H | O | C | H | C | SCF3 | C | H | H | H |
| 177 | Ac | Me | Me | Me | Me | H | O | C | H | C | SCF3 | C | H | H | H |
| 178 | COOCH3 | Me | Et | Me | Me | H | O | C | H | C | SCF3 | C | H | H | H |
| 179 | Ac | Me | Me | Cl | H | H | O | C | H | C | H | C | OCF2CHF2 | H | H |
| 180 | COOCH3 | Me | Et | Cl | H | H | O | C | H | C | H | C | OCF2CHF2 | H | H |
| 181 | H | Me | Me | Me | H | H | O | C | H | C | H | C | OCF2CHF2 | H | H |
| 182 | Ac | Me | Me | Me | H | H | O | C | H | C | H | C | OCF2CHF2 | H | H |
| 183 | COOCH3 | Me | Et | Me | H | H | O | C | H | C | H | C | OCF2CHF2 | H | H |
| 184 | Ac | Me | Et | Me | H | H | O | C | H | C | H | C | OCF2CHF2 | H | H |
| 185 | Ac | Me | Me | CF3 | H | H | O | C | H | C | H | C | OCF2CHF2 | H | H |
| 186 | COOCH3 | Me | Et | CF3 | H | H | O | C | H | C | H | C | OCF2CHF2 | H | H |
| 187 | Ac | Me | Et | CF3 | H | H | O | C | H | C | H | C | OCF2CHF2 | H | H |
| 188 | H | Me | Me | H | Me | H | O | C | H | C | H | C | OCF2CHF2 | H | H |
| 189 | Ac | Me | Me | H | Me | H | O | C | H | C | H | C | OCF2CHF2 | H | H |
| 190 | COOCH3 | Me | Et | H | Me | H | O | C | H | C | H | C | OCF2CHF2 | H | H |
| 191 | Ac | Me | Et | H | Me | H | O | C | H | C | H | C | OCF2CHF2 | H | H |
| 192 | Ac | Me | Me | H | CF3 | H | O | C | H | C | H | C | OCF2CHF2 | H | H |
| 193 | COOCH3 | Me | Et | H | CF3 | H | O | C | H | C | H | C | OCF2CHF2 | H | H |
| 194 | H | Me | Me | Me | Me | H | O | C | H | C | H | C | OCF2CHF2 | H | H |
| 195 | Ac | Me | Me | Me | Me | H | O | C | H | C | H | C | OCF2CHF2 | H | H |
| 196 | H | Me | Et | Me | Me | H | O | C | H | C | H | C | OCF2CHF2 | H | H |
| 197 | COOCH3 | Me | Et | Me | Me | H | O | C | H | C | H | C | OCF2CHF2 | H | H |
| 198 | Ac | Me | Et | Me | Me | H | O | C | H | C | H | C | OCF2CHF2 | H | H |
| 199 | Ac | Me | Me | Cl | H | H | O | C | H | C | OCF2CHF2 | C | H | H | H |
| 200 | COOCH3 | Me | Et | Cl | H | H | O | C | H | C | OCF2CHF2 | C | H | H | H |
| 201 | Ac | Me | Me | Me | H | H | O | C | H | C | OCF2CHF2 | C | H | H | H |
| 202 | COOCH3 | Me | Et | Me | H | H | O | C | H | C | OCF2CHF2 | C | H | H | H |
| 203 | Ac | Me | Me | CF3 | H | H | O | C | H | C | OCF2CHF2 | C | H | H | H |
| 204 | COOCH3 | Me | Et | CF3 | H | H | O | C | H | C | OCF2CHF2 | C | H | H | H |
| 205 | Ac | Me | Me | H | Me | H | O | C | H | C | OCF2CHF2 | C | H | H | H |
| 206 | COOCH3 | Me | Et | H | Me | H | O | C | H | C | OCF2CHF2 | C | H | H | H |
| 207 | Ac | Me | Me | Me | Me | H | O | C | H | C | OCF2CHF2 | C | H | H | H |

TABLE 5

| Compound No. | R1 | R2 | R3 | X1 | X2 | X3 | Z | W1 Y1 | | W2 Y2 | | W3 Y3 | Y4 | Y5 |
|---|---|---|---|---|---|---|---|---|---|---|---|---|---|---|
| 208 | COOCH3 | Me | Et | Me | Me | H | O | C | H | C | OCF2CHF2 | C | H | H | H |
| 209 | Ac | Me | Me | CF3 | H | H | O | C | H | C | H | C | OCH2CF3 | H | H |
| 210 | Ac | Me | Et | CF3 | H | H | O | C | H | C | H | C | OCH2CF3 | H | H |
| 211 | COOMe | Me | Et | CF3 | H | H | O | C | H | C | H | C | OCH2CF3 | H | H |
| 212 | Ac | Me | Me | H | CF3 | H | O | C | H | C | H | C | OCH2CF3 | H | H |
| 213 | Ac | Me | Me | CF3 | H | H | O | C | H | C | H | C | O-*i*Pr | H | H |
| 214 | Ac | Me | Me | H | CF3 | H | O | C | H | C | H | C | O-*i*Pr | H | H |
| 215 | Ac | Me | Me | CF3 | H | H | O | C | Cl | C | H | C | Cl | H | H |
| 216 | Ac | Me | Me | H | CF3 | H | O | C | Cl | C | H | C | Cl | H | H |
| 217 | Ac | Me | Me | CF3 | H | H | O | C | H | C | CF3 | C | H | CF3 | H |
| 218 | Ac | Me | Me | H | CF3 | H | O | C | H | C | CF3 | C | H | CF3 | H |
| 219 | Ac | Me | Me | Me | H | H | O | C | Cl | C | H | C | CF3 | H | H |
| 220 | COOCH3 | Me | Et | Me | H | H | O | C | Cl | C | H | C | CF3 | H | H |
| 221 | Ac | Me | Et | Me | H | H | O | C | Cl | C | H | C | CF3 | H | H |
| 222 | Ac | Me | Me | CF3 | H | H | O | C | Cl | C | H | C | CF3 | H | H |
| 223 | COOCH3 | Me | Et | CF3 | H | H | O | C | Cl | C | H | C | CF3 | H | H |
| 224 | Ac | Me | Et | CF3 | H | H | O | C | Cl | C | H | C | CF3 | H | H |
| 225 | Ac | Me | Me | H | Me | H | O | C | Cl | C | H | C | CF3 | H | H |
| 226 | COOCH3 | Me | Et | H | Me | H | O | C | Cl | C | H | C | CF3 | H | H |
| 227 | Ac | Me | Et | H | Me | H | O | C | Cl | C | H | C | CF3 | H | H |
| 228 | Ac | Me | Me | H | CF3 | H | O | C | Cl | C | H | C | CF3 | H | H |
| 229 | Ac | Me | Me | Me | Me | H | O | C | Cl | C | H | C | CF3 | H | H |
| 230 | COOCH3 | Me | Et | Me | Me | H | O | C | Cl | C | H | C | CF3 | H | H |
| 231 | Ac | Me | Et | Me | Me | H | O | C | Cl | C | H | C | CF3 | H | H |
| 232 | Ac | Me | Me | Cl | H | H | O | C | H | C | H | C | CF3 | H | H |
| 233 | COOCH3 | Me | Et | Cl | H | H | O | C | H | C | Cl | C | CF3 | H | H |
| 234 | Ac | Me | Me | Me | H | H | O | C | H | C | Cl | C | CF3 | H | H |
| 235 | COOCH3 | Me | Et | Me | H | H | O | C | H | C | Cl | C | CF3 | H | H |
| 236 | Ac | Me | Et | Me | H | H | O | C | H | C | Cl | C | CF3 | H | H |
| 237 | Ac | Me | Me | CF3 | H | H | O | C | H | C | Cl | C | CF3 | H | H |
| 238 | COOCH3 | Me | Et | CF3 | H | H | O | C | H | C | Cl | C | CF3 | H | H |
| 239 | Ac | Me | Et | CF3 | H | H | O | C | H | C | Cl | C | CF3 | H | H |
| 240 | Ac | Me | Me | H | Me | H | O | C | H | C | Cl | C | CF3 | H | H |
| 241 | COOCH3 | Me | Et | H | Me | H | O | C | H | C | Cl | C | CF3 | H | H |
| 242 | Ac | Me | Et | H | Me | H | O | C | H | C | Cl | C | CF3 | H | H |
| 243 | Ac | Me | Me | H | CF3 | H | O | C | H | C | Cl | C | CF3 | H | H |
| 244 | Ac | Me | Me | Me | Me | H | O | C | H | C | Cl | C | CF3 | H | H |
| 245 | COOCH3 | Me | Et | Me | Me | H | O | C | H | C | Cl | C | CF3 | H | H |
| 246 | Ac | Me | Et | Me | Me | H | O | C | H | C | Cl | C | CF3 | H | H |
| 247 | Ac | Me | Me | CF3 | H | H | O | C | H | C—O—CF2—CF2—O—C | | | | H | H |
| 248 | Ac | Me | Me | H | CF3 | H | O | C | H | C—O—CF2—CF2—O—C | | | | H | H |
| 249 | Ac | Me | Me | Me | H | H | O | C | Cl | C | H | C | OCF3 | H | H |
| 250 | COOCH3 | Me | Et | Me | H | H | O | C | Cl | C | H | C | OCF3 | H | H |
| 251 | Ac | Me | Et | Me | H | H | O | C | Cl | C | H | C | OCF3 | H | H |
| 252 | H | Me | Me | CF3 | H | H | O | C | Cl | C | H | C | OCF3 | H | H |
| 253 | Ac | Me | Me | CF3 | H | H | O | C | Cl | C | H | C | OCF3 | H | H |
| 254 | COOCH3 | Me | Et | CF3 | H | H | O | C | Cl | C | H | C | OCF3 | H | H |
| 255 | Ac | Me | Et | CF3 | H | H | O | C | Cl | C | H | C | OCF3 | H | H |
| 256 | Ac | Me | Me | H | Me | H | O | C | Cl | C | H | C | OCF3 | H | H |
| 257 | COOCH3 | Me | Et | H | Me | H | O | C | Cl | C | H | C | OCF3 | H | H |
| 258 | Ac | Me | Et | H | Me | H | O | C | Cl | C | H | C | OCF3 | H | H |
| 259 | Ac | Me | Me | H | CF3 | H | O | C | Cl | C | H | C | OCF3 | H | H |

TABLE 6

| Compound No. | R1 | R2 | R3 | X1 | X2 | X3 | Z | W1 Y1 | | W2 Y2 | | W3 Y3 | Y4 | Y5 |
|---|---|---|---|---|---|---|---|---|---|---|---|---|---|---|
| 260 | COOCH3 | Me | Et | H | CF3 | H | O | C | Cl | C | H | C | OCF3 | H | H |
| 261 | Ac | Me | Me | Me | Me | H | O | C | Cl | C | H | C | OCF3 | H | H |
| 262 | COOCH3 | Me | Et | Me | Me | H | O | C | Cl | C | H | C | OCF3 | H | H |
| 263 | Ac | Me | Et | Me | Me | H | O | C | Cl | C | H | C | OCF3 | H | H |
| 264 | Ac | Me | Me | Cl | H | H | O | C | H | C | Cl | C | OCF3 | H | H |
| 265 | COOCH3 | Me | Et | Cl | H | H | O | C | H | C | Cl | C | OCF3 | H | H |
| 266 | Ac | Me | Me | Me | H | H | O | C | H | C | Cl | C | OCF3 | H | H |
| 267 | COOCH3 | Me | Et | Me | H | H | O | C | H | C | Cl | C | OCF3 | H | H |
| 268 | Ac | Me | Et | Me | H | H | O | C | H | C | Cl | C | OCF3 | H | H |
| 269 | Ac | Me | Me | CF3 | H | H | O | C | H | C | Cl | C | OCF3 | H | H |
| 270 | COOCH3 | Me | Et | CF3 | H | H | O | C | H | C | Cl | C | OCF3 | H | H |
| 271 | Ac | Me | Et | CF3 | H | H | O | C | H | C | Cl | C | OCF3 | H | H |
| 272 | Ac | Me | Me | H | Me | H | O | C | H | C | Cl | C | OCF3 | H | H |

TABLE 6-continued

| Compound No. | R1 | R2 | R3 | X1 | X2 | X3 | Z | W1 Y1 | | W2 Y2 | | W3 Y3 | Y4 | Y5 |
|---|---|---|---|---|---|---|---|---|---|---|---|---|---|---|
| 273 | COOCH3 | Me | Et | H | Me | H | O | C | H | C | Cl | C | OCF3 | H | H |
| 274 | Ac | Me | Et | H | Me | H | O | C | H | C | Cl | C | OCF3 | H | H |
| 275 | Ac | Me | Me | H | CF3 | H | O | C | H | C | Cl | C | OCF3 | H | H |
| 276 | Ac | Me | Me | Me | Me | H | O | C | H | C | Cl | C | OCF3 | H | H |
| 277 | COOCH3 | Me | Et | Me | Me | H | O | C | H | C | Cl | C | OCF3 | H | H |
| 278 | Ac | Me | Et | Me | Me | H | O | C | H | C | Cl | C | OCF3 | H | H |
| 279 | Ac | Me | Me | CF3 | H | H | O | C | F | C | H | C | OCF3 | H | H |
| 280 | Ac | Me | Me | H | CF3 | H | O | C | F | C | H | C | OCF3 | H | H |
| 281 | Ac | Me | Me | CF3 | H | H | O | C | Br | C | H | C | CF3 | H | H |
| 282 | Ac | Me | Me | H | CF3 | H | O | C | Br | C | H | C | CF3 | H | H |
| 283 | Ac | Me | Me | Me | H | H | O | C | Me | C | H | C | CF3 | H | H |
| 284 | COOCH3 | Me | Et | Me | H | H | O | C | Me | C | H | C | CF3 | H | H |
| 285 | Ac | Me | Et | Me | H | H | O | C | Me | C | H | C | CF3 | H | H |
| 286 | Ac | Me | Me | CF3 | H | H | O | C | Me | C | H | C | CF3 | H | H |
| 287 | COOCH3 | Me | Et | CF3 | H | H | O | C | Me | C | H | C | CF3 | H | H |
| 288 | Ac | Me | Et | CF3 | H | H | O | C | Me | C | H | C | CF3 | H | H |
| 289 | Ac | Me | Me | H | Me | H | O | C | Me | C | H | C | CF3 | H | H |
| 290 | COOCH3 | Me | Et | H | Me | H | O | C | Me | C | H | C | CF3 | H | H |
| 291 | Ac | Me | Et | H | Me | H | O | C | Me | C | H | C | CF3 | H | H |
| 292 | Ac | Me | Me | H | CF3 | H | O | C | Me | C | H | C | CF3 | H | H |
| 293 | Ac | Me | Me | Me | Me | H | O | C | Me | C | H | C | CF3 | H | H |
| 294 | COOCH3 | Me | Et | Me | Me | H | O | C | Me | C | H | C | CF3 | H | H |
| 295 | Ac | Me | Et | Me | Me | H | O | C | Me | C | H | C | CF3 | H | H |
| 296 | Ac | Me | Me | Me | H | H | O | C | H | C | Me | C | CF3 | H | H |
| 297 | COOCH3 | Me | Et | Me | H | H | O | C | H | C | Me | C | CF3 | H | H |
| 298 | Ac | Me | Me | CF3 | H | H | O | C | H | C | Me | C | CF3 | H | H |
| 299 | COOCH3 | Me | Et | CF3 | H | H | O | C | H | C | Me | C | CF3 | H | H |
| 300 | Ac | Me | Me | H | Me | H | O | C | H | C | Me | C | CF3 | H | H |
| 301 | COOCH3 | Me | Et | H | Me | H | O | C | H | C | Me | C | CF3 | H | H |
| 302 | Ac | Me | Me | Me | Me | H | O | C | H | C | Me | C | CF3 | H | H |
| 303 | COOCH3 | Me | Et | Me | Me | H | O | C | H | C | Me | C | CF3 | H | H |
| 304 | Ac | Me | Me | Cl | H | H | O | C | Me | C | H | C | OCF3 | H | H |
| 305 | COOCH3 | Me | Et | Cl | H | H | O | C | Me | C | H | C | OCF3 | H | H |
| 306 | Ac | Me | Me | Me | H | H | O | C | Me | C | H | C | OCF3 | H | H |
| 307 | COOCH3 | Me | Et | Me | H | H | O | C | Me | C | H | C | OCF3 | H | H |
| 308 | Ac | Me | Me | CF3 | H | H | O | C | Me | C | H | C | OCF3 | H | H |
| 309 | COOCH3 | Me | Et | CF3 | H | H | O | C | Me | C | H | C | OCF3 | H | H |
| 310 | Ac | Me | Me | H | Me | H | O | C | Me | C | H | C | OCF3 | H | H |
| 311 | COOCH3 | Me | Et | H | Me | H | O | C | Me | C | H | C | OCF3 | H | H |

TABLE 7

| Compound No. | R1 | R2 | R3 | X1 | X2 | X3 | Z | W1 Y1 | | W2 Y2 | | W3 Y3 | Y4 | Y5 |
|---|---|---|---|---|---|---|---|---|---|---|---|---|---|---|
| 312 | Ac | Me | Me | H | CF3 | H | O | C | Me | C | H | C | OCF3 | H | H |
| 313 | Ac | Me | Me | Me | Me | H | O | C | Me | C | H | C | OCF3 | H | H |
| 314 | COOCH3 | Me | Et | Me | Me | H | O | C | Me | C | H | C | OCF3 | H | H |
| 315 | Ac | Me | Me | Me | H | H | O | C | H | C | Me | C | OCF3 | H | H |
| 316 | COOCH3 | Me | Et | Me | H | H | O | C | H | C | Me | C | OCF3 | H | H |
| 317 | Ac | Me | Me | CF3 | H | H | O | C | H | C | Me | C | OCF3 | H | H |
| 318 | COOCH3 | Me | Et | CF3 | H | H | O | C | H | C | Me | C | OCF3 | H | H |
| 319 | Ac | Me | Me | H | Me | H | O | C | H | C | Me | C | OCF3 | H | H |
| 320 | COOCH3 | Me | Et | H | Me | H | O | C | H | C | Me | C | OCF3 | H | H |
| 321 | Ac | Me | Me | Me | Me | H | O | C | H | C | Me | C | OCF3 | H | H |
| 322 | COOCH3 | Me | Et | Me | Me | H | O | C | H | C | Me | C | OCF3 | H | H |
| 323 | Ac | Me | Me | Me | H | H | O | C | Cl | C | H | C | OCF2CHF2 | H | H |
| 324 | COOCH3 | Me | Et | Me | H | H | O | C | Cl | C | H | C | OCF2CHF2 | H | H |
| 325 | Ac | Me | Et | Me | H | H | O | C | Cl | C | H | C | OCF2CHF2 | H | H |
| 326 | Ac | Me | Me | CF3 | H | H | O | C | Cl | C | H | C | OCF2CHF2 | H | H |
| 327 | COOCH3 | Me | Et | CF3 | H | H | O | C | Cl | C | H | C | OCF2CHF2 | H | H |
| 328 | Ac | Me | Et | CF3 | H | H | O | C | Cl | C | H | C | OCF2CHF2 | H | H |
| 329 | H | Me | Me | H | Me | H | O | C | Cl | C | H | C | OCF2CHF2 | H | H |
| 330 | Ac | Me | Me | H | Me | H | O | C | Cl | C | H | C | OCF2CHF2 | H | H |
| 331 | H | Me | Et | H | Me | H | O | C | Cl | C | H | C | OCF2CHF2 | H | H |
| 332 | COOCH3 | Me | Et | H | Me | H | O | C | Cl | C | H | C | OCF2CHF2 | H | H |
| 333 | Ac | Me | Et | H | Me | H | O | C | Cl | C | H | C | OCF2CHF2 | H | H |
| 334 | H | Me | Me | Me | Me | H | O | C | Cl | C | H | C | OCF2CHF2 | H | H |
| 335 | Ac | Me | Me | Me | Me | H | O | C | Cl | C | H | C | OCF2CHF2 | H | H |
| 336 | H | Me | Et | Me | Me | H | O | C | Cl | C | H | C | OCF2CHF2 | H | H |
| 337 | COOCH3 | Me | Et | Me | Me | H | O | C | Cl | C | H | C | OCF2CHF2 | H | H |

TABLE 7-continued

| Compound No. | R1 | R2 | R3 | X1 | X2 | X3 | Z | W1 Y1 | | W2 Y2 | | W3 Y3 | | Y4 | Y5 |
|---|---|---|---|---|---|---|---|---|---|---|---|---|---|---|---|
| 338 | Ac | Me | Et | Me | Me | H | O | C | Cl | C | H | C | OCF2CHF2 | H | H |
| 339 | Ac | Me | Me | Me | H | H | O | C | H | C | Cl | C | OCF2CHF2 | H | H |
| 340 | COOCH3 | Me | Et | Me | H | H | O | C | H | C | Cl | C | OCF2CHF2 | H | H |
| 341 | Ac | Me | Et | Me | H | H | O | C | H | C | Cl | C | OCF2CHF2 | H | H |
| 342 | Ac | Me | Me | CF3 | H | H | O | C | H | C | Cl | C | OCF2CHF2 | H | H |
| 343 | COOCH3 | Me | Et | CF3 | H | H | O | C | H | C | Cl | C | OCF2CHF2 | H | H |
| 344 | Ac | Me | Et | CF3 | H | H | O | C | H | C | Cl | C | OCF2CHF2 | H | H |
| 345 | Ac | Me | Me | H | Me | H | O | C | H | C | Cl | C | OCF2CHF2 | H | H |
| 346 | COOCH3 | Me | Et | H | Me | H | O | C | H | C | Cl | C | OCF2CHF2 | H | H |
| 347 | Ac | Me | Et | H | Me | H | O | C | H | C | Cl | C | OCF2CHF2 | H | H |
| 348 | Ac | Me | Me | Me | Me | H | O | C | H | C | Cl | C | OCF2CHF2 | H | H |
| 349 | COOCH3 | Me | Et | Me | Me | H | O | C | H | C | Cl | C | OCF2CHF2 | H | H |
| 350 | Ac | Me | Et | Me | Me | H | O | C | H | C | Cl | C | OCF2CHF2 | H | H |
| 351 | Ac | Me | Me | CF3 | H | H | O | C | Cl | C | H | C | CF3 | H | Cl |
| 352 | Ac | Me | Me | H | CF3 | H | O | C | Cl | C | H | C | CF3 | H | Cl |
| 353 | Ac | Me | Me | CF3 | H | H | O | C | Cl | C | H | C | OCF3 | H | Cl |
| 354 | Ac | Me | Me | H | CF3 | H | O | C | Cl | C | H | C | OCF3 | H | Cl |
| 355 | Ac | Me | Me | Me | H | H | O | C | Me | C | H | C | OCF2CHF2 | H | H |
| 356 | COOCH3 | Me | Et | Me | H | H | O | C | Me | C | H | C | OCF2CHF2 | H | H |
| 357 | Ac | Me | Me | CF3 | H | H | O | C | Me | C | H | C | OCF2CHF2 | H | H |
| 358 | COOCH3 | Me | Et | CF3 | H | H | O | C | Me | C | H | C | OCF2CHF2 | H | H |
| 359 | Ac | Me | Me | H | Me | H | O | C | Me | C | H | C | OCF2CHF2 | H | H |
| 360 | COOCH3 | Me | Et | H | Me | H | O | C | Me | C | H | C | OCF2CHF2 | H | H |
| 361 | Ac | Me | Me | Me | Me | H | O | C | Me | C | H | C | OCF2CHF2 | H | H |
| 362 | COOCH3 | Me | Et | Me | Me | H | O | C | Me | C | H | C | OCF2CHF2 | H | H |
| 363 | Ac | Me | Me | CF3 | H | H | O | C | H | C | H | C | (4"-CF3—Ph)—O | H | H |

TABLE 8

| Compound No. | R1 | R2 | R3 | X1 | X2 | X3 | Z | W1 Y1 | | W2 Y2 | | W3 Y3 | | Y4 | Y5 |
|---|---|---|---|---|---|---|---|---|---|---|---|---|---|---|---|
| 364 | Ac | Me | Me | H | CF3 | H | O | C | H | C | H | C | (4"-CF3—Ph)—O | H | H |
| 365 | Ac | Me | Me | CF3 | H | H | O | C | H | C | H | C | 4"-CF3—Ph | H | H |
| 366 | Ac | Me | Me | H | CF3 | H | O | C | H | C | H | C | 4"-CF3—Ph | H | H |
| 367 | Ac | Me | Me | Cl | H | H | OCH2 | C | H | C | H | C | Cl | H | H |
| 368 | Ac | Me | Me | H | Cl | H | OCH2 | C | H | C | H | C | Cl | H | H |
| 369 | Ac | Me | Me | Cl | H | H | CO | C | H | C | H | C | Cl | H | H |
| 370 | Ac | Me | Me | H | Cl | H | CO | C | H | C | H | C | Cl | H | H |
| 371 | Ac | Me | Me | Cl | H | H | S | C | H | C | H | C | Cl | H | H |
| 372 | Ac | Me | Me | H | Cl | H | S | C | H | C | H | C | Cl | H | H |
| 373 | Ac | Me | Me | Cl | H | H | SO | C | H | C | H | C | Cl | H | H |
| 374 | Ac | Me | Me | Cl | H | H | SO2 | C | H | C | H | C | Cl | H | H |
| 375 | Ac | Me | CH2—OAc | Cl | H | H | SO2 | C | H | C | H | C | Cl | H | H |
| 376 | Ac | Me | Me | H | Cl | H | SO2 | C | H | C | H | C | Cl | H | H |
| 377 | Ac | Me | Me | Cl | H | H | CH2 | C | H | C | H | C | Cl | H | H |
| 378 | Ac | Me | Me | H | Cl | H | CH2 | C | H | C | H | C | Cl | H | H |
| 379 | Ac | Me | Me | H | Et | H | O | C | H | C | Cl | C | CF3 | H | H |
| 380 | COOCH3 | Me | Et | H | Et | H | O | C | H | C | Cl | C | CF3 | H | H |
| 381 | COOCH3 | Me | Me | H | F | H | O | C | H | C | Cl | C | CF3 | H | H |
| 382 | COOCH3 | Me | Me | COOMe | H | H | O | C | H | C | Cl | C | CF3 | H | H |
| 383 | Ac | Me | Me | H | OMe | H | O | C | H | C | Cl | C | CF3 | H | H |
| 384 | COOCH3 | Me | Et | H | OMe | H | O | C | H | C | Cl | C | CF3 | H | H |
| 385 | Ac | Me | Me | H | Et | H | O | C | Cl | C | H | C | CF3 | H | H |
| 386 | COOCH3 | Me | Et | H | Et | H | O | C | Cl | C | H | C | CF3 | H | H |
| 387 | COOCH3 | Me | Me | H | F | H | O | C | Cl | C | H | C | CF3 | H | H |
| 388 | COOCH3 | Me | Me | COOMe | H | H | O | C | Cl | C | H | C | CF3 | H | H |
| 389 | Ac | Me | Me | H | OMe | H | O | C | Cl | C | H | C | CF3 | H | H |
| 390 | COOCH3 | Me | Et | H | OMe | H | O | C | Cl | C | H | C | CF3 | H | H |
| 391 | Ac | Me | Me | H | Et | H | O | C | H | C | H | C | CF3 | H | H |
| 392 | COOCH3 | Me | Et | H | Et | H | O | C | H | C | H | C | CF3 | H | H |
| 393 | COOCH3 | Me | Me | F | F | H | O | C | H | C | H | C | CF3 | H | H |
| 394 | COOCH3 | Me | Me | H | F | H | O | C | H | C | H | C | CF3 | H | H |
| 395 | COOCH3 | Me | Me | COOMe | H | H | O | C | H | C | H | C | CF3 | H | H |
| 396 | Ac | Me | Me | F | H | H | O | C | H | C | H | C | CF3 | H | H |
| 397 | COOCH3 | Me | Et | Me | Me | H | O(CH2)3O | C | H | C | H | C | CF3 | H | H |
| 398 | COOCH3 | Me | Et | Me | Me | H | O—CH2—C(CH3)2—CH2—O | C | H | C | H | C | CF3 | H | H |
| 399 | COOCH3 | Me | Et | Me | Me | H | O(CH2)2O | C | H | C | H | C | CF3 | H | H |
| 400 | Ac | Me | Me | H | OMe | H | O | C | H | C | H | C | CF3 | H | H |
| 401 | COOCH3 | Me | Et | H | OMe | H | O | C | H | C | H | C | CF3 | H | H |
| 402 | Ac | Me | Me | H | Et | H | O | C | Me | C | H | C | CF3 | H | H |

TABLE 8-continued

| Compound No. | R1 | R2 | R3 | X1 | X2 | X3 | Z | W1 Y1 | | W2 Y2 | | W3 Y3 | | Y4 | Y5 |
|---|---|---|---|---|---|---|---|---|---|---|---|---|---|---|---|
| 403 | COOCH3 | Me | Et | H | Et | H | O | C | Me | C | H | C | CF3 | H | H |
| 404 | COOCH3 | Me | Me | H | F | H | O | C | Me | C | H | C | CF3 | H | H |
| 405 | COOCH3 | Me | Me | COOMe | H | H | O | C | Me | C | H | C | CF3 | H | H |
| 406 | Ac | Me | Me | H | OMe | H | O | C | Me | C | H | C | CF3 | H | H |
| 407 | COOCH3 | Me | Et | H | OMe | H | O | C | Me | C | H | C | CF3 | H | H |
| 408 | Ac | Me | Me | H | Et | H | O | C | H | C | Me | C | CF3 | H | H |
| 409 | COOCH3 | Me | Et | H | Et | H | O | C | H | C | Me | C | CF3 | H | H |
| 410 | COOCH3 | Me | Me | H | F | H | O | C | H | C | Me | C | CF3 | H | H |
| 411 | COOCH3 | Me | Me | COOMe | H | H | O | C | H | C | Me | C | CF3 | H | H |
| 412 | Ac | Me | Me | H | OMe | H | O | C | H | C | Me | C | CF3 | H | H |
| 413 | COOCH3 | Me | Et | H | OMe | H | O | C | H | C | Me | C | CF3 | H | H |
| 414 | Ac | Me | Me | H | Me | H | O | C | CF3 | C | H | C | CF3 | H | H |
| 415 | COOCH3 | Me | Et | H | Me | H | O | C | CF3 | C | H | C | CF3 | H | H |

TABLE 9

| Compound No. | R1 | R2 | R3 | X1 | X2 | X3 | Z | W1 Y1 | | W2 Y2 | | W3 Y3 | | Y4 | Y5 |
|---|---|---|---|---|---|---|---|---|---|---|---|---|---|---|---|
| 416 | Ac | Me | Me | H | Me | H | O | C | H | C | CF3 | C | CF3 | H | H |
| 417 | COOCH3 | Me | Et | H | Me | H | O | C | H | C | CF3 | C | CF3 | H | H |
| 418 | COOCH3 | Me | Et | H | Me | H | O | C | H | C | H | C | CF2CHFCF3 | H | H |
| 419 | COOCH3 | Me | Et | Me | Me | H | O | C | H | C | H | C | CF2CHFCF3 | H | H |
| 420 | Ac | Me | Me | H | F | H | O | C | H | C | H | C | CF2CHFCF3 | H | H |
| 421 | COOCH3 | Me | Et | H | Et | H | O | C | H | C | H | C | CF2CHFCF3 | H | H |
| 422 | Ac | Me | Me | H | Et | H | O | C | H | C | Cl | C | OCF3 | H | H |
| 423 | COOCH3 | Me | Et | H | Et | H | O | C | H | C | Cl | C | OCF3 | H | H |
| 424 | COOCH3 | Me | Me | H | F | H | O | C | H | C | Cl | C | OCF3 | H | H |
| 425 | Ac | Me | Me | H | F | H | O | C | H | C | Cl | C | OCF3 | H | H |
| 426 | COOCH3 | Me | Me | COOMe | H | H | O | C | H | C | Cl | C | OCF3 | H | H |
| 427 | Ac | Me | Me | H | OMe | H | O | C | H | C | Cl | C | OCF3 | H | H |
| 428 | COOCH3 | Me | Et | H | OMe | H | O | C | H | C | Cl | C | OCF3 | H | H |
| 429 | Ac | Me | Me | H | Et | H | O | C | Cl | C | H | C | OCF3 | H | H |
| 430 | COOCH3 | Me | Et | H | Et | H | O | C | Cl | C | H | C | OCF3 | H | H |
| 431 | COOCH3 | Me | Me | H | F | H | O | C | Cl | C | H | C | OCF3 | H | H |
| 432 | COOCH3 | Me | Me | COOMe | H | H | O | C | Cl | C | H | C | OCF3 | H | H |
| 433 | COOCH3 | Me | Et | H | OMe | H | O | C | Cl | C | H | C | OCF3 | H | H |
| 434 | Ac | Me | Me | H | OMe | H | O | C | Cl | C | H | C | OCF3 | H | H |
| 435 | Ac | Me | Me | H | CF3 | H | S | C | H | C | H | C | OCF3 | H | H |
| 436 | Ac | Me | Me | H | CF3 | H | — | C | H | C | H | C | OCF3 | H | H |
| 437 | Ac | Me | Me | H | CF3 | H | SO2 | C | H | C | H | C | OCF3 | H | H |
| 438 | CON(CH3)2 | Me | Me | H | CF3 | H | O | C | H | C | H | C | OCF3 | H | H |
| 439 | SO2CH3 | Me | Me | H | CF3 | H | O | C | H | C | H | C | OCF3 | H | H |
| 440 | Ac | Me | Me | H | CF3 | H | OCH2 | C | H | C | H | C | OCF3 | H | H |
| 441 | CH3 | Me | Me | H | CF3 | H | O | C | H | C | H | C | OCF3 | H | H |
| 442 | Ac | Me | Me | H | CHF2 | H | O | C | H | C | H | C | OCF3 | H | H |
| 443 | COOCH3 | Me | Et | H | CHF2 | H | O | C | H | C | H | C | OCF3 | H | H |
| 444 | Ac | Me | Me | H | COOMe | H | O | C | H | C | H | C | OCF3 | H | H |
| 445 | Ac | Me | Me | H | Et | H | O | C | H | C | H | C | OCF3 | H | H |
| 446 | COOCH3 | Me | Et | H | Et | H | O | C | H | C | H | C | OCF3 | H | H |
| 447 | Ac | Me | Me | H | F | H | O | C | H | C | H | C | OCF3 | H | H |
| 448 | H | Me | Me | H | F | H | O | C | H | C | H | C | OCF3 | H | H |
| 449 | COOCH3 | Me | Me | H | F | H | O | C | H | C | H | C | OCF3 | H | H |
| 450 | COOCH3 | Me | Me | F | F | H | O | C | H | C | H | C | OCF3 | H | H |
| 451 | Ac | Me | Me | F | F | H | O | C | H | C | H | C | OCF3 | H | H |
| 452 | Ac | Me | Me | CF3 | H | Cl | O | C | H | C | H | C | OCF3 | H | H |
| 453 | Ac | Me | Me | CF3 | H | H | S | C | H | C | H | C | OCF3 | H | H |
| 454 | Ac | Me | Me | CF3 | H | H | — | C | H | C | H | C | OCF3 | H | H |
| 455 | Ac | Me | Me | CF3 | H | H | SO2 | C | H | C | H | C | OCF3 | H | H |
| 456 | CON(CH3)2 | Me | Me | CF3 | H | H | O | C | H | C | H | C | OCF3 | H | H |
| 457 | SO2CH3 | Me | Me | CF3 | H | H | O | C | H | C | H | C | OCF3 | H | H |
| 458 | CH3 | Me | Me | CF3 | H | H | O | C | H | C | H | C | OCF3 | H | H |
| 459 | Ac | Me | Me | COOMe | H | H | O | C | H | C | H | C | OCF3 | H | H |
| 460 | Ac | Me | Me | F | H | H | O | C | H | C | H | C | OCF3 | H | H |
| 461 | COCH2OMe | Me | Me | CF3 | H | H | O | C | H | C | H | C | OCF3 | H | H |
| 462 | COCH2OCOMe | Me | Me | CF3 | H | H | O | C | H | C | H | C | OCF3 | H | H |
| 463 | COOCH3 | Me | Me | COOMe | H | H | O | C | H | C | H | C | OCF3 | H | H |
| 464 | COOCH3 | Me | Et | Me | Me | H | OCH2 | C | H | C | H | C | OCF3 | H | H |
| 465 | CO(CH2)7CH3 | Me | Et | H | Me | H | O | C | H | C | H | C | OCF3 | H | H |
| 466 | COCH2OMe | Me | Et | H | Me | H | O | C | H | C | H | C | OCF3 | H | H |
| 467 | COCH2OCOMe | Me | Et | H | Me | H | O | C | H | C | H | C | OCF3 | H | H |

TABLE 10

| Compound No. | R1 | R2 | R3 | X1 | X2 | X3 | Z | W1 Y1 | | W2 Y2 | | W3 Y3 | | Y4 | Y5 |
|---|---|---|---|---|---|---|---|---|---|---|---|---|---|---|---|
| 468 | CH2COOMe | Me | Et | H | Me | H | O | C | H | C | H | C | OCF3 | H | H |
| 469 | CO-cPr | Me | Et | H | Me | H | O | C | H | C | H | C | OCF3 | H | H |
| 470 | 4-OMe | Me | Et | H | Me | H | O | C | H | C | H | C | OCF3 | H | H |
| 471 | CH2—O—CH2CH2—O—CH3 | Me | Et | H | Me | H | O | C | H | C | H | C | OCF3 | H | H |
| 472 | Ac | Me | Me | H | OMe | H | O | C | H | C | H | C | OCF3 | H | H |
| 473 | COOCH3 | Me | Et | H | OMe | H | O | C | H | C | H | C | OCF3 | H | H |
| 474 | Ac | Me | Me | H | Et | H | O | C | Me | C | H | C | OCF3 | H | H |
| 475 | COOCH3 | Me | Et | H | Et | H | O | C | Me | C | H | C | OCF3 | H | H |
| 476 | COOCH3 | Me | Me | H | F | H | O | C | Me | C | H | C | OCF3 | H | H |
| 477 | COOCH3 | Me | Me | COOMe | H | H | O | C | Me | C | H | C | OCF3 | H | H |
| 478 | Ac | Me | Me | H | OMe | H | O | C | Me | C | H | C | OCF3 | H | H |
| 479 | COOCH3 | Me | Et | H | OMe | H | O | C | Me | C | H | C | OCF3 | H | H |
| 480 | Ac | Me | Me | H | Et | H | O | C | H | C | Me | C | OCF3 | H | H |
| 481 | COOCH3 | Me | Et | H | Et | H | O | C | H | C | Me | C | OCF3 | H | H |
| 482 | COOCH3 | Me | Me | H | F | H | O | C | H | C | Me | C | OCF3 | H | H |
| 483 | COOCH3 | Me | Me | COOMe | H | H | O | C | H | C | Me | C | OCF3 | H | H |
| 484 | Ac | Me | Me | H | OMe | H | O | C | H | C | Me | C | OCF3 | H | H |
| 485 | COOCH3 | Me | Et | H | OMe | H | O | C | H | C | Me | C | OCF3 | H | H |
| 486 | Ac | Me | Me | H | Me | H | O | C | OCF3 | C | H | C | OCF3 | H | H |
| 487 | COOCH3 | Me | Et | H | Me | H | O | C | OCF3 | C | H | C | OCF3 | H | H |
| 488 | Ac | Me | Me | H | Me | H | O | C | H | C | OCF3 | C | OCF3 | H | H |
| 489 | COOCH3 | Me | Et | H | Me | H | O | C | H | C | OCF3 | C | OCF3 | H | H |
| 490 | Ac | Me | Me | H | OMe | H | O | C | H | C | Cl | C | OCF2CHF2 | H | H |
| 491 | COOCH3 | Me | Et | H | OMe | H | O | C | H | C | Cl | C | OCF2CHF2 | H | H |
| 492 | COOCH3 | Me | Me | COOMe | H | H | O | C | H | C | Cl | C | OCF2CHF2 | H | H |
| 493 | COOCH3 | Me | Me | H | F | H | O | C | H | C | Cl | C | OCF2CHF2 | H | H |
| 494 | Ac | Me | Me | H | Et | H | O | C | H | C | Cl | C | OCF2CHF2 | H | H |
| 495 | COOCH3 | Me | Et | H | Et | H | O | C | H | C | Cl | C | OCF2CHF2 | H | H |
| 496 | Ac | Me | Et | H | CF3 | H | O | C | Cl | C | H | C | OCF2CHF2 | H | H |
| 497 | COOCH3 | Me | Et | H | OMe | H | O | C | H | C | H | C | OCF2CHF2 | H | H |
| 498 | Ac | Me | Me | H | OMe | H | O | C | H | C | H | C | OCF2CHF2 | H | H |
| 499 | COOCH3 | Me | Me | COOMe | H | H | O | C | H | C | H | C | OCF2CHF2 | H | H |
| 500 | Ac | Me | Me | F | H | H | O | C | H | C | H | C | OCF2CHF2 | H | H |
| 501 | COOCH3 | Me | Me | H | F | H | O | C | H | C | H | C | OCF2CHF2 | H | H |
| 502 | COOCH3 | Me | Me | F | F | H | O | C | H | C | H | C | OCF2CHF2 | H | H |
| 503 | Ac | Me | Me | H | Et | H | O | C | H | C | H | C | OCF2CHF2 | H | H |
| 504 | COOCH3 | Me | Et | H | Et | H | O | C | H | C | H | C | OCF2CHF2 | H | H |
| 505 | Ac | Me | Me | H | OMe | H | O | C | Cl | C | H | C | OCF2CHF2 | H | H |
| 506 | COOCH3 | Me | Et | H | OMe | H | O | C | Cl | C | H | C | OCF2CHF2 | H | H |
| 507 | COOCH3 | Me | Me | COOMe | H | H | O | C | Cl | C | H | C | OCF2CHF2 | H | H |
| 508 | COOCH3 | Me | Me | H | F | H | O | C | Cl | C | H | C | OCF2CHF2 | H | H |
| 509 | Ac | Me | Me | H | Et | H | O | C | Cl | C | H | C | OCF2CHF2 | H | H |
| 510 | COOCH3 | Me | Et | H | Et | H | O | C | Cl | C | H | C | OCF2CHF2 | H | H |
| 511 | Ac | Me | Me | H | OMe | H | O | C | Me | C | H | C | OCF2CHF2 | H | H |
| 512 | COOCH3 | Me | Et | H | OMe | H | O | C | Me | C | H | C | OCF2CHF2 | H | H |
| 513 | COOCH3 | Me | Me | COOMe | H | H | O | C | Me | C | H | C | OCF2CHF2 | H | H |
| 514 | COOCH3 | Me | Me | H | F | H | O | C | Me | C | H | C | OCF2CHF2 | H | H |
| 515 | Ac | Me | Me | H | Et | H | O | C | Me | C | H | C | OCF2CHF2 | H | H |
| 516 | COOCH3 | Me | Et | H | Et | H | O | C | Me | C | H | C | OCF2CHF2 | H | H |
| 517 | Ac | Me | Me | H | OMe | H | O | C | H | C | Me | C | OCF2CHF2 | H | H |
| 518 | COOCH3 | Me | Et | H | OMe | H | O | C | H | C | Me | C | OCF2CHF2 | H | H |
| 519 | COOCH3 | Me | Me | COOMe | H | H | O | C | H | C | Me | C | OCF2CHF2 | H | H |

TABLE 11

| Compound No. | R1 | R2 | R3 | X1 | X2 | X3 | Z | W1 Y1 | | W2 Y2 | | W3 Y3 | | Y4 | Y5 |
|---|---|---|---|---|---|---|---|---|---|---|---|---|---|---|---|
| 520 | COOCH3 | Me | Me | H | F | H | O | C | H | C | Me | C | OCF2CHF2 | H | H |
| 521 | Ac | Me | Me | H | Et | H | O | C | H | C | Me | C | OCF2CHF2 | H | H |
| 522 | COOCH3 | Me | Et | H | Et | H | O | C | H | C | Me | C | OCF2CHF2 | H | H |
| 523 | Ac | Me | Me | H | Me | H | O | C | OMe | C | H | C | OCF2CHF2 | H | H |
| 524 | COOCH3 | Me | Et | H | Me | H | O | C | OMe | C | H | C | OCF2CHF2 | H | H |
| 525 | Ac | Me | Me | H | Me | H | O | C | Cl | C | Cl | C | OCF2CHF2 | H | H |
| 526 | COOCH3 | Me | Et | H | Me | H | O | C | Cl | C | Cl | C | OCF2CHF2 | H | H |
| 527 | Ac | Me | Me | H | Me | H | O | C | Cl | C | H | C | OCF2CHF2 | Cl | H |
| 528 | COOCH3 | Me | Et | H | Me | H | O | C | Cl | C | H | C | OCF2CHF2 | Cl | H |
| 529 | COOCH3 | Me | Et | H | Me | H | O | C | H | C | H | C | OCF2CHFCF3 | H | H |
| 530 | COOCH3 | Me | Et | Me | Me | H | O | C | H | C | H | C | OCF2CHFCF3 | H | H |
| 531 | COOCH3 | Me | Et | H | Me | H | O | C | H | C | H | C | OCF2CF2CF3 | H | H |

TABLE 11-continued

| Compound No. | R1 | R2 | R3 | X1 | X2 | X3 | Z | W1 Y1 | | W2 Y2 | | W3 | Y3 | Y4 | Y5 |
|---|---|---|---|---|---|---|---|---|---|---|---|---|---|---|---|
| 532 | COOCH3 | Me | Et | Me | Me | H | O | C | H | C | H | C | OCF2CF2CF3 | H | H |
| 533 | COOCH3 | Me | Et | H | Me | H | O | C | H | C | H | C | OCF2CHFCF2CF3 | H | H |
| 534 | COOCH3 | Me | Et | Me | Me | H | O | C | H | C | H | C | OCF2CHFCF2CF3 | H | H |
| 535 | COOCH3 | Me | Et | H | Me | H | O | C | H | C | H | C | OCF2CHFOCF3 | H | H |
| 536 | COOCH3 | Me | Et | Me | Me | H | O | C | H | C | H | C | OCF2CHFOCF3 | H | H |
| 537 | COOCH3 | Me | Et | H | Me | H | O | C | H | C | H | C | OCF2CHFOCF2CF3 | H | H |
| 538 | COOCH3 | Me | Et | Me | Me | H | O | C | H | C | H | C | OCF2CHFOCF2CF3 | H | H |
| 539 | COOCH3 | Me | Et | Me | H | H | O | C | H | C | H | C | OCF2CHFOCF2CF2CF3 | H | H |
| 540 | COOCH3 | Me | Et | H | Me | H | O | C | H | C | H | C | OCF2CHFOCF2CF2CF3 | H | H |
| 541 | COOCH3 | Me | Et | Me | Me | H | O | C | H | C | H | C | OCF2CHFOCF2CF2CF3 | H | H |
| 542 | Ac | Me | Et | H | Me | H | O | C | H | C | H | C | OCF2CHFOCF2CF2CF3 | H | H |
| 543 | Ac | Me | Me | H | Me | H | O | C | H | C | H | C | OCF2CHFOCF2CF2CF3 | H | H |
| 544 | Ac | Me | Et | Me | Me | H | O | C | H | C | H | C | OCF2CHFOCF2CF2CF3 | H | H |
| 545 | Ac | Me | Me | Me | Me | H | O | C | H | C | H | C | OCF2CHFOCF2CF2CF3 | H | H |
| 546 | Ac | Me | Me | H | MeO | H | O | C | H | C | H | C | OCF2CHFOCF2CF2CF3 | H | H |
| 547 | COOCH3 | Me | Me | H | MeO | H | O | C | H | C | H | C | OCF2CHFOCF2CF2CF3 | H | H |
| 548 | Ac | Me | Me | H | F | H | O | C | H | C | H | C | OCF2CHFOCF2CF2CF3 | H | H |
| 549 | COOCH3 | Me | Me | H | F | H | O | C | H | C | H | C | OCF2CHFOCF2CF2CF3 | H | H |
| 550 | COOCH3 | Me | Et | H | F | H | O | C | H | C | H | C | OCF2CHFOCF2CF2CF3 | H | H |
| 551 | Ac | Me | Me | F | F | H | O | C | H | C | H | C | OCF2CHFOCF2CF2CF3 | H | H |
| 552 | COOCH3 | Me | Et | H | Et | H | O | C | H | C | H | C | OCF2CHFOCF2CF2CF3 | H | H |
| 553 | COOCH3 | Me | Et | H | Me | H | OCH2 | C | H | C | H | C | OCF2CHFOCF2CF2CF3 | H | H |
| 554 | Ac | Me | Me | H | Me | H | OCH2 | C | H | C | H | C | OCF2CHFOCF2CF2CF3 | H | H |
| 555 | COOCH3 | Me | Et | H | Me | H | O(CH2)3O | C | H | C | H | C | OCF2CHFOCF2CF2CF3 | H | H |
| 556 | Ac | Me | Me | H | Me | H | O(CH2)3O | C | H | C | H | C | OCF2CHFOCF2CF2CF3 | H | H |
| 557 | COOCH3 | Me | Et | Me | Me | H | O | C | H | C | H | C | OCH2CH=CCl2 | H | H |
| 558 | COOCH3 | Me | Et | H | Me | H | O | C | H | C | H | C | OCH2CH=CCl2 | H | H |
| 559 | COOCH3 | Me | Et | Me | Me | H | O | C | H | C | H | C | OCH2CH=C(CF3)Cl | H | H |
| 560 | COOCH3 | Me | Et | H | Me | H | O | C | H | C | H | C | OCH2CH=C(CF3)Cl | H | H |
| 561 | COOCH3 | Me | Et | Me | Me | H | O | C | H | C | H | C | CH=C(CF3)Cl | H | H |
| 562 | COOCH3 | Me | Et | H | Me | H | O | C | H | C | H | C | CH=C(CF3)Cl | H | H |
| 563 | COOCH3 | Me | Et | Me | Me | H | O | C | H | C | H | C | CH=C(CF3)2 | H | H |
| 564 | COOCH3 | Me | Et | H | Me | H | O | C | H | C | H | C | CH=C(CF3)2 | H | H |
| 565 | COOCH3 | Me | Et | H | Me | H | O | C | H | C | H | C | OCF(CF3)2 | H | H |
| 566 | COOCH3 | Me | Et | Me | Me | H | O | C | H | C | H | C | OCF(CF3)2 | H | H |
| 567 | COOCH3 | Me | Et | H | Me | H | O | C | H | C | H | C | OCH(CF3)CH3 | H | H |
| 568 | COOCH3 | Me | Et | Me | Me | H | O | C | H | C | H | C | OCH(CF3)CH3 | H | H |
| 569 | COOCH3 | Me | Me | H | F | H | O | C | H | C | Cl | C | Cl | H | H |
| 570 | COOCH3 | Me | Me | COOMe | H | H | O | C | H | C | H | C | Cl | H | H |
| 571 | COOCH3 | Me | Me | F | F | H | O | C | H | C | H | C | Cl | H | H |

TABLE 12

| Compound No. | R1 | R2 | R3 | X1 | X2 | X3 | Z | W1 Y1 | | W2 Y2 | | W3 | Y3 | Y4 | Y5 |
|---|---|---|---|---|---|---|---|---|---|---|---|---|---|---|---|
| 572 | Ac | Me | Me | H | F | H | O | C | H | C | H | C | COOEt | H | H |
| 573 | Ac | Me | Me | F | H | H | O | C | H | C | H | C | COOEt | H | H |
| 574 | Ac | Me | Me | Me | H | H | O | C | H | C | H | C | Me | H | H |
| 575 | Ac | Me | Me | H | Me | H | O | C | H | C | H | C | Me | H | H |
| 576 | COOCH3 | Me | Me | H | F | H | O | C | H | C | Me | C | Me | H | H |
| 577 | Ac | Me | Me | H | F | H | O | C | H | C | H | C | Et | H | H |
| 578 | COOCH3 | Me | Me | H | F | H | O | C | H | C | H | C | SCF3 | H | H |
| 579 | COOCH3 | Me | Me | F | F | H | O | C | H | C | H | C | SCF3 | H | H |
| 580 | Ac | Me | Me | F | F | H | O | C | H | C | H | C | SCF3 | H | H |
| 581 | Ac | Me | Me | H | F | H | O | C | H | C | H | C | SCF3 | H | H |
| 582 | COOCH3 | Me | Me | F | H | H | O | C | H | C | H | C | SCF3 | H | H |
| 583 | Ac | Me | Me | H | OMe | H | O | C | H | C | H | C | SCF3 | H | H |
| 584 | COOCH3 | Me | Et | H | OMe | H | O | C | H | C | H | C | SCF3 | H | H |
| 585 | COOCH3 | Me | Me | COOMe | H | H | O | C | H | C | H | C | SCF3 | H | H |
| 586 | Ac | Me | Me | F | H | H | O | C | H | C | H | C | SCF3 | H | H |
| 587 | Ac | Me | Me | H | Et | H | O | C | H | C | H | C | SCF3 | H | H |
| 588 | COOCH3 | Me | Et | H | Et | H | O | C | H | C | H | C | SCF3 | H | H |
| 589 | COOCH3 | Me | Et | Me | Me | H | O | C | H | C | H | C | SCH2CH=CCl2 | H | H |
| 590 | COOCH3 | Me | Et | H | Me | H | O | C | H | C | H | C | SCH2CH=CCl2 | H | H |
| 591 | COOCH3 | Me | Et | Me | Me | H | O | C | H | C | H | C | SCH2CH2CF=CF2 | H | H |
| 592 | COOCH3 | Me | Et | Me | Me | H | O | C | H | C | H | C | SO2CF3 | H | H |
| 593 | COOCH3 | Me | Et | Me | Me | H | O | C | Cl | C | H | C | SO2CF3 | H | H |
| 594 | COOCH3 | Me | Et | H | Me | H | O | C | H | C | H | C | SO2CF3 | H | H |
| 595 | Ac | Me | Et | H | Me | H | O | C | H | C | H | C | SO2CF3 | H | H |
| 596 | Ac | Me | Me | H | Me | H | O | C | H | C | H | C | SO2CF3 | H | H |

TABLE 12-continued

| Compound No. | R1 | R2 | R3 | X1 | X2 | X3 | Z | W1 Y1 | | W2 Y2 | | W3 Y3 | Y4 | Y5 |
|---|---|---|---|---|---|---|---|---|---|---|---|---|---|---|
| 597 | Ac | Me | Et | Me | Me | H | O | C | H | C | H | C | SO2CF3 | H | H |
| 598 | Ac | Me | Me | Me | Me | H | O | C | H | C | H | C | SO2CF3 | H | H |
| 599 | Ac | Me | Me | H | MeO | H | O | C | H | C | H | C | SO2CF3 | H | H |
| 600 | COOCH3 | Me | Et | H | MeO | H | O | C | H | C | H | C | SO2CF3 | H | H |
| 601 | Ac | Me | Me | H | F | H | O | C | H | C | H | C | SO2CF3 | H | H |
| 602 | COOCH3 | Me | Me | H | F | H | O | C | H | C | H | C | SO2CF3 | H | H |
| 603 | COOCH3 | Me | Et | H | F | H | O | C | H | C | H | C | SO2CF3 | H | H |
| 604 | Ac | Me | Me | F | F | H | O | C | H | C | H | C | SO2CF3 | H | H |
| 605 | COOCH3 | Me | Et | H | Et | H | O | C | H | C | H | C | SO2CF3 | H | H |
| 606 | COOCH3 | Me | Et | H | Me | H | O | C | Cl | C | H | C | SO2CF3 | H | H |
| 607 | Ac | Me | Et | H | Me | H | O | C | Cl | C | H | C | SO2CF3 | H | H |
| 608 | Ac | Me | Me | H | Me | H | O | C | Cl | C | H | C | SO2CF3 | H | H |
| 609 | Ac | Me | Et | Me | Me | H | O | C | Cl | C | H | C | SO2CF3 | H | H |
| 610 | Ac | Me | Me | Me | Me | H | O | C | Cl | C | H | C | SO2CF3 | H | H |
| 611 | Ac | Me | Me | H | OMe | H | O | C | H | C | CF3 | C | H | H | H |
| 612 | COOCH3 | Me | Et | H | OMe | H | O | C | H | C | CF3 | C | H | H | H |
| 613 | COOCH3 | Me | Me | COOMe | H | H | O | C | H | C | CF3 | C | H | H | H |
| 614 | Ac | Me | Me | F | H | H | O | C | H | C | CF3 | C | H | H | H |
| 615 | COOCH3 | Me | Me | H | F | H | O | C | H | C | CF3 | C | H | H | H |
| 616 | COOCH3 | Me | Me | F | F | H | O | C | H | C | CF3 | C | H | H | H |
| 617 | COOCH3 | Me | Me | H | F | H | O | C | H | C | OCF3 | C | H | H | H |
| 618 | COOCH3 | Me | Me | F | H | H | O | C | H | C | OCF3 | C | H | H | H |
| 619 | Ac | Me | Me | H | OMe | H | O | C | H | C | OCF3 | C | H | H | H |
| 620 | COOCH3 | Me | Et | H | OMe | H | O | C | H | C | OCF3 | C | H | H | H |
| 621 | COOCH3 | Me | Me | COOMe | H | H | O | C | H | C | OCF3 | C | H | H | H |
| 622 | Ac | Me | Me | F | H | H | O | C | H | C | OCF3 | C | H | H | H |
| 623 | COOCH3 | Me | Me | F | F | H | O | C | H | C | OCF3 | C | H | H | H |

TABLE 13

| Compound No. | R1 | R2 | R3 | X1 | X2 | X3 | Z | W1 Y1 | | W2 Y2 | | W3 Y3 | Y4 | Y5 |
|---|---|---|---|---|---|---|---|---|---|---|---|---|---|---|
| 624 | Ac | Me | Me | H | Et | H | O | C | H | C | OCF3 | C | H | H | H |
| 625 | COOCH3 | Me | Et | H | Et | H | O | C | H | C | OCF3 | C | H | H | H |
| 626 | Ac | Me | Me | H | OMe | H | O | C | H | C | OCF2CHF2 | C | H | H | H |
| 627 | COOCH3 | Me | Et | H | OMe | H | O | C | H | C | OCF2CHF2 | C | H | H | H |
| 628 | COOCH3 | Me | Me | COOMe | H | H | O | C | H | C | OCF2CHF2 | C | H | H | H |
| 629 | Ac | Me | Me | F | H | H | O | C | H | C | OCF2CHF2 | C | H | H | H |
| 630 | COOCH3 | Me | Me | H | F | H | O | C | H | C | OCF2CHF2 | C | H | H | H |
| 631 | COOCH3 | Me | Me | F | F | H | O | C | H | C | OCF2CHF2 | C | H | H | H |
| 632 | Ac | Me | Me | H | Et | H | O | C | H | C | OCF2CHF2 | C | H | H | H |
| 633 | COOCH3 | Me | Et | H | Et | H | O | C | H | C | OCF2CHF2 | C | H | H | H |
| 634 | COOCH3 | Me | Me | H | F | H | O | C | H | C | SCF3 | C | H | H | H |
| 635 | Ac | Me | Me | H | F | H | O | C | H | C | SCF3 | C | H | H | H |
| 636 | COOCH3 | Me | Me | F | H | H | O | C | H | C | SCF3 | C | H | H | H |
| 637 | Ac | Me | Me | H | OMe | H | O | C | H | C | SCF3 | C | H | H | H |
| 638 | COOCH3 | Me | Et | H | OMe | H | O | C | H | C | SCF3 | C | H | H | H |
| 639 | COOCH3 | Me | Me | COOMe | H | H | O | C | H | C | SCF3 | C | H | H | H |
| 640 | Ac | Me | Me | F | H | H | O | C | H | C | SCF3 | C | H | H | H |
| 641 | COOCH3 | Me | Me | F | F | H | O | C | H | C | SCF3 | C | H | H | H |
| 642 | Ac | Me | Me | H | Et | H | O | C | H | C | SCF3 | C | H | H | H |
| 643 | COOCH3 | Me | Et | H | Et | H | O | C | H | C | SCF3 | C | H | H | H |
| 644 | Ac | Me | Me | Me | H | H | O | C | OCF3 | C | H | C | H | H | H |
| 645 | Ac | Me | Me | H | Me | H | O | C | OCF3 | C | H | C | H | H | H |
| 646 | Ac | Me | Me | CF3 | H | H | O | C | OCF3 | C | H | C | H | H | H |
| 647 | Ac | Me | Me | H | CF3 | H | O | C | OCF3 | C | H | C | H | H | H |
| 648 | COOCH3 | Me | Et | H | Me | H | O | C | H | C—O—CF2—CF2—O—C | | | H | H | H |
| 649 | COOCH3 | Me | Et | Me | H | H | O | C | H | C—O—CF2—CF2—O—C | | | H | H | H |
| 650 | COOCH3 | Me | Me | H | F | H | O | C | H | C—O—CF2—CF2—O—C | | | H | H | H |
| 651 | Ac | Me | Me | H | F | H | O | C | H | C—O—CF2—CF2—O—C | | | H | H | H |
| 652 | COOCH3 | Me | Me | F | H | H | O | C | H | C—O—CF2—CF2—O—C | | | H | H | H |
| 653 | COOCH3 | Me | Et | Me | Me | H | O | C | H | C—O—CF2—CF2—O—C | | | H | H | H |
| 654 | H | Me | Et | H | Me | H | O | C | H | C—O—CF2—CF2—O—C | | | H | H | H |
| 655 | Ac | Me | Et | H | Me | H | O | C | H | C—O—CF2—CF2—O—C | | | H | H | H |
| 656 | Ac | Me | Me | H | Me | H | O | C | H | C—O—CF2—CF2—O—C | | | H | H | H |
| 657 | Ac | Me | Et | Me | Me | H | O | C | H | C—O—CF2—CF2—O—C | | | H | H | H |
| 658 | Ac | Me | Me | Me | Me | H | O | C | H | C—O—CF2—CF2—O—C | | | H | H | H |
| 659 | Ac | Me | Me | H | MeO | H | O | C | H | C—O—CF2—CF2—O—C | | | H | H | H |
| 660 | COOCH3 | Me | Et | H | MeO | H | O | C | H | C—O—CF2—CF2—O—C | | | H | H | H |
| 661 | COOCH3 | Me | Et | H | Et | H | O | C | H | C—O—CF2—CF2—O—C | | | H | H | H |

TABLE 13-continued

| Compound No. | R1 | R2 | R3 | X1 | X2 | X3 | Z | W1 Y1 | W2 Y2 | W3 Y3 | Y4 | Y5 |
|---|---|---|---|---|---|---|---|---|---|---|---|---|
| 662 | COOCH3 | Me | Et | H | Me | H | OCH2 | C H | C—O—CF2—CF2—O—C | | H | H |
| 663 | Ac | Me | Me | H | Me | H | OCH2 | C H | C—O—CF2—CF2—O—C | | H | H |
| 664 | COOCH3 | Me | Et | H | Me | H | O(CH2)3O | C H | C—O—CF2—CF2—O—C | | H | H |
| 665 | Ac | Me | Me | H | Me | H | O(CH2)3O | C H | C—O—CF2—CF2—O—C | | H | H |
| 666 | COOCH3 | Me | Me | H | Me | H | O | C H | C—CF2—CF2—O—C | | H | H |
| 667 | COOCH3 | Me | Et | H | Me | H | O | C H | C—CF2—CF2—O—C | | H | H |
| 668 | COOCH3 | Me | Et | Me | Me | H | O | C H | C—CF2—CF2—O—C | | H | H |
| 669 | Ac | Me | Me | H | Me | H | O | C H | C—O—CF2—CF2—CH2—C | | H | H |
| 670 | COOCH3 | Me | Et | H | Me | H | O | C H | C—O—CF2—CF2—CH2—C | | H | H |
| 671 | Ac | Me | Me | H | Me | H | O | C H | C—CH2—CF2—CF2—O—C | | H | H |
| 672 | COOCH3 | Me | Et | H | Me | H | O | C H | C—CH2—CF2—CF2—O—C | | H | H |
| 673 | Ac | Me | Me | H | Me | H | O | C H | C—S—CF2—CF2—S—C | | H | H |
| 674 | COOCH3 | Me | Et | H | Me | H | O | C H | C—S—CF2—CF2—S—C | | H | H |
| 675 | Ac | Me | Me | H | Me | H | O | C H | C—CF2—CF2—S—C | | H | H |

TABLE 14

| Compound No. | R1 | R2 | R3 | X1 | X2 | X3 | Z | W1 Y1 | W2 Y2 | W3 Y3 | Y4 | Y5 |
|---|---|---|---|---|---|---|---|---|---|---|---|---|
| 676 | COOCH3 | Me | Et | H | Me | H | O | C H | C—CF2—CF2—S—C | | H | H |
| 677 | Ac | Me | Me | H | Me | H | O | C H | C—CF2—CF2—CF2—C | | H | H |
| 678 | COOCH3 | Me | Et | H | Me | H | O | C H | C—CF2—CF2—CF2—C | | H | H |
| 679 | Ac | Me | Me | Cl | H | H | O | N | C H | C Cl | H | H |
| 680 | Ac | Me | Me | H | Cl | H | O | N | C H | C Cl | H | H |
| 681 | Ac | Me | Me | CF3 | H | H | O | N | C H | C CF3 | H | Cl |
| 682 | Ac | Me | Me | H | CF3 | H | O | N | C H | C CF3 | H | Cl |
| 683 | COOCH3 | Me | Et | Me | Me | H | O(CH2)3O | N | C H | C CF3 | H | H |
| 684 | Ac | Me | Me | Me | Me | H | O | N | C H | C CF3 | H | Cl |
| 685 | COOCH3 | Me | Et | Me | Me | H | O | N | C H | C CF3 | H | Cl |
| 686 | Ac | Me | Me | H | Me | H | O | N | C H | C CF3 | H | H |
| 687 | COOCH3 | Me | Me | H | Me | H | O | N | C H | C CF3 | H | H |
| 688 | Ac | Me | Me | Me | Me | H | O | N | C H | C CF3 | H | H |
| 689 | COOCH3 | Me | Et | Me | Me | H | O | N | C H | C CF3 | H | H |
| 690 | Ac | Me | Me | H | MeO | H | O | N | C H | C CF3 | H | H |
| 691 | COOCH3 | Me | Et | H | MeO | H | O | N | C H | C CF3 | H | H |
| 692 | Ac | Me | Me | H | F | H | O | N | C H | C CF3 | H | H |
| 694 | COOCH3 | Me | Et | H | Me | H | O | C H | N | C CF3 | H | H |
| 695 | Ac | Me | Me | Me | Me | H | O | C H | N | C CF3 | H | H |
| 696 | COOCH3 | Me | Et | Me | Me | H | O | C H | N | C CF3 | H | H |
| 697 | Ac | Me | Me | H | MeO | H | O | C H | N | C CF3 | H | H |
| 698 | COOCH3 | Me | Et | H | MeO | H | O | C H | N | C CF3 | H | H |
| 699 | Ac | Me | Me | H | F | H | O | C H | N | C CF3 | H | H |
| 700 | COOCH3 | Me | Me | H | F | H | O | N | C H | C CF3 | H | Cl |

Agriculturally and horticulturally acceptable acid addition salts in the compounds of formula (I) or formula (Ia) include, for example, hydrochlorides, nitrates, sulfates, phosphates, or acetates.

Compounds represented by formula (I) or formula (Ia) may be produced by the process shown in the following scheme. Specifically, compounds represented by formula (Ib), which are compounds represented by formula (I) or formula (Ia) wherein $R_1$ represents $COR_4$, may be provided by the process described in Japanese Patent No. 2633377. In the following scheme, $R_2$, $R_3$, and $R_4$, $X_1$, $X_2$, and $X_3$, $Y_1$, $Y_2$, $Y_3$, $Y_4$, and $Y_5$, and Z are as defined above, $Y_1$, $Y_2$, $Y_3$, $Y_4$, and $Y_5$ may be $Y_{11}$, $Y_{12}$, $Y_{13}$, $Y_{14}$, and $Y_{15}$ in compound represented by formula (Ia).

Compounds represented by formula (1b) may be synthesized by reacting a compound represented by formula (2) with a reagent represented by formula (3a) or formula (3b) in the presence or absence of a base and optionally subjecting the reaction product to a substituent exchange.

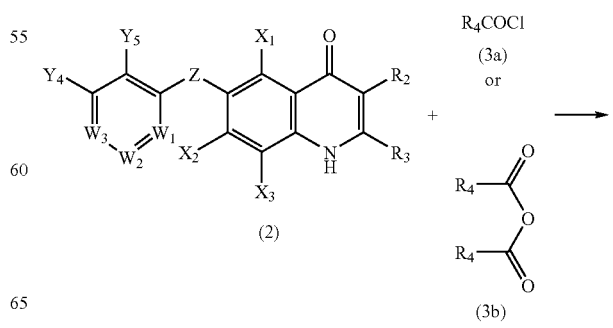

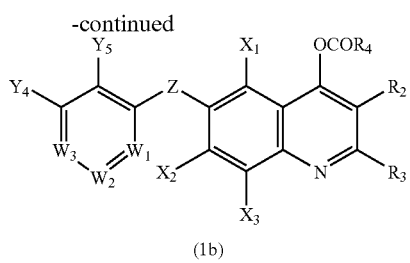

(1b)

Compounds represented by formula (1c), which are compounds represented by formula (I) or formula (Ia) wherein $R_1$ represents $R_1'$ which represents optionally substituted $C_{1-18}$ alkyl, optionally substituted $C_{2-18}$ alkenyl, optionally substituted $C_{2-18}$ alkynyl, optionally substituted $C_{3-10}$ cycloalkyl, optionally substituted phenyl lower alkyl, optionally substituted phenoxy lower alkyl, optionally substituted phenyl, optionally substituted hetero ring, may be synthesized by reacting a compound represented by formula (2) wherein $R_1$ represents a hydrogen atom with a compound represented by formula (3c), or reacting a compound represented by formula (4) wherein $R_1$ represents a chlorine atom with a compound represented by formula (3d), in an organic solvent, for example, methanol, ethanol, acetone, ethyl acetate, benzene, chloroform, dichloromethane, tetrahydrofuran, or dimethylformamide in the presence or absence of a base and optionally subjecting the reaction product to a substituent exchange. The compound represented by formula (4) wherein $R_1$ represents a chlorine atom may be prepared by reacting the compound represented by formula (2) with a halogenating agent such as thionyl chloride, oxalyl chloride, or phosphorus oxychloride, in an organic solvent or in the absence of a solvent.

The compound represented by formula (2) as a starting compound may be produced by a conventional method, J. Am. Chem. Soc. 70, 2402 (1948) or Tetrahedron Lett. 27, 5323 (1986). In the following scheme, $R_9$ represents $C_{1-4}$ lower alkyl.

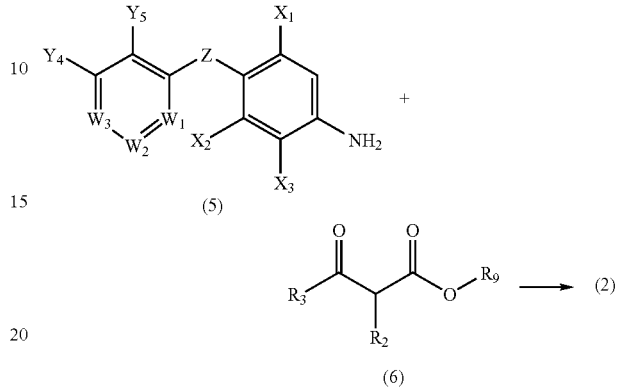

The compound represented by formula (2) is a tautomer of a compound represented by formula (I) or formula (Ia) wherein $R_1$ represents a hydrogen atom. That is, the compound represented by formula (I) or formula (Ia) wherein $R_1$ represents a hydrogen atom may be produced according to the above scheme.

Further, compounds represented by formula (5) may be produced by reducing a nitro group in a compound represented by formula (7) according to the following scheme.

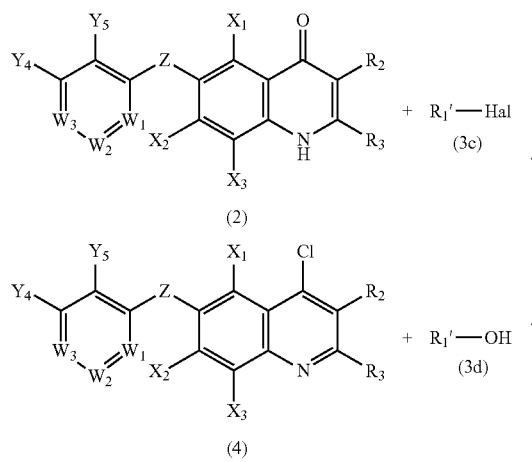

Here bases include, for example, organic amines such as triethylamine or pyridine, and inorganic alkalis such as sodium carbonate, potassium carbonate, and sodium hydride.

Compounds represented by formula (I) or formula (Ia) wherein $R_1$ represents an alkali metal or an alkaline earth metal may be produced by mixing and reacting a compound represented by formula (I) or formula (Ia) wherein $R_1$ represents a hydrogen atom or $COR_4$ with a base such as a hydroxide, hydride, alkylate or the like of an alkali metal or alkaline earth metal, for example, sodium hydroxide, potassium hydroxide, sodium hydride, or butyllithium, in an organic solvent, for example, methanol, ethanol, acetone, ethyl acetate, benzene, chloroform, dichloromethane, or tetrahydrofuran.

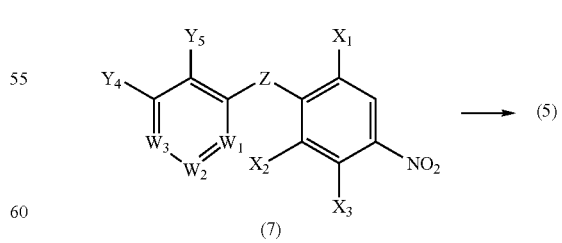

Compounds represented by formula (7a) which are compounds represented by formula (7) wherein Z represents an oxygen atom may be produced from a compound represented by formula (8a) and a compound represented by formula (9a), from a compound represented by formula (8b) and a compound represented by formula (9b), or from a compound represented by formula (8c) and a compound represented by formula (9c), by the method shown in the following scheme.

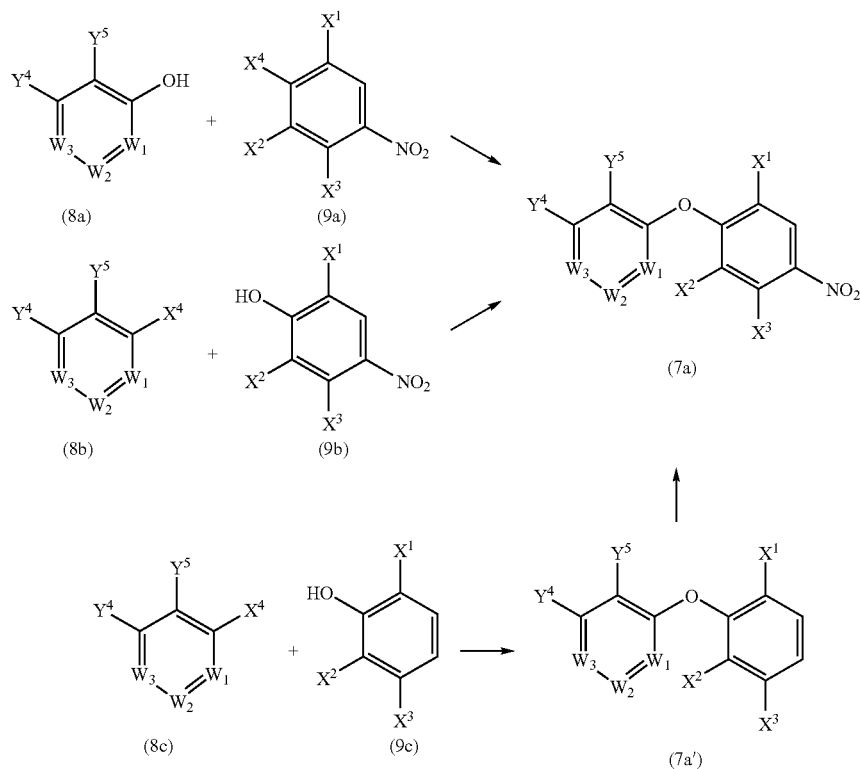

Specifically, compounds as phenyl ether derivatives represented by formula (7a) are synthesized by reacting a generally available phenol derivative represented by formula (8a) with a nitrated compound represented by formula (9a), or reacting a generally available nitrophenol derivative represented by formula (9b) with a halogenated aryl compound represented by formula (8b), in the presence or absence of a base, or by reacting a generally available phenol derivative represented by formula (9c) with a halogenated aryl compound represented by formula (8c) in the presence or absence of a base, and nitrating the compound as a phenyl ether derivative represented by formula (7a'). Here $X_4$ represents a halogen atom such as chlorine, bromine, iodine, or fluorine.

Compounds represented by formula (7b) which are compounds represented by formula (7) wherein Z represents a sulfur element may be synthesized by reacting a compound represented by formula (10) with a compound represented by formula (9).

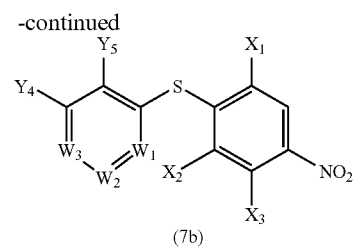

Compounds represented by formula (7c) which are compounds represented by formula (7) wherein Z represents SO, or compounds represented by formula (7d) which are compounds represented by formula (7) wherein Z represents $SO_2$ may be synthesized by oxidizing a compound represented by formula (7b).

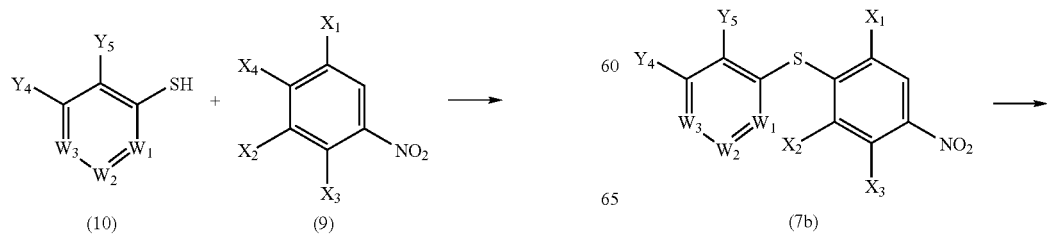

-continued

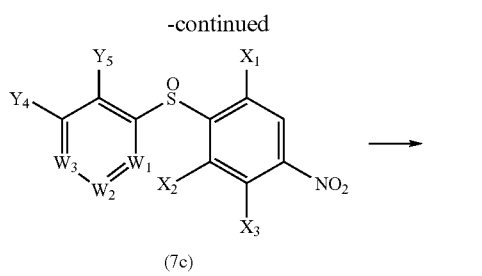

(7c)

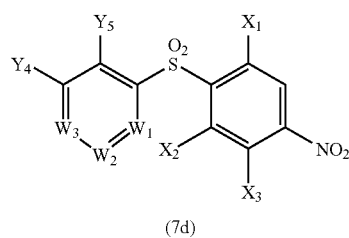

(7d)

Compounds represented by formula (7e) which are compounds represented by formula (7) wherein Z represents OCH$_2$ may be synthesized by reacting a compound represented by formula (11) with a compound represented by formula (9).

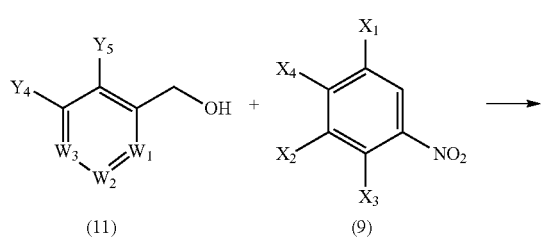

(11)  (9)

-continued

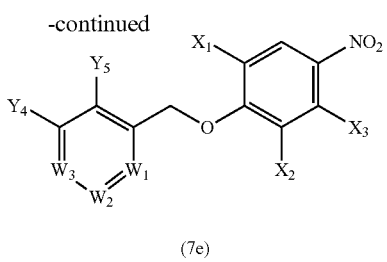

(7e)

Compounds represented by formula (7f) which are compounds represented by formula (7) wherein Z represents CO may be synthesized by a Friedel-Crafts reaction using a compound represented by formula (12) and a compound represented by formula (13).

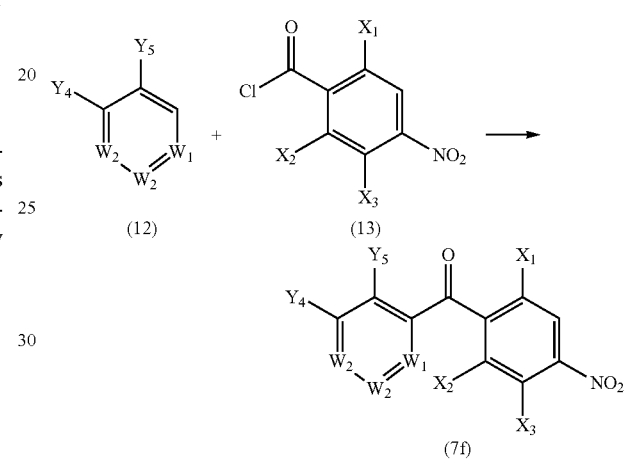

(12)  (13)

(7f)

Compounds represented by formula (5g) which are compounds represented by formula (5) wherein Z represents CH$_2$ may be synthesized by a route through a compound represented by formula (7g) produced by reducing CO in formula (7f), or by a route through a compound represented by formula (5f) produced by reducing a nitro group in formula (7f).

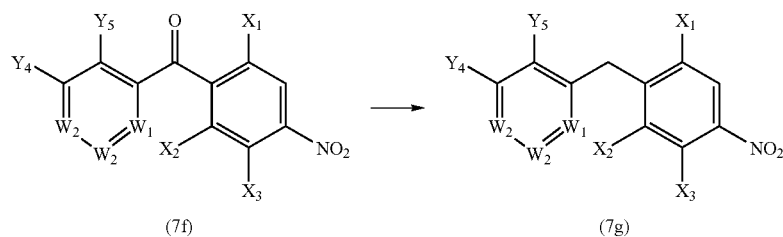

(7f)  (7g)

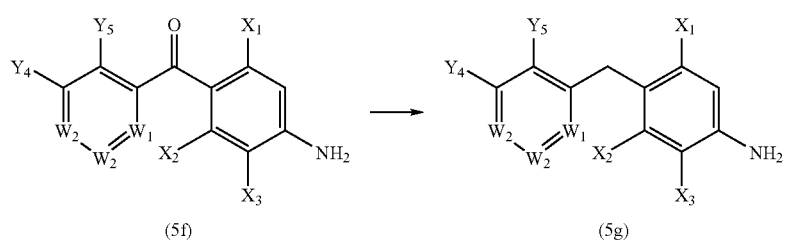

(5f)  (5g)

Compounds represented by formula (7h) which are compounds represented by formula (7) wherein Z represents a bond may be synthesized by reacting a compound represented by formula (14) with a compound represented by formula (9).

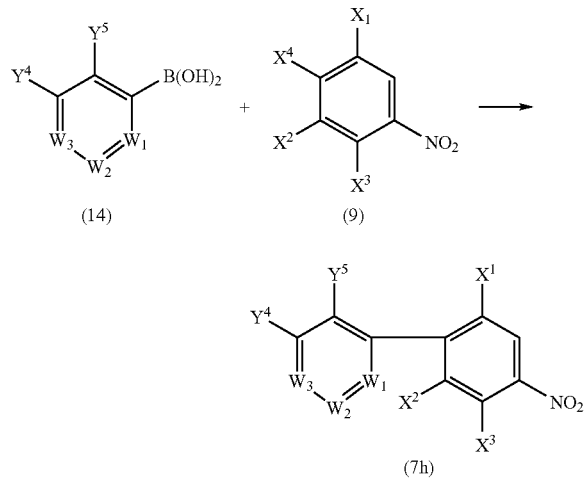

Compounds represented by formula (7i) which are compounds represented by formula (7) wherein Z represents —O-Q-O— may be synthesized by reacting a compound represented by formula (9) with a compound represented by formula (15) to give a compound represented by formula (16) and reacting the compound with a compound represented by formula (8). Here $X_5$ and $X_6$ represent a halogen atom such as chlorine, bromine, iodine, or fluorine.

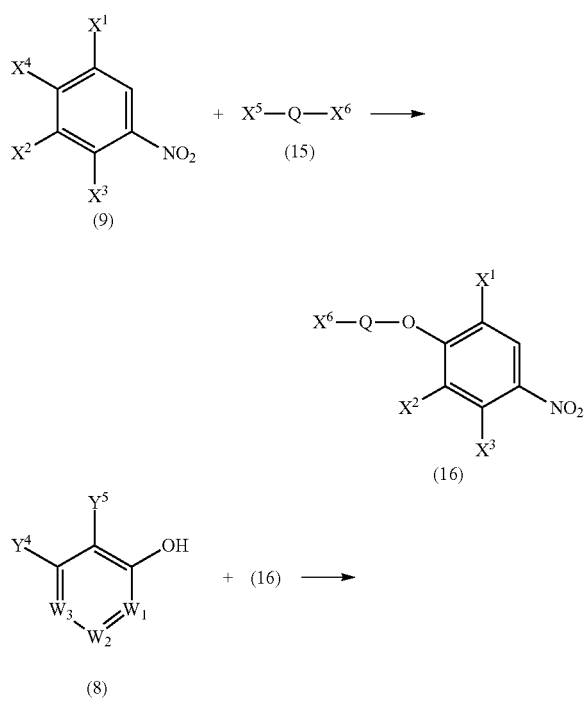

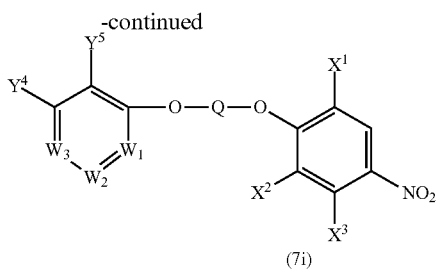

Agricultural and Horticultural Insecticide

As is apparent from the following Examples, the compounds represented by formula (I) or formula (Ia) have excellent control effect against insect pests. Accordingly, according to the present invention, there is provided an agricultural and horticultural insecticide comprising a compound represented by formula (I) or formula (Ia) as an active ingredient. The agricultural and horticultural insecticide according to the present invention may comprise an agriculturally and horticulturally acceptable acid addition salt of the compound represented by formula (I) or formula (Ia) as an active ingredient.

Insect pest species as targets to be controlled in the present invention (insect pest species against which the compounds represented by formula (I) or formula (Ia) have control effect) are not particularly limited, and preferred insect pest species include *Lepidopteran* insect pests (for example, *Noctuidae* such as *Spodoptera litura, Spodoptera exigua, Pseudaletia separata, Mamestra brassicae, Agrotis ipsilon, Trichoplusia* spp., *Heliothis* spp., and *Helicoverpa* spp.; *Pyralidae* such as *Chilo suppressalis, Cnaphalocrocis medinalis, Ostrinia nubilalis* (European cornborer), *Hellula undalis, Parapediasia teterrella, Haritalodes derogatus*, and *Plodia interpunctella*; *Pieridae* such as *Pieris rapae*; *Tortricidae* such as *Adoxophyes* spp., *Grapholita molesta*, and *Cydia pomonella*; Carposinidae such as *Carposina niponensis*; Lyonetiidae such as *Lyonetia* spp.; Lymantriidae such as *Lymantria* spp. and *Euproctis* spp.; Yponomeutidae such as *Plutella xylostella*; Gelechiidae such as *Pectinophora gossypiella*; Arctiidae such as *Hyphantria cunea*; Tineidae such as *Tinea translucens* and *Tineola bisselliella* and the like), *Hemipteran* insect pests (for example, Aphididae such as *Myzus persicae* and *Aphis gossypii*; Delphacidae such as *Laodelphax striatellus, Nilaparvata lugens* and *Sogatella furcifera*; Deltocephalidae such as *Nephotettix cincticeps*; Pentatomidae such as *Trigonotylus caelestialium, Plautia crossota stali, Nezara viridula* and *Riptortus clavatus*; Aleyrodidae such as *Trialeurodes vaporariorum*, and *Bemisia argentifolli* (silverleaf whitefly); Coccoidea such as *Pseudococcus comstocki*; Tingidae; Psyllidae and the like), *Coleoptera* insect pests (for example, Curculionidae such as *Sitophilus zeamais* (maize weevil), *Lissorhoptrus oryzophilus, Callosobruchuys chienensis*; Tenebrionidae such as *Tenebrio molitor*; Scarabaeidae such as *Anomala cuprea* and *Anomala rufocuprea*; Chrysomelidae such as *Phyllotreta striolata, Aulacophora femoralis, Leptinotarsa decemlineata* (Colorado Potato Beetle), *Diabrotica virgifera virgifera* (Western Corn Rootworm), and *Diabrotica undecimpunctata howardi* (Southern Corn Rootworm); Epilachna such as *Oulema oryzae, Paederus fuscipes*, Bostrychidae, and *Epilachna vigintioctopunctata*; Cerambycidae and the like), *Acarina* insect pests (for example, Tetranychidae such as *Tetranychus urticae, Tetranychus kanzawai, Panonychus citri, Panonychus ulmi*, and *Oligonychus* spp.; Eriophyidae such as *Aculops lycopersici, Aculops pelekassi*, and *Calacarus carinatus*; Tarsonemidae such as *Polyphagotarsonemus latus; Acaridae* and the like), Hymenopteran insect pests (for example, *Tenthredinidae* such as *Athalia rosae ruficornis* and the like), Orthopteran insect pests (for example, *Acrididae* and the like), Dipteran insect pests (for example, *Muscidae; Culex; Anopheles; Chironomidae; Calliphoridae; Sarcophagidae; Fannia canicularis; Anthomyiidae; Agromyzidae* such as *Liriomyza trifohii, Liriomyza sativae*, and *Liriomyza bryoniae; Tephritidae; Phoridae; Drbsophilidae; Psychodidae; Simuliidae; Tabanidae; Stomoxys calcitrans* and the like), Thysanopteran insect pests (for example, *Thrips palmi, Frankliniella occidentalis, Thrips tabaci, Thrips hawaiiensis, Scirtothrips dorsalis, Frankliniella intonsa, Ponticulothrips diospyrosi* and the like), Plant Parasitic Nematodes (for example, *Meloidogyne; Pratylenchus; Heterodera*; and *Aphelenchoides* such as *Aphelenchoides besseyi; Bursaphelenchus xylophilus* and the like), more preferably Lepidopteran insect pests, Hemipteran insect pests, Coleoptera insect pests, Acarina insect pests, Dipteran insect pests, or Thysanopteran insect pests. In an embodiment using the compounds represented by formula (II) or formula (IIa) or agriculturally and horticulturally acceptable acid addition salts thereof, target insect pests are preferably Lepidopteran insect pests, Hemipteran insect pests, Acarina insect pests, or Thysanopteran insect pests.

When the compounds represented by formula (I) or formula (Ia) are used as an agricultural and horticultural insecticide, the compounds represented by formula (I) or formula (Ia) as such may be used. Alternatively, the compounds represented by formula (I) or formula (Ia) may be mixed with suitable solid carriers, liquid carriers, gaseous carriers or the like, surfactants, dispersants and other adjuvants for formulations, to prepare any suitable formulation, such as emulsifiable concentrates, EW formulation, liquid formulations, suspension, wettable powder, granular wettable powder, dust, DL (low drift) dust, fine subtilaes, granules, tablets, oil solutions, aerosols, floables, dry floables, and microcapsules.

Accordingly, according to another aspect of the present invention, there is provided use of a compound represented by formula (I) or an agriculturally and horticulturally acceptable acid addition salt thereof as an agricultural and horticultural insecticide.

According to a further aspect of the present invention, there is provided use of a compound represented by formula (Ia) or an agriculturally and horticulturally acceptable acid addition salt thereof as an agricultural and horticultural insecticide.

Solid carriers usable herein include, for example, talc, bentonite, clay, kaolin, diatomaceous earth, vermiculite, white carbon, calcium carbonate, acid clay, silica sand, silica stone, zeolite, pearlite, attapulgite, pumice, ammonium sulfate, sodium sulfate, and urea.

Examples of liquid carriers include: alcohols, such as methanol, ethanol, n-hexanol, ethylene glycol, and propylene glycol; ketones, such as acetone, methyl ethyl ketone, and cyclohexanone; aliphatic hydrocarbons, such as n-hexane, kerosine, and kerosene; aromatic hydrocarbons, such as toluene, xylene, and methyinaphthalene; ethers, such as diethyl ether, dioxane, and tetrahydrofuran; esters, such as ethyl acetate; nitriles, such as acetonitrile and isobutyronitrile; acid amides, such as dimethylformamide and dimethylacetamide; vegetable oils, such as soy bean oil and cotton seed oil; dimethylsulfoxide; and water.

Gaseous carriers include, for example, LPG, air, nitrogen, carbon dioxide, and dimethyl ether.

Surfactants and dispersants include, for example, alkylsulfonic esters, alkyl(aryl)sulfonic acid salts, polyoxyalkylene alkyl(aryl) ethers, polyhydric alcohol esters, lignin sulfonic acid salts, alkylsulfosuccinic acid salts, formalin condensates of alkylnaphthalenesulfonic acid salts, polycarboxylic acid salts, POE polystyryl phenyl ether sulfonic acid salts and POE polystyryl phenyl ether phosphoric acid salts, and POE-POP block polymers.

Adjuvants for formulations include, for example, carboxymethylcellulose, hydroxypropylcellulose, polyvinyl alcohol, xanthan gum, pregelatinized starch, gum arabic, polyethylene glycol, liquid paraffin, calcium stearate, and antifoaming agents and preservatives.

The above carriers, surfactants, dispersants, and adjuvants may be used either alone or in a combination of two or more according to need.

The content of the active ingredient in the formulation is not particularly limited. Preferably, however, the content of the active ingredient in the formulation is 1 to 75% by weight for emulsifiable concentrates; 0.3 to 25% by weight for dust; 1 to 90% by weight for wettable powder; and 0.5 to 10% by weight for granules.

The agricultural and horticultural insecticide according to the present invention may be used as such or after dilution. Further, the agricultural and horticultural insecticide according to the present invention may be used as a mixture or in a combination with, for example, other insecticides, fungicides, miticides, herbicides, plant growth-regulating agents, or fertilizers. Agents which may be mixed or used in combination include those described, for example, in The Pesticide Manual, 13th edition, published by The British Crop Protection Council and SHIBUYA INDEX, the 9th edition, 2002, published by SHIBUYA INDEX RESEARCH GROUP; and SHIBUYA INDEX, the 10th edition, 2005, published by SHIBUYA INDEX RESEARCH GROUP.

More specifically, insecticides usable herein include, for example, organophosphate compounds such as acephate, dichlorvos, EPN, fenitothion, fenamifos, prothiofos, profenofos, pyraclofos, chlorpyrifos-methyl, and diazinon; carbamate compounds such as methomyl, thiodicarb, aldicarb, oxamyl, propoxur, carbaryl, fenobucarb, ethiofencarb, fenothiocarb, pirimicarb, carbofuran, and benfuracarb; nereistoxin derivatives such as cartap and thiocyclam; organochlorine compounds such as dicofol and tetradifon; pyrethroid compounds such as permethrin, tefluthrin, cypermethrin, deltamethrin, cyhalothrin, fenvalerate, fluvalinate, ethofenprox, and silafluofen; benzoylurea compounds such as diflubenzuron, teflubenzuron, flufenoxuron, and chlorfluazuron; and juvenile hormone-like compounds such as methoprene. Other insecticides include buprofezin, hexythiazox, amitraz, chlordimeform, pyridaben, fenpyroxymate, pyrimidifen, tebufenpyrad, fluacrypyrim, acequinocyl, fipronyl, ethoxazole, imidacloprid, chlothianidin, pymetrozine, bifenazate, spirodiclofen, chlorfenapyr, pyriproxyfene, indoxacarb, pyridalyl, or spinosad, avermectin, milbemycin, organometallic compounds, dinitro compounds, organosulfur compounds, urea compounds, triazine compounds, hydrazine compounds or other compounds. The agricultural and horticultural insecticides according to the present invention may also be used as a mixture or in a combination with microbial pesticides such as BT formulations and insect pathological viral agents.

Fungicides usable herein include, for example, strobilrin compounds such as azoxystrobin, kresoxym-methyl, and trifloxystrobin; anilinopyrimidine compounds such as mepanipyrim, pyrimethanil, and cyprodinil; azole compounds such as triadimefon, bitertanol, triflumizole, etaconazole, propiconazole, penconazole, flusilazole, myclobutanil, cyproconazole, tebuconazole, hexaconazole, prochloraz, and simeconazole; quinoxaline compounds such as quinomethionate; dithiocarbamate compounds such as maneb, zineb, mancozeb, polycarbamate, and propineb; phenylcarbamate compounds such as diethofencarb; organochlorine compounds such as chlorothalonil and quintozene; benzimidazole compounds such as benomyl, thiophanate-methyl, and carbendazole; phenylamide compounds such as metalaxyl, oxadixyl, ofurase, benalaxyl, furalaxyl, and cyprofuram; sulfenic acid compounds such as dichlofluanid; copper compounds such as copper hydroxide and oxine-copper; isoxazole compounds such as hydroxyisoxazole; organophosphorus compounds such as fosetyl-aluminium and tolclofos-methyl; N-halogenothioalkyl compounds such as captan, captafol, and folpet; dicarboxyimide compounds such as procymidone, iprodione, and vinchlozolin; benzanilide compounds such as flutolanil and mepronil; morpholine compounds such as fenpropimorph and dimethomorph; organotin compounds such as fenthin hydroxide, and fenthin acetate; and cyanopyrrole compounds such as fludioxonil and fenpiclonil. Other fungicides include fthalide, fluazinam, cymoxanil, triforine, pyrifenox, fenarimol, fenpropidin, pencycuron, cyazofamid, iprovalicarb, and benthiavalicarb-isopropyl.

According to another aspect of the present invention, there is provided a method for controlling an agricultural and horticultural insect pest, comprising the step of applying an effective amount of a compound represented by formula (I) or an agriculturally and horticulturally acceptable acid addition salt thereof to a plant or soil. According to a further aspect of the present invention, there is provided a method for controlling an agricultural and horticultural insect pest, comprising the step of applying an effective amount of a compound represented by formula (Ia) or an agriculturally and horticulturally acceptable acid addition salt thereof to a plant or soil. The control method according to the present invention includes a method in which the compound represented by formula (I) or (Ia) or an agriculturally and horticulturally acceptable acid addition salt thereof is applied by smoking treatment in a sealed space.

EXAMPLES

The present invention is further illustrated by the following Examples that are not intended as a limitation of the invention.

Synthesis Example 1

4-Acetoxy-5-chloro-6-(4-chlorophenoxy)-2,3-dimethyl-quinoline (Compound No. 2) and 4-acetoxy-7-chloro-6-(4-chlorophenoxy)-2,3-dimethyl-quinoline (Compound No. 22)

A mixture composed of 2.2 g of 3-chloro-4-(4-chlorophenoxy)-aniline, 2.63 g of ethyl 2-methylacetoacetate, and 0.5 mL of ethanol was added dropwise to 3.8 g of polyphosphoric acid heated to 150° C. The mixed solution was stirred at 150 to 160° C. while removing ethanol by evaporation for 3 hr. The reaction solution was poured into 175 mL of iced water containing 2 mL of concentrated hydrochloric acid to produce crystals. The crystals were collected by filtration and were recrystallized from water/methanol to give 2.8 g of a mixture of 5-chloro-6-(4-chlorophenoxy)-4-hydroxy-2,3-dimethyl-quinoline with 7-chloro-6-(4-chlorophenoxy)-4-hydroxy-2,3-dimethyl-quinoline (yield 93%). The mixture (2.8 g) was stirred in 42 mL of acetic anhydride with heating at 120 to 125° C. for one hr. The reaction solution was concentrated, ethyl acetate was then added to the concentrate, the mixture was washed with a saturated aqueous sodium hydrogencarbonate solution and saturated brine, and the solvent was removed under the reduced pressure to give a crude product. The crude product was purified by column chromatography on silica gel (BW300, manufactured by Fuji Sylysia Chemical Ltd., solvent: n-hexane/ethyl acetate) to give 1.03 g of 4-acetoxy-5-chloro-6-(4-chlorophenoxy)-2,3-dimethyl-quinoline (yield 32.6%) and 0.68 g of 4-acetoxy-7-chloro-6-(4-chlorophenoxy)-2,3-dimethyl-quinoline (yield 21.0%).

Synthesis Example 2

4-Acetoxy-2,3-dimethyl-6-(4-trifluoromethoxyphenoxy)-5-trifluoromethyl-quinoline (Compound No. 90) and 4-acetoxy-2,3-dimethyl-6-(4-trifluoromethoxyphenoxy)-7-trifluoromethyl-quinoline (Compound No. 122)

A solution of 3.4 g of 4-(4-trifluoromethoxyphenoxy)-3-trifluoromethyl-aniline, 2.4 g of ethyl 2-methylacetoacetate, and 0.3 g of p-toluenesulfonic acid dissolved in 100 mL of xylene was heated under reflux for 36 hr. This reaction solution was cooled, and the precipitated crystals were collected by filtration to give 1.73 g of 2,3-dimethyl-4-hydroxy-6-(4-trifluoromethoxyphenoxy)-7-trifluoromethyl-quinoline. The filtrate was concentrated under the reduced pressure to give 2,3-dimethyl-4-hydroxy-6-(4-trifluoromethoxyphenoxy)-5-trifluoromethyl-quinoline. Acetic anhydride (40 mL) was added to 2,3-dimethyl-4-hydroxy-6-(4-trifluoromethoxyphenoxy)-5-trifluoromethyl-quinoline obtained from the filtrate, and the mixture was heated at 120 to 125° C. for one hr. This reaction solution was concentrated under the reduced pressure, ethyl acetate was then added to the concentrate, and the mixture was washed with brine. Thereafter, the solvent was removed under the reduced pressure, and the crude product was purified by column chromatography on silica gel (BW300, manufactured by Fuji Sylysia Chemical Ltd., solvent: n-hexane/ethyl acetate) to give 0.35 g of 4-acetoxy-2,3-dimethyl-6-(4-trifluoromethoxyphenoxy)-5-trifluoromethyl-quinoline.

Acetic anhydride (40 mL) was added to 1.73 g of 2,3-dimethyl-4-hydroxy-6-(4-trifluoromethoxyphenoxy)-7-trifluoromethyl-quinoline obtained as crystals, and the mixture was heated at 120 to 125° C. for one hr. This reaction solution was concentrated under the reduced pressure, ethyl acetate was then added to the concentrate, and the mixture was washed with brine. Thereafter, the solvent was removed under the reduced pressure, and the crude product was purified by column chromatography on silica gel (BW300, manufactured by Fuji Sylysia Chemical Ltd., solvent: n-hexane/ethyl acetate) to give 0.82 g of 4-acetoxy-2,3-dimethyl-6-(4-trifluoromethoxyphenoxy)-7-trifluoromethyl-quinoline.

Synthesis Example 3

5-Trifluoromethyl-6-(4-trifluoromethoxyphenoxy)-4-hydroxy-2,3-dimethyl-quinoline (Compound No. 89)

4-Acetoxy-5-trifluoromethyl-6-(4-trifluoromethoxyphenoxy)-2,3-dimethyl-quinoline (1.5 g) prepared in Synthesis Example 2 was dissolved in 10 mL of ethanol. A 20% sodium hydroxide solution (10 mL) was added to the solution, and the mixture was stirred at 50° C. for 3 hr. This reaction mixture was added to 20 mL of water, and the mixture was neutralized with 1 N hydrochloric acid. The precipitated crystals were collected by filtration under the reduced pressure to give 1.34 g of 5-trifluoromethyl-6-(4-trifluoromethoxyphenoxy)-4-hydroxy-2,3-dimethyl-quinoline (yield 98.0%).

Synthesis Example 4

4-Acetoxy-6-(2-chloro-4-trifluoromethylphenoxy)-2,3-dimethyl-5-trifluoromethyl-quinoline (Compound No. 222) and 4-acetoxy-6-(2-chloro-4-trifluoromethyl-phenoxy)-2,3-dimethyl-7-trifluoromethyl-quinoline (Compound No. 228)

A solution of 3.43 g of 4-(2-chloro-4-trifluoromethyl-phenoxy)-3-trifluoromethyl-aniline, 3.1 g of ethyl 2-methylacetoacetate, and 1.83 g of p-toluenesulfonic acid dissolved in 100 mL of xylene was heated under reflux for 19 hr. The reaction solution was cooled, and the precipitated crystals were collected by filtration to give 4.79 g of a mixture of 6-(2-chloro-4-trifluoromethyl-phenoxy)-2,3-dimethyl-4-hydroxy-5-trifluoromethyl-quinoline with 6-(2-chloro-4-trifluoromethyl-phenoxy)-2,3-dimethyl-4-hydroxy-7-trifluoromethyl-quinoline. Next, 20 mL of acetic anhydride was added to 2.4 g of the crystals, and the mixture was heated at 120 to 125° C. for one hr. This reaction solution was concentrated under the reduced pressure. Ethyl acetate was then added to the concentrate, and the mixture was washed with brine. Thereafter, the solvent was removed under the reduced pressure, and the crude product was purified by column chromatography on silica gel (BW300, manufactured by Fuji Sylysia Chemical Ltd., solvent: n-hexane/ethyl acetate) to give 0.45 g of 4-acetoxy-6-(2-chloro-4-trifluoromethyl-phenoxy)-2,3-dimethyl-5-trifluoromethyl-quinoline (yield 19.5%) and 1.02 g of 4-acetoxy-6-(2-chloro-4-trifluoromethyl-phenoxy)-2,3-dimethyl-7-trifluoromethyl-quinoline (yield 44.3%).

Synthesis Example 5

4-Methoxycarbonyloxy-2-ethyl-3-methyl-6-(4-trifluoromethoxyphenoxy)-5-trifluoromethyl-quinoline (Compound No. 112) and 4-methoxycarbonyloxy-2-ethyl-3-methyl-6-(4-trifluoromethoxyphenoxy)-7-trifluoromethyl-quinoline (Compound No. 123)

A solution of 3.4 g of 4-(4-trifluoromethoxyphenoxy)-3-trifluoromethyl-aniline, 3.5 g of ethyl 2-methyl-3-oxopentanoate, and 2.1 g of p-toluenesulfonic acid dissolved in 100 mL of xylene was heated under reflux for 10 hr. The reaction solution was cooled, and the precipitated crystals were then collected by filtration to give 6.0 g of a mixture of 2-ethyl-3-methyl-4-hydroxy-6-(4-trifluoromethoxyphenoxy)-5-trifluoromethyl-quinoline with 2-ethyl-3-methyl-4-hydroxy-6-(4-trifluoromethoxyphenoxy)-7-trifluoromethyl-quinoline. Next, 50 mL of dimethylacetamide was added to 6.0 g of the crystals, and 1.7 g of 60% sodium hydride and 4.6 g of methyl chloroformate were added thereto at 0° C. The mixture was stirred at 4 to 24° C. for 1.5 hr, and 100 mL of toluene and 100 mL of distilled water were then added to the reaction solution. The organic layer was washed with water and was then concentrated under the reduced pressure. The crude product was purified by column chromatography on silica gel (BW300, manufactured by Fuji Sylysia Chemical Ltd., solvent: n-hexane /ethyl acetate) to give 0.63 g of 4-methoxycarbonyloxy-2-ethyl-3-methyl-6-(4-trifluoromethoxyphenoxy)-5-trifluoromethyl-quinoline (yield 12.9%) and 2.00 g of 4-methoxycarbonyl-2-ethyl-3-methyl-6-(4-trifluoromethoxyphenoxy)-7-trifluoromethyl-quinoline (yield 40.9%).

Synthesis Example 6

4-Acetoxy-6-(2-chloro-4-trifluoromethoxyphenoxy)-2,3-dimethyl-5-trifluoromethyl-quinoline (Compound No. 253) and 4-acetoxy-6-(2-chloro-4-trifluoromethoxyphenoxy)-2,3-dimethyl-7-trifluoromethyl-quinoline (Compound No. 259)

A solution of 3.43 9 of 4-(2-chloro-4-trifluoromethoxyphenoxy)-3-trifluoromethyl-aniline, 4.1 g of ethyl 2-methylacetoacetate, and 2.5 g of p-toluenesulfonic acid dissolved in 130 mL of xylene was heated under reflux for 17 hr. This reaction solution was cooled, and the precipitated crystals were then collected by filtration to give 6.18 g of a mixture of 6-(2-chloro-4-trifluoromethoxyphenoxy)-2,3-dimethyl-4-hydroxy-5-trifluoromethyl-quinoline with 6-(2-chloro-4-trifluoromethoxyphenoxy)-2,3-dimethyl-4-hydroxy-7-trifluoromethyl-quinoline. Next, 30 mL of acetic anhydride was added to 2.4 g of the crystals, and the mixture was heated at 120 to 125° C. for 1.5 hr. This reaction solution was concentrated under the reduced pressure, ethyl acetate was then added to the concentrate, and the mixture was washed with brine. Thereafter, the solvent was removed under the reduced pressure, and the crude product was purified by column chromatography on silica gel (BW300, manufactured by Fuji Sylysia Chemical Ltd., solvent: n-hexane/ethyl acetate) to give 0.33 g of 4-acetoxy-6-(2-chloro-4-trifluoromethoxyphenoxy)-2,3-dimethyl-5-trifluoromethyl-quinoline (yield 10.4%) and 1.11 g of 4-acetoxy-6-(2-chloro-4-trifluoromethoxyphenoxy)-2,3-dimethyl-7-trifluoromethyl-quinoline (yield 35.1%).

Synthesis Example 7

4-Acetoxy-5-chloro-6-(4-methoxyphenoxy)-2,3-dimethyl-quinoline (Compound No. 50) and 4-acetoxy-7-chloro-6-(4-methoxyphenoxy)-2,3-dimethyl-quinoline (Compound No. 51)

A mixture composed of 2.9 g of 3-chloro-4-(4-methoxyphenoxy)-aniline, 2.9 g of ethyl 2-methylacetoacetate, and 0.5 mL of ethanol was added dropwise to 4.2 g of polyphosphoric acid heated to 150° C. This reaction solution was stirred at 140 to 150° C. while removing ethanol by evaporation for 3 hr and was then poured into 195 mL of iced water containing 2 mL of concentrated hydrochloric acid. The crystals were collected by filtration and were washed with n-hexane to give 3.29 g of a mixture of 5-chloro-6-(4-methoxyphenoxy)-4-hydroxy-2,3-dimethyl-quinoline with 7-chloro-6-(4-methoxyphenoxy)-4-hydroxy-2,3-dimethyl-quinoline (yield 100%).

The crystals of the mixture thus obtained stirred in 50 mL of acetic anhydride with heating at 120 to 125° C. for one hr. The reaction solution was concentrated, ethyl acetate and toluene was then added to the concentrate, and the mixture was washed with a saturated aqueous sodium hydrogencarbonate solution and saturated brine. The solvent was then removed under the reduced pressure. The crude product was purified by column chromatography on silica gel (BW300, manufactured by Fuji Sylysia Chemical Ltd., solvent: n-hexane/ethyl acetate) to give 1.4 g of 4-acetoxy-5-chloro-6-(4-methoxyphenoxy)-2,3-dimethyl-quinoline (yield 37.7%) and 1.07 g of 4-acetoxy-7-chloro-6-(4-methoxyphenoxy)-2,3-dimethyl-quinoline (yield 28.8%).

Synthesis Example 8

4-Acetoxy-6-(4-trifluoromethoxyphenoxy)-2,3,5-trimethyl-quinoline (Compound No. 86) and 4-acetoxy-6-(4-trifluoromethoxyphenoxy)-2,3,7-trimethyl-quinoline (Compound No. 118)

A solution of 2.2 g of 4-(4-trifluoromethoxyphenoxy)-3-methyl-aniline, 2.6 g of ethyl 2-methylacetoacetate, and 1.52 g of p-toluenesulfonic acid dissolved in 81 mL of xylene was heated under reflux for 12 hr. This reaction solution was cooled, and the precipitated crystals were then collected by filtration and were washed with distilled water and n-hexane to give 3.88 g of a mixture of 6-(4-trifluoromethoxyphenoxy)-4-hydroxy-2,3,5-trimethyl-quinoline with 6-(4-trifluoromethoxyphenoxy)-4-hydroxy-2,3,7-trimethyl-quinoline (yield 100%). The crystals of the mixture (2.9 g) thus obtained were stirred in 30 mL of acetic anhydride with heating at 120 to 125° C. for 2 hr. The reaction solution was concentrated, ethyl acetate was then added to the concentrate, and the mixture was washed with saturated brine. The solvent was then removed under the reduced pressure, and the crude product was purified by column chromatography on silica gel (BW300, manufactured by Fuji Sylysia Chemical Ltd., solvent: n-hexane/ethyl acetate) to give 0.4 g of 4-acetoxy-6-(4-trifluoromethoxyphenoxy)-2,3,5-trimethyl-quinoline (yield 12.4%) and 0.19 g of 4-acetoxy-6-(4-trifluoromethoxyphenoxy)-2,3,7-trimethyl-quinoline (yield 6%).

Synthesis Example 9

4-Acetoxy-6-(4-trifluoromethoxyphenoxy)-2,3,5,7-tetramethyl-quinoline (Compound No. 132)

A solution of 1.78 g of 4-(4-trifluoromethoxyphenoxy)-3,5-dimethylaniline, 1.92 g of ethyl 2-methylacetoacetate, and 1.14 g of p-toluenesulfonic acid dissolved in 61 mL of xylene was heated under reflux for 9 hr. This reaction solution was cooled, and the precipitated crystals were then collected by filtration and were washed with distilled water and n-hexane to give 2.94 g of 6-(4-trifluoromethoxyphenoxy)-4-hydroxy-2,3,5,7-tetramethyl-quinoline 2.26 g (yield 100%). A 1.14 g portion in the crystals thus obtained was stirred in 15 mL of acetic anhydride with heating at 120 to 125° C. for 2 hr. The reaction solution was concentrated, ethyl acetate was then added to the concentrate, the mixture was washed with saturated brine, and the solvent was then concentrated under the reduced pressure. The crude product was purified by column chromatography on silica gel (BW300, manufactured by Fuji Sylysia Chemical Ltd., solvent: n-hexane/ethyl acetate) to give 0.74 g of 4-acetoxy-6-(4-trifluoromethoxyphenoxy)-2,3,5,7-tetramethyl-quinoline (yield 58.4%).

Synthesis Example 10

4-Acetoxy-5-chloro-6-(4-chlorophenylthio)-2,3-dimethyl-guinoline (Compound No. 371) and 4-acetoxy-7-chloro-6-(4-chlorophenylthio)-2,3-dimethyl-quinoline (Compound No. 372)

A mixture composed of 2.7 g of 3-chloro-4-(4-chlorophenylthio)-aniline, 3.2 g of ethyl 2-methylacetoacetate, and 0.5 mL of ethanol was added dropwise to 4.2 g of polyphosphoric acid heated to 150° C. This reaction solution was stirred at 130 to 140° C. while removing ethanol by evaporation for one hr. The reaction solution was then poured into 195 mL of iced water containing 2 mL of concentrated hydrochloric acid. As a result, crystals were produced. The crystals were collected by filtration and were washed with n-hexane to give 3.61 g of a mixture of 5-chloro-6-(4-chlorophenylthio)-4-hydroxy-2,3-dimethyl-quinoline with 7-chloro-6-(4-chlorophenylthio)-4-hydroxy-2,3-dimethyl-quinoline. The crystal of the mixture (3.5 g) thus obtained were stirred in 50 mL of acetic anhydride with heating at 120 to 125° C. for one hr. The reaction solution was concentrated, and the crude product was then purified by column chromatography on silica gel (BW300, manufactured by Fuji Sylysia Chemical Ltd., solvent: n-hexane/ethyl acetate) to give 0.95 g of 4-acetoxy-5-chloro-6-(4-chlorophenylthio)-2,3-dimethyl-quinoline (yield 24.2%) and 0.15 g of 4-acetoxy-7-chloro-6-(4-chlorophenylthio)-2,3-dimethyl-quinoline (yield 4%).

Synthesis Example 11

4-Acetoxy-5-chloro-6-(4-chlorobenzoyl)-2,3-dimethyl-quinoline (Compound No. 369) and 4-acetoxy-7-chloro-6-(4-chlorobenzoyl)-2,3-dimethyl-quinoline (Compound No. 370)

A solution of 2.7 g of 3-chloro-4-(4-chlorobenzoyl)aniline, 2.4 g of ethyl 2-methylacetoacetate, and 0.3 g of p-toluenesulfonic acid dissolved in 100 mL of xylene was heated under reflux for 31 hr. This reaction solution was cooled, and the precipitated crystals were collected by filtration and were washed with n-hexane to give 2.68 g of a mixture of 5-chloro-6-(4-chlorobenzoyl)-4-hydroxy-2,3-dimethyl-quinoline with 7-chloro-6-(4-chlorobenzoyl)-4-hydroxy-2,3-dimethyl-quinoline (yield 77%). The crystals of the mixture thus obtained were stirred in 40 mL of acetic anhydride with heating at 120 to 125° C. for one hr. The reaction solution was concentrated, and the crude product was then purified by column chromatography on silica gel (BW300, manufactured by Fuji Sylysia Chemical Ltd., solvent: n-hexane/ethyl acetate) to give 1.0 g of 4-acetoxy-5-chloro-6-(4-chlorobenzoyl)-2,3-dimethyl-quinoline (yield 32.6%) and 0.47 g of 4-acetoxy-7-chloro-6-(4-chlorobenzoyl)-2,3-dimethyl-quinoline (yield 15.6%).

Synthesis Example 12

4-Acetoxy-5-chloro-6-(4-chlorobenzyl)-2,3-dimethylquinoline (Compound No. 377) and 4-acetoxy-7-chloro-6-(4-chlorobenzyl)-2,3-dimethyl-quinoline (Compound No. 378)

A solution of 3.0 g of 3-chloro-4-(4-chlorobenzyl)aniline, 2.9 g of ethyl 2-methylacetoacetate, and 0.4 g of p-toluenesulfonic acid dissolved in 100 mL of xylene was heated under reflux for 15 hr. This reaction solution was cooled, and the precipitated crystals were collected by filtration and were washed with n-hexane to give 4.06 g of a mixture of 5-chloro-6-(4-chlorobenzyl)-4-hydroxy-2,3-dimethylquinoline with 7-chloro-6-(4-chlorobenzyl)-4-hydroxy-2,3-dimethylquinoline. The crystals of the mixture (3.9 g) thus obtained were stirred in 40 mL of acetic anhydride with heating at 120 to 125° C. for one hr. The reaction solution was concentrated, ethyl acetate was then added to the concentrate, and the mixture was washed with saturated brine. The solvent was then removed under the reduced pressure. The crude product was purified by column chromatography on silica gel (BW300, manufactured by Fuji Sylysia Chemical Ltd., solvent: n-hexane/ethyl acetate) to give 1.28 g of 4-acetoxy-5-chloro-6-(4-chlorobenzyl)-2,3-dimethyl-quinoline (yield 28.5%) and 0.56 g of 4-acetoxy-7-chloro-6-(4-chlorobenzyl)-2,3-dimethylquinoline (yield 12.5%).

Synthesis Example 13

4-Cyclopropanecarbonyloxy-2,3-dimethyl-6-(4-trifluoromethoxyphenoxy)-5-trifluoromethyl-quinoline (Compound No. 96)

5-Trifluoromethyl-6-(4-trifluoromethoxyphenoxy)-4-hydroxy-2,3-dimethyl-quinoline (30 mg) prepared in Synthesis Example 3 was dissolved in 1 mL of dimethylformamide. Under ice cooling, 4.3 mg of 60% sodium hydride was added to the solution, and the mixture was stirred for one hr. Thereafter, 10.4 mg of cyclopropanecarbonyl chloride was added thereto, and the mixture was stirred at room temperature for 3 hr. The reaction mixture was added to 5 mL of water, and the mixture was extracted with 5 mL of ethyl acetate. The ethyl acetate layer was washed with a saturated sodium hydrogencarbonate solution and saturated brine, was dried over anhydrous sodium sulfate, and was then concentrated under the reduced pressure. The crude product thus obtained was purified by chromatography on silica gel (Mega Bond Elut SI (Varian) 10 mL, solvent: n-hexane/ethyl acetate) to give 4-Cyclopropanecarbonyloxy-2,3-dimethyl-6-(4-trifluoromethoxyphenoxy)-5-trifluoromethyl-quinoline (13.8 mg, yield 39.5%).

Synthesis Example 14

4-Acetoxy-2,3-dimethyl-6-(4-trifluoromethoxyphenyl)-5-trifluoromethyl-quinoline (Compound No. 454) and 4-acetoxy-2,3-dimethyl-6-(4-trifluoromethoxyphenyl)-7-trifluoromethylquinoline (Compound No. 436)

A solution of 2.97 g of 4-amino-4'-trifluoromethoxy-2-trifluoromethylbiphenyl, 2.97 g of ethyl 2-methylacetoacetate, and 1.76 g of p-toluenesulfonic acid dissolved in 94 mL of xylene was heated under reflux for 11 hr. This reaction solution was cooled, and the precipitated crystals were then collected by filtration and were washed with n-hexane to give 4.05 g of a mixture of 5-trifluoromethyl-6-(4-trifluoromethoxyphenyl)-4-hydroxy-2,3-dimethylquinoline with 7-trifluoromethyl-6-(4-trifluoromethoxyphenyl)-4-hydroxy-2,3-dimethylquinoline. The crystals of the mixture (3.71 g) thus obtained were stirred in 35 mL of acetic anhydride with heating at 120 to 125° C. for 2 hr. The reaction solution was concentrated, ethyl acetate was then added to the concentrate, and the mixture was washed with saturated brine. The solvent was concentrated under the reduced pressure. The crude product was purified by column chromatography on silica gel (BW300, manufactured by Fuji Sylysia Chemical Ltd., solvent: n-hexane/ethyl acetate) to give 0.5 g of 4-acetoxy-2,3-dimethyl-6-(4-trifluoromethoxyphenyl)-5-trifluoromethylquinoline (yield 12.2%) and 1.07 g of 4-acetoxy-2,3-dimethyl-6-(4-trifluoromethoxyphenyl)-7-trifluoromethylquinoline (yield 26.1%).

Synthesis Example 15

4-Methoxycarbonyloxy-6-(3-chloro-5-trifluoromethylpyridin-2-yloxy)-2-ethyl-3,5,7-trimethylquinoline (Compound No. 685)

A solution of 1.52 9 of 4-(3-chloro-5-trifluoromethylpyridin-2-yloxy)-3,5-dimethylaniline, 1.75 g of methyl 2-methyl-3-oxopentanoate, and 0.92 g of p-toluenesulfonic acid dissolved in 49 mL of xylene was heated under reflux for 8 hr. This reaction solution was cooled, and the precipitated crystals were then collected by filtration and were washed with n-hexane and distilled water and were dried to give 2.56 g of 6-(3-chloro-5-trifluoromethylpyridin-2-yloxy)-2-ethyl-4-hydroxy-3,5,7-trimethyl-quinoline. Dimethylacetamide (30 mL) was then added to 1.97 g of the crystals thus obtained, and 0.38 g of 60% sodium hydride and 0.9 g of methyl chloroformate were added thereto at room temperature. The mixture was stirred at room temperature for 2 hr, and ethyl acetate and distilled water were then added. The organic layer was washed with brine and was then concentrated under the reduced pressure. The crude product was purified by column chromatography on silica gel (BW300, manufactured by Fuji Sylysia Chemical Ltd., solvent: n-hexane /ethyl acetate) to give 1.25 g of 4-methoxycarbonyloxy-6-(3-chloro-5-trifluoromethylpyridin-2-yloxy)-2-ethyl-3,5,7-trimethylquinoline (yield 55.6%).

Synthesis Example 16

4-Acetoxy-5-chloro-6-(5-chloropyridin-2-yloxy)-2,3-dimethylquinoline (Compound No. 679) and 4-acetoxy-7-chloro-6-(5-chloropyridin-2-yloxy)-2,3-dimethylquinoline (Compound No. 680)

A solution of 3.16 g of 3-chloro-4-(5-chloropyridin-2-yloxy)aniline, 2.98 g of ethyl 2-methylacetoacetate, and 0.4 g of p-toluenesulfonic acid dissolved in 100 mL of xylene was heated under reflux for 16 hr. This reaction solution was cooled, and the precipitated crystals were then collected by filtration and was washed with n-hexane to give 3.09 g of a mixture of 5-chloro-6-(5-chloropyridin-2-yloxy)-4-hydroxy-2,3-dimethylquinoline with 7-chloro-6-(5-chloropyridin-2-yloxy)-4-hydroxy-2,3-dimethyl-quinoline. The crystals of the mixture thus obtained were stirred in 40 mL of acetic anhydride with heating at 120 to 125° C. for one hr. The reaction solution was concentrated. The crude product was purified by column chromatography on silica gel (BW300, manufactured by Fuji Sylysia Chemical Ltd., solvent: n-hexane/ethyl acetate) and was further recrystallized from n-hexane/ethyl acetate to give 0.53 g of 4-acetoxy-5-chloro-6-(5-chloropyridin-2-yloxy)-2,3-dimethylquinoline (yield 15.2%) and 0.12 g of 4-acetoxy-7-chloro-6-(5-chloropyridin-2-yloxy)-2,3-dimethylquinoline (yield 3.5%).

Synthesis Example 17

4-Methoxycarbonyloxy-2-ethyl-3,5,7-trimethyl-6-(3-(4-trifluoromethyl-phenoxy)propoxy)quinoline (Compound No. 397)

A solution of 1.18 g of 3,5-dimethyl-4-(3-(4-trifluoromethylphenoxy)propoxy)aniline, 1.35 g of methyl 2-methyl-3-oxopentanoate, and 0.7 g of p-toluenesulfonic acid dissolved in 38 mL of xylene was heated under reflux for 7 hr. This reaction solution was cooled, and ethyl acetate and sodium bicarbonate water were added thereto, followed by separation. The ethyl acetate layer was washed with brine and was further concentrated under the reduced pressure to give 1.38 g of 2-ethyl-4-hydroxy-3,5,7-trimethyl-6-(3-(4-trifluoromethylphenoxy)propoxy)quinoline. Next, 1.38 g of the product thus obtained was added to 15 mL of dimethylacetamide, and 0.26 g of 60% sodium hydride and 0.6 g of methyl chloroformate were added thereto at room temperature. The reaction solution was stirred at room temperature for 2 hr, and ethyl acetate and distilled water were then added thereto. The organic layer was washed with brine and was concentrated under the reduced pressure. The crude product was purified by column chromatography on silica gel (BW300, manufactured by Fuji Sylysia Chemical Ltd., solvent: n-hexane/ethyl acetate) and was then recrystallized from n-hexane/ethyl acetate to give 1.13 g of 4-methoxycarbonyloxy-2-ethyl-3,5,7-trimethyl-6-(3-(4-trifluoromethylphenoxy)propoxy)quinoline (yield 72.2%).

$^1$H-NMR data of the compounds according to the present invention synthesized in the same manner as described above were as summarized in Tables 15 to 25 below.

TABLE 15

| Compound No. | NMR spectral data | Solvent for measurement | m.p. |
|---|---|---|---|
| 2 | 7.94(1H, d, J=9.0), 7.32(1H, d, J=9.0), 7.27(2H, d, J=9.0), 6.89(2H, d, J=9.0), 2.71(3H, s), 2.46(3H, s), 2.27(3H, s) | CDCl3 | 167~169 |
| 3 | 7.93(1H, d, J=9.5), 7.33(1H, d, J=9.5), 7.27(2H, d, J=8.8), 6.90(2H, d, J=8.8), 3.97(3H, s), 2.72(3H, s), 2.34(3H, s) | CDCl3 | 89~91 |
| 4 | 7.93(1H, d, J=8.1), 7.32(1H, d, J=8.1), 7.29(2H, d, J=8.6), 6.89(2H, d, J=8.6), 2.71(3H, s), 2.27(3H, s), 1.47(9H, s) | CDCl3 | 155~156 |
| 5 | 7.94(1H, d, J=9.0), 7.33(1H, d, J=9.0), 7.29(2H, d, J=7.0), 6.89(2H, d, J=7.0), 2.76(3H, s), 2.69(2H, broad), 2.46(3H, s), 1.21(3H, t, J=7.2) | CDCl3 | 123~124 |
| 6 | 7.93(1H, d, J=9.0), 7.33(1H, d, J=9.0), 7.29(2H, d, J=8.8), 6.88(2H, d, J=8.8), 2.75(3H, s), 2.64(2H, broad), 2.45(3H, s), 1.59-1.40(4H, m), 1.00(3H, t, J=7.4) | CDCl3 | 122~123 |
| 7 | 7.97(1H, d, J=8.3), 7.38(1H, d, J=8.3), 7.29(2H, d, J=7.7), 7.07(1H, s), 6.87(2H, d, J=7.7), 2.73(3H, s), 2.41(3H, s) | CDCl3 | — |
| 8 | 7.97(1H, d, J=9.0), 7.33(1H, d, J=9.0), 7.29(2H, d, J=9.0), 6.88(2H, d, J=9.0), 3.02(2H, q, J=7.2), 2.46(3H, s), 2.30(3H, s), 1.38(3H, t, J=7.2) | CDCl3 | 136~137 |
| 10 | 8.01(1H, d, J=9.5), 7.38(1H, d, 9.5), 7.28(2H, d, J=8.3), 6.88(2H, d, J=8.3), 3.23(1H, m, J=6.5), 2.44(3H, s), 1.40(6H, d, 6.5) | CDCl3 | — |
| 11 | 7.96(1H, d, J=9.6), 7.32(1H, d, J=9.6), 7.28(2H, d, J=8.9), 6.88(2H, d, J=8.9), 2.98(2H, t, J=7.8), 2.46(3H, s), 2.29(3H, s), 1.77(2H, m), 1.50(2H, s), 0.99(3H, t, J=7.1) | CDCl3 | 153~155 |
| 12 | 8.18(1H, d, J=8.9), 7.54(1H, s), 7.50(1H, d, J=8.9), 7.37(2H, d, J=8.6), 6.96(2H, d, J=8.6), 2.48(3H, s) | CDCl3 | — |
| 13 | 8.01(1H, d, J=9.0), 7.35(1H, d, J=9.0), 7.31(2H, d, J=8.8), 6.90(2H, d, J=8.8), 5.39(2H, s), 2.48(3H, s), 2.31(3H, s), 2.18(3H, s) | CDCl3 | 186~187 |
| 14 | 8.12(1H, d, J=9.0), 7.39(2H, d, J=8.8), 7.20(1H, d, J=9.0), 7.07(2H, d, J=8.8), 2.72(3H, s), 2.60(3H, s), 2.30(3H, s) | CDCl3 | 164~166 |
| 15 | 7.81(1H, d, J=8.6), 7.37(1H, d, J=8.6), 7.28(2H, d, J=9.0), 6.92(2H, d, J=9.0), 2.71(3H, s), 2.41(3H, s), 2.29(3H, s) | CDCl3 | 125~127 |
| 16 | 7.87(1H, d, J=9.0), 7.26(1H, d, J=9.0), 7.25(2HJ=9.0), 2.71(3H, s), 2.59(3H, s), 2.44(3H, s), 2.23(3H, s) | CDCl3 | 185~187 |
| 19 | 8.10(1H, d, J=9.3), 7.32(2H, d, J=9.0), 7.24(1H, d, J=9.3), 6.92(2H, d, J=9.0), 2.72(3H, s), 2.42(3H, s), 2.26(3H, s) | CDCl3 | 122~123 |
| 21 | 8.40(1H, s), 7.36(2H, d, J=8.8), 7.01(1H, s), 7.02(2H, d, J=8.8), 2.72(3H, s), 2.33(3H, s), 2.24(3H, s) | CDCl3 | 130~131 |
| 22 | 8.15(1H, s), 7.33(2H, d, J=8.9), 7.19(1H, s), 6.93(2H, d, J=8.9), 2.71(3H, s), 2.38(3H, s), 2.23(3H, s) | CDCl3 | 160~162 |
| 23 | 8.16(1H, s), 7.32(2H, d, J=8.8), 7.27(1H, s), 6.94(2H, d, J=8.8), 3.91(3H, s), 2.71(3H, s), 2.29(3H, s). | CDCl3 | 169~171 |
| 24 | 8.12(1H, s), 7.37(2H, d, J=8.8), 7.04(2H, d, J=8.8), 6.88(1H, s), 2.69(3H, s), 2.18(3H, s), 1.29(9H, s) | CDCl3 | 164~165 |
| 25 | 8.14(1H, s), 7.32(2H, d, J=8.8), 7.11(1H, s), 6.93(2H, d, J=8.8), 2.75(3H, s), 2.69(2H, q, J=7.2), 2.37(3H, s), 1.18(3H, t, J=7.2) | CDCl3 | 120~121 |
| 26 | 8.14(1H, s), 7.32(2H, d, J=7.2), 7.11(1H, s), 6.94(2H, d, J=7.2), 2.74(3H, s), 2.64(2H, t, J=8.4), 2.37(3H, s), 1.60-1.37(4H, m), 0.96(3H, t, J=7.4) | CDCl3 | 114~115 |

TABLE 16

| | | | |
|---|---|---|---|
| 27 | 8.18(1H, s), 7.39(1H, s), 7.33(2H, d, J=8.0), 7.20(1H, s), 6.93(2H, d, J=8.0), 2.73(3H, s), 2.36(3H, s) | CDCl3 | — |
| 28 | 8.19(1H, s), 7.32(2H, d, J=8.8), 7.20(1H, s), 6.92(2H, d, J=8.8), 3.00(2H, q, J=7.2), 2.38(3H, s), 2.26(3H, s), 1.38(3H, t, J=7.2) | CDCl3 | 143~144 |
| 29 | 8.23(1H, s), 7.40(1H, s), 7.32(2H, d, J=9.0), 0.93(2H, d, J=9.0), 3.24(1H, m, J=6.5), 2.38(3H, s), 1.40(6H, d, J=6.5) | CDCl3 | — |
| 30 | 8.18(1H, s), 7.32(2H, d, J=7.0), 7.19(1H, s), 6.93(2H, d, J=7.0), 2.97(2H, t, J=7.8), 2.38(3H, s), 2.25(3H, s), 1.76(2H, m), 1.50(2H, m), 0.99(3H, t, J=7.1) | CDCl3 | 123~125 |
| 31 | 7.77(1H, d, J=11.4), 7.32(2H, d, J=8.8), 7.26(1H, d, J=8.1), 6.96(2H, d, J=8.8), 2.71(3H, s), 2.41(3H, s), 2.23(3H, s) | CDCl3 | 150~152 |
| 32 | 7.89(1H, s), 7.30(2H, d, J=9.0), 7.05(1H, s), 6.90(2H, d, J=9.0), 2.70(3H, s), 2.39(3H, s), 2.37(3H, s), 2.22(3H, s) | CDCl3 | 148~150 |
| 34 | 7.48'(1H, s), 7.28(2H, d, J=8.8), 7.15(1H, s), 6.91(2H, d, J=8.8), 3.93(3H, s), 2.69(3H, s), 2.38(3H, s), 2.21(3H, s) | CDCl3 | 128.5~129.5 |
| 35 | 7.70(1H, s), 7.36(2H, d, J=8.8), 7.32(1H, s), 6.99(2H, d, J=8.8), 2.75(3H, s), 2.42(3H, s), 2.26(3H, s) | CDCl3 | 149~151 |

TABLE 16-continued

| | | | |
|---|---|---|---|
| 38 | 7.98(1H, d, J=9.3), 7.32(1H, d, J=9.3), 7.27(2H, d, 9.0), 6.87(2H, d, J=9.0), 3.42(1H, m), 2.45(3H, s), 2.31(3H, s), 1.35(6H, d, J=6.1) | CDCl3 | 123~124.5 |
| 40 | 7.96(1H, d, J=9.0), 7.36(1H, d, J=9.0), 7.28-6.80(4H, m), 2.72(3H, s), 2.46(3H, s), 2.28(3H, s) | CDCl3 | 107~108 |
| 41 | 8.16(1H, s), 7.26(1H, s), 7.30-6.84(4H, m), 2.72(3H, s), 2.40(3H, s), 2.24(3H, s) | CDCl3 | 125~126 |
| 42 | 7.92(1H, d, J=9.0), 7.49(1H, d, J=9.0), 7.26-6.82(4H, m), 2.71(3H, s), 2.47(3H, s), 2.27(3H, s) | CDCl3 | 100~102 |
| 43 | 8.16(1H, s), 7.53-6.88(4H, m), 7.05(1H, s), 2.70(3H, s), 2.33(3H, s), 2.22(3H, s) | CDCl3 | 159~161 |
| 44 | 8.01(1H, d, J=9.0), 7.62(2H, d, J=8.8), 7.40(1H, d, J=9.0), 6.96(2H, d, J=8.8), 2.74(3H, s), 2.45(3H, s), 2.28(3H, s) | CDCl3 | 194~195 |
| 45 | 8.19(1H, s), 7.63(2H, d, J=8.8), 7.40(1H, s), 6.98(2H, d, J=8.8), 2.73(3H, s), 2.44(3H, s), 2.26(3H, s) | CDCl3 | 189~192 |
| 46 | 7.91(1H, d, J=9.0), 7.50(1H, d, J=9.0), 7.04(2H, m), 6.93(2H, m), 2.71(3H, s), 2.47(3H, s) 2.27(3H, s) | CDCl3 | 128~132 |
| 47 | 8.14(1H, s), 7.26(1H, s), 7.11(4H, m), 2.70(3H, s), 2.34(3H, s), 2.22(3H, s) | CDCl3 | 130~134 |
| 48 | 7.89(1H, d, J=9.3), 7.30(1H, d, J=9.3), 7.15(2H, d, J=8.2), 6.88(2H, d, J=8.2), 2.71(3H, s), 2.47(3H, s), 2.34(3H, s), 2.27(3H, s) | CDCl3 | 118~120 |
| 49 | 8.13(1H, d, J=8.3), 7.17(2H, d), 7.10(1H, s), 6.92(2H, d, J=8.3), 2.69(3H, s), 2.35(3H, s), 2.32(3H, s), 2.21(3H, s) | CDCl3 | 138~140 |
| 50 | 7.87(1H, d, J=9.0), 7.25(1H, d, J=9.0), 6.96(2H, d, J=9.2), 6.89(2H, d, J=9.2), 3.80(3H, s), 2.70(3H, s), 2.48(3H, s), 2.27(3H, s) | CDCl3 | 120~121 |
| 51 | 8.12(1H, s), 7.01(2H, d, J=9.0), 6.97(1H, s), 6.93(2H, d, J=9.0), 3.83(3H, s), 2.69(3H, s), 2.30(3H, s), 2.21(3H, s) | CDCl3 | 150~152 |
| 52 | 7.92(1H, d, J=9.5), 7.35(1H, d, J=9.5), 7.25-6.51(4H, m), 3.77(3H, s), 2.71(3H, s), 2.46(3H, s), 2.27(3H, s) | CDCl3 | 75~78 |
| 53 | 8.14(1H, s), 7.20(1H, s), 7.28-6.55(4H, m), 3.79(3H, s), 2.71(3H, s), 2.36(3H, s), 2.23(3H, s) | CDCl3 | 97~98 |

TABLE 17

| | | | |
|---|---|---|---|
| 54 | 7.84(1H, d, J=9.0), 7.19(1H, d, J=9.0), 7.16-6.87(4H, m), 3.83(3H, s), 2.69(3H, s), 2.48(3H, s), 2.27(3H, s) | CDCl3 | 54~55 |
| 55 | 8.12(1H, s), 7.03(1H, s), 7.22-6.87(4H, m), 3.81(3H, s), 2.68(3H, s), 2.26(3H, s), 2.20(3H, s) | CDCl3 | 179~180 |
| 56 | 7.99(1H, d, J=8.9), 7.58(2H, d, J=8.6), 7.39(1H, d, J=8.9), 6.99(2H, d, J=8.6), 2.73(3H, s), 2.45(3H, s), 2.28(3H, s) | CDCl3 | 167~168 |
| 61 | 8.16(1H, d, J=9.2), 7.62(2H, d, J=8.7), 7.28(1H, d, J=9.2), 7.04(2H, d, J=8.7), 2.74(3H, s), 2.42(3H, s), 2.27(3H, s) | CDCl3 | 105~107 |
| 64 | 8.18(1H, s), 7.60(2H, d, J=8.6), 7.33(1H, s), 7.01(2H, d, J=8.6), 2.73(3H, s), 2.41(3H, s), 2.25(3H, s) | CDCl3 | 172~172.5 |
| 68 | 8.44(1H, s), 7.65(2H, d, J=8.6), 7.18(1H, s), 7.13(2H, d, J=8.6), 2.75(3H, s), 2.36(3H, s), 2.27(3H, s) | CDCl3 | 138~139.5 |
| 76 | 8.14(1H, d, J=9.0), 7.50-7.26(4H, m), 7.12(1H, d, J=9.0), 2.73(3H, s), 2.42(3H, s), 2.27(3H, s) | CDCl3 | 91~93 |
| 80 | 8.43(1H, s), 7.56-7.25(4H, m), 7.10(1H, s), 2.73(3H, s), 2.32(3H, s), 2.26(3H, s) | CDCl3 | 72~74 |
| 83 | 7.95(1H, d, J=8.9), 7.35(1H, d, J=8.9), 7.19(2H, d, J=9.2), 6.95(2H, d, J=9.2), 2.72(3H, s), 2.46(3H, s), 2.28(3H, s) | CDCl3 | 145~146 |
| 86 | 7.88(1H, d, J=9.1), 7.28(1H, d, J=9.1), 7.15(2H, d, J=8.8), 6.86(2H, d, J=8.8), 2.71(3H, s), 2.60(3H, s), 2.45(3H, s), 2.24(3H, s) | CDCl3 | 160~162 |
| 86 | 7.76(1H, d, J=9.3), 7.36(3H, m), 7.00(2H, d, J=9.3), 2.35(3H, s), 1.94(3H, s) | DMSO-d6 | — |
| 87 | 7.91(1H, d, J=9.1), 7.28(1H, d, J=9.1), 7.15(2H, d, J=8.8), 6.87(2H, d, J=8.8), 3.97(3H, s), 3.02(2H, q, J=7.4), 2.59(3H, s), 2.33(3H, s), 1.38(3H, t, J=7.4) | CDCl3 | 106~107 |
| 90 | 8.10(1H, d, J=8.9), 7.28-7.20(4H, m), 6.99(1H, d, J=8.9), 2.73(3H, s), 2.42(3H, s), 2.26(3H, s) | CDCl3 | 100~101.5 |
| 91 | 8.13(1H, br, d), 7.27-7.21(3H, m), 6.99(2H, d, J=9), 2.76(2H, q, J=7.4), 2.73(3H, s), 2.25(3H, s), 1.30(3H, t, J=7.6) | CDCl3 | — |
| 92 | 8.12(1H, br, d), 7.30-7.21(3H, m), 6.99(2H, d, J=9.0), 2.73(5H, m), 2.25(3H, s), 1.76(2H, m), 1.47(2H, m), 0.99(3H, t, J=7.3) | CDCl3 | — |
| 93 | 8.14(1H, br, d), 7.27-7.22(3H, m), 6.92(2H, d, J=9.3), 2.73-2.69(5H, m), 2.35(2H, m), 2.25(3H, s), 1.78(2H, m), 1.63(2H, m), 1.43-1.29(6H, m) 0.81(3H, t, J=9.2) | CDCl3 | — |
| 95 | 8.11(1H, br, d), 7.26-7.21(3H, m), 6.99(2H, d, J=9.3), 2.73(3H, s), 2.55(2H, d, J=7.1), 2.26(3H, s), 1.07(6H, d, J=6.6), 0.91(1H, m) | CDCl3 | — |
| 96 | 8.10(1H, br, d), 7.26-7.22(3H, m), 6.99(2H, d, J=9.0), 2.72(3H, s), 2.26(3H, s), 2.05(1H, m), 1.19(2H, m), 1.11(2H, m) | CDCl3 | — |
| 97 | 8.10(1H, br, d), 7.26-7.20(3H, m), 6.99(2H, d, J=9.0), 3.57(1H, m), 2.75(3H, s), 2.52-2.38(4H, m), 2.25(3H, s), 2.12(2H, m), | CDCl3 | — |
| 98 | 8.14(1H, br, d), 7.28-7.20(3H, m), 6.99(2H, d, J=9.3), 6.71(1H, dd, J1=17.3, J2=1.2), 6.43(1H, dd, J1=17.3, J2=10.5), 6.13(1H, dd, J1=10.2, J2=1.0), 2.74(3H, s), 2.25(3H, s). | CDCl3 | — |
| 99 | 8.13(1H, br, d), 7.27-7.20(3H, m), 7.00(2H, d, J=9.3), 6.48(1H, s), 5.87(1H, s), 2.72(3H, s), 2.24(3H, s), 2.11(3H, s) | CDCl3 | — |
| 101 | 8.16(1H, br, d), 7.30-7.21(3H, m), 7.00(2H, d, J=9.3), 3.96(3H, s), 2.75(3H, s), 2.34(3H, s), | CDCl3 | — |

TABLE 17-continued

| | | | |
|---|---|---|---|
| 102 | 8.15(1H, br, d), 7.30-7.21(3H, m), 7.00(2H, d, J=9.0), 4.36(2H, q, J=7.0), 2.74(3H, s), 2.34(3H, s), 1.41(3H, t, J=7.2) | CDCl3 | — |

TABLE 18

| | | | |
|---|---|---|---|
| 103 | 8.16(1H, br, d), 7.30-7.21(3H, m), 7.00(2H, d, J=9.3), 4.30(2H, t, J=6.6), 2.75(3H, s), 2.34(3H, s), 1.76(2H, m), 1.50(2H, m), 0.98(3H, t, J=7.4) | CDCl3 | — |
| 104 | 8.16(1H, br, d), 7.30-7.21(3H, m), 7.00(2H, d, J=9.3), 4.30(2H, t, J=6.7), 2.74(3H, s), 2.34(3H, s), 1.76(2H, m), 1.50-1.0(10H, m), 0.88(3H, t, J=7.1) | CDCl3 | — |
| 105 | 8.19(1H, br, d), 7.43(2H, t, J=8.0), 7.32-7.22(6H, m), 7.00(2H, d, J=9.0), 2.77(3H, s), 2.44(3H, s). | CDCl3 | — |
| 106 | 8.16(1H, br, d), 7.30-7.21(3H, m), 6.99(2H, d, J=8.8), 4.07(2H, d, J=6.6), 2.75(3H, s), 2.34(3H, s), 2.08(1H, m), 1.01(6H, d, J=6.6) | CDCl3 | — |
| 107 | 8.14(1H, bd, d), 7.30-7.21(3H, m), 6.99(2H, d, J=9.0), 6.01(1H, m), 5.46(1H, dd, J1=17.3, J2=1.5), 5.36(1H, dd, J1=10.5, J2=1.2), 4.78(2H, dt, J1=5.8, J2=1.2), 2.74(3H, s), 2.34(3H, s). | CDCl3 | — |
| 108 | 8.20(1H, br, d), 7.32-7.22(3H, m), 7.00(2H, d, J=9.0), 4.91(2H, s), 2.76(3H, s), 2.37(3H, s). | CDCl3 | — |
| 110 | 8.17(1H, br, d), 7.30-7.21(3H, m), 6.99(2H, d, J=9.3), 2.75(3H, s), 2.47(3H, s), 2.32(3H, s). | CDCl3 | — |
| 111 | 7.79(1H, d, J=9.3), 7.38-7.35(3H, m), 7.01(2H, d, J=9), 2.67(2H, q, J=7.5), 1.97(3H, s), 1.22(3H, t, J=7.5) | DMSO-d6 | — |
| 112 | 8.16(1H, d, J=9.1), 7.28(1H, d, J=9.1), 7.21(2H, d, J=9.0), 6.99(2H, d, J=9.0), 3.94(3H, s), 3.03(2H, q, J=7.2), 2.35(3H, s), 1.39(3H, t, J=7.2) | CDCl3 | oil |
| 114 | 8.16(1H, d, J=9.3), 7.30-6.97(5H, m), 3.23(2H, t, J=7.7), 2.97(2H, t, J=7.4), 2.39(3H, s), 2.30-2.20(2H, m) | CDCl3 | 108.5~110 |
| 115 | 8.11(1H, d, J=9.3), 7.28-6.96(5H, m), 3.12(2H, broad), 2.62(2H, broad), 2.41(3H, s), 2.00(2H, broad), 1.90(2H, broad) | CDCl3 | 105~107 |
| 116 | 8.16(1H, s), 7.23(2H, d, J=8.8), 7.14(1H, s), 7.01(2H, d, J=8.8), 2.71(3H, s), 2.35(3H, s), 2.23(3H, s) | CDCl3 | 145~147 |
| 118 | 7.90(1H, s), 7.21(2H, d, J=8.8), 7.01(1H, s), 6.98(2H, d, J=8.8), 2.70(3H, s), 2.40(3H, s), 2.34(3H, s), 2.22(3H, s) | CDCl3 | 141~143 |
| 120 | 7.94(1H, s), 7.20(2H, d, J=8.8), 7.14(1H, s), 6.97(2H, d, J=8.8), 3.88(3H, s), 3.01(2H, q, J=7.6), 2.41(3H, s), 2.31(3H, s), 1.38(3H, t, J=7.6) | CDCl3 | 118.5~120 |
| 121 | 7.94(1H, s), 7.20(2GH, d, J=8.8), 6.99(1H, s), 6.97(2H, d, J=8.8), 3.00(2H, q, J=7.5), 2.40(3H, s), 2.35(3H, s), 2.25(3H, s), 1.37(3H, t, J=7.5) | CDCl3 | — |
| 122 | 8.41(1H, s), 7.28(2H, d, J=8.9), 7.12(2H, d, J=8.9), 6.98(1H, s), 2.73(3H, s), 2.30(3H, s), 2.25(3H, s) | CDCl3 | 109~110.5 |
| 123 | 8.45(1H, s), 7.26(2H, d, J=8.7), 7.13(1H, s), 7.11(2H, d, J=8.7), 3.86(3H, s), 3.02(2H, q, J=7.7), 2.33(3H, s), 1.40(3H, t, J=7.7) | CDCl3 | 117~118.5 |
| 124 | 8.60(1H, s), 7.31(2H, d, J=8.9), 7.19(2H, d, J=8.9), 6.92(1H, s), 2.41(3H, s), 2.30(6H, s) | CDCl3 | 163~164.5 |
| 125 | 8.42(1H, s), 7.28-7.09(5H, m), 3.22(2H, t, J=7.8), 2.95(2H, t, J=7.5), 2.30(3H, s), 2.26-2.19(2H, m) | CDCl3 | 135~137 |
| 126 | 8.40(1H, s), 7.27(2H, d, J=7.0), 7.12(2H, d, J=7.0), 6.99(1H, s), 3.14(2H, t, J=6.4), 2.74(2H, t, J=6.3), 2.29(3H, s), 2.05-1.83(4H, m) | CDCl3 | 155~157 |
| 127 | 8.15(1H, s), 7.15(2H, d, J=9.0), 6.83(2H, d, J=9.0), 2.74(3H, s), 2.43(3H, s), 2.26(3H, s) | CDCl3 | 160~162 |
| 132 | 7.79(1H, s), 7.11(2H, d, J=9.0), 6.74(2H, d, J=9.0), 2.70(3H, s), 2.51(3H, s), 2.41(3H, s), 2.26(3H, s), 2.22(3H, s) | CDCl3 | 159~161 |
| 133 | 7.79(1H, s), 7.11(2H, d, J=9.0), 6.74(2H, d, J=9.0), 3.94(3H, s), 2.71(3H, s), 2.50(3H, s), 2.28(3H, s), 2.26(3H, s) | CDCl3 | 146~148 |

TABLE 19

| | | | |
|---|---|---|---|
| 135 | 7.83(1H, s), 7.11(2H, d, J=8.8), 6.75(2H, d, J=8.8), 3.94(3H, s), 3.01(2H, q, J=7.6), 2.50(3H, s), 2.30(3H, s), 2.26(3H, s), 1.38(3H, t, J=7.6) | CDCl3 | 140~142 |
| 136 | 8.35(1H, s), 7.15(2H, d, J=8.7), 6.81(2H, d, J=8.7), 2.74(3H, s), 2.40(3H, s), 2.26(3H, s) | CDCl3 | 110~113 |
| 137 | 7.20(2H, d, J=9.0), 7.10(1H, s), 6.96(2H, d, J=9.0), 2.72(6H, s), 2.40(3H, s), 2.25(3H, s) | CDCl3 | 110~111.5 |
| 138 | 8.40(1H, s), 7.14(2H, d, J=8.8), 6.80(2H, d, J=8.8), 2.76(3H, s), 2.42(3H, s), 2.30(3H, s) | CDCl3 | 135~137 |
| 141 | 7.89(1H, d, J=9.1), 7.31-6.74(5H, m), 2.70(3H, s), 2.59(3H, s), 2.44(3H, s), 2.24(3H, s) | CDCl3 | 86~87 |
| 143 | 8.14(1H, d, J=9.3), 7.36-6.86(5H, m), 2.73(3H, s), 2.42(3, s), 2.27(3H, s) | CDCl3 | 64~66 |
| 145 | 7.92(1H, s), 7.36-6.74(5H, m), 2.69(3H, s), 2.39(3H, s), 2.37(3H, s), 2.22(3H, s) | CDCl3 | — |
| 147 | 8.42(1H, s), 7.42-6.70(5H, m), 2.73(3H, s), 2.33(3H, s), 2.26(3H, s) | CDCl3 | 89~91 |
| 151 | 7.98(1H, d, J=9.1), 7.60(2H, d, J=8.7), 7.39(1H, d, J=9.1), 6.94(2H, d, J=8.7), 2.73(3H, s), 2.45(3H, s), 2.28(3H, s) | CDCl3 | 147~151 |
| 156 | 8.16(1H, d, J=9.2), 7.64(2H, d, J=8.5), 7.30(1H, d, J=9.2), 6.99(2H, d, J=8.5), 2.74(3H, s), 2.42(3H, s), 2.27(3H, s) | CDCl3 | 87~89 |

TABLE 19-continued

| | | | |
|---|---|---|---|
| 159 | 8.17(1H, s), 7.64(2, d, J=8.6), 7.28(1H, s), 6.99(2H, d, J=8.6), 2.72(3H, s), 2.39(3H, s), 2.24(3H, s) | CDCl3 | 109~110 |
| 163 | 7.69(1H, s), 7.69(2H, d, J=8.7), 7.11(2H, dd, J=8.7, J=1.6), 2.74(3H, s), 2.33(3H, s), 2.26(3H, s) | CDCl3 | 115~117 |
| 165 | 7.84(1H, s), 7.55(2H, d, J=8.7), 6.79(2H, d, J=8.7), 3.94(3H, s), 3.01(2H, q, J=7.7), 2.50(3H, s), 2.31(3H, s), 2.25(3H, s), 1.38(3H, t, J=7.7) | CDCl3 | 137~138 |
| 167 | 8.24(1H, d, J=9.2), 8.02(2H, d, J=8.8), 7.33(1H, d, J=9.2), 7.15(2H, d, J=8.8), 2.76(3H, s), 2.42(3H, s), 2.28(3H, s) | CDCl3 | 131~133 |
| 168 | 8.49(1H, s), 8.02(2H, d, J=8.8), 7.36(1H, s), 7.20(2H, d, J=8.8), 2.77(3H, s), 2.42(3H, s), 2.30(3H, s) | CDCl3 | 193~195 |
| 182 | 7.88(1H, d, J=9.0), 7.28(1H, d, J=9.0), 7.14(2H, d, J=8.8), 6.86(2H, d, J=8.8), 5.99(1H, tt, J=53.1, J=2.8), 2.71(3H, s), 2.61(3H, s), 2.45(3H, s), 2.24(3H, s) | CDCl3 | 146~148 |
| 183 | 7.91(1H, d, J=9.1), 7.29(1H, d, J=9.1), 7.14(2H, d, J=9.0), 6.86(2H, d, J=9.0), 5.90(1H, tt, J=52.9, J=2.3), 3.97(3H, s), 3.02(2H, q, J=7.2), 2.60(3H, s), 2.33(3H, s), 1.38(3H, t, J=7.2) | CDCl3 | 103~104.5 |
| 185 | 8.12(1H, d, J=9.2), 7.27(1H, d, J=9.2), 7.21(2H, d, J=9.0), 6.99(2H, d, J=9.0), 5.92(1H, tt, J=53.1, J=2.7), 2.73(3H, s), 2.42(3H, s), 2.26(3H, s) | CDCl3 | 88~91 |
| 186 | 8.16(1H, s, J=9.4), 7.28(1H, d, J=9.4), 7.20(2H, d, J=9.0), 6.98(2H, d, J=9.0), 5.91(1H, tt, J=53.1, J=2.8), 3.95(3H, s), 3.03(2H, q, J=7.7), 2.35(3H, s), 1.38(3H, t, J=7.7) | CDCl3 | oil |
| 189 | 7.89(1H, s), 7.20(2H, d, J=8.9), 7.01(1H, s), 6.98(2H, d, J=8.9), 5.92(1H, tt, J=53.4, J=2.8), 2.70(3H, s), 2.41(3H, s), 2.34(3H, s), 2.22(3H, s) | CDCl3 | 126~128 |
| 190 | 7.94(1H, s), 7.20-6.95(5H, m,) 5.92(1H, tt, J=53.1, J=2.9), 3.88(3H, s), 3.00(2H, q, J=7.7), 2.42(3H, s), 2.31(3H, s), 1.37(3H, t, J=7.7) | CDCl3 | 106.5~108.5 |
| 192 | 8.40(1H, s), 7.27(2H, d, J=9.1), 7.12(2H, d, J=9.1), 6.96(1H, s), 5.94(1H, tt, J=53.1, J=2.8), 2.72(3H, s), 2.29(3H, s), 2.25(3H, s) | CDCl3 | 122~124 |
| 193 | 8.45(1H, s), 7.26-7.08(5H, m), 5.93(1H, tt, J=53.0, J=2.8), 3.86(3H, s), 3.02(2H, q, J=7.4), 2.33(3H, s), 1.40(3H, t, J=7.4) | CDCl3 | 104~106 |

TABLE 20

| | | | |
|---|---|---|---|
| 197 | 7.82(1H, s), 7.09(2H, d, J=9.0), 6.74(2H, d, J=9.0), 5.89(1H, tt, J=53.1, J=2.6), 3.94(3H, s), 3.01(2H, q, J=7.2), 2.51(3H, s), 2.30(3H, s), 2.26(3H, s), 1.38(3H, t, J=7.2) | CDCl3 | 155~157 |
| 208 | 7.83(1H, s), 7.27-6.63(4H, m), 5.85(1H, tt, J=53.1, J=2.9), 3.94(3H, s), 3.01(2H, q, J=7.8), 2.50(3H, s), 2.31(3H, s), 2.26(3H, s), 1.38(3H, t, J=7.8) | CDCl3 | 96~97.5 |
| 209 | 8.06(1H, d, J=9.3), 7.22(1H, d, J=9.3), 6.97(4H, s), 4.34(2H, q, J=8.4), 2.71(3H, s), 2.42(3H, s), 2.26(3H, s) | CDCl3 | 90.5~91.5 |
| 212 | 8.38(1H, s), 7.11-6.99(4H, m), 6.93(1H, s), 4.38(2H, q, J=8.5), 2.71(3H, s), 2.29(3H, s, 2.24(3H, s) | CDCl3 | 149.5~150 |
| 213 | 8.03(1H, d, J=9.4), 7.25-6.87(5H, m), 4.49(1H, m, J=6.0), 2.71(3H, s), 2.42(3H, s), 2.25(3H, s), 1.34(6H, d, J=6.0) | CDCl3 | 115~117 |
| 214 | 8.36(1H, s), 7.06(2H, d, J=9.0), 6.94(2H, d, J=9.0), 6.89(1H, s), 4.54(1H, m, J=6.1) 2.70(3H, s), 2.27(3H, s), 2.23(3H, s), 1.36(6H, d, J=6.1) | CDCl3 | 113~115 |
| 215 | 8.10(1H, d, J=9.0), 7.50(1H, s), 7.23-7.12(2H, m), 6.81(1H, d, J=9.0), 2.72(3H, s), 2.43(3H, s), 2.26(3H, s) | CDCl3 | 92~94 |
| 216 | 8.42(1H, s), 7.55-7.00(3H, m), 6.86(1H, s), 2.72(3H, s), 2.33(3H, s), 2.24(3H, s) | CDCl3 | 145~146.5 |
| 217 | 8.20(1H, d, J=9.0), 7.64(1H, s), 7.37(2H, s), 7.28(1H, d, J=9.0), 2.75(3H, s), 2.42(3H, s), 2.28(3H, s) | CDCl3 | 125~127 |
| 218 | 8.47(1H, s), 7.67(1H, s), 7.49(2H, s), 7.24(1H, s), 2.76(3H, s), 2.37(3H, s), 2.28(3H, s) | CDCl3 | 134~136 |
| 222 | 8.17(1H, d, J=9.2), 7.77(1H, s), 7.45(1H, d, J=8.6), 7.21(1H, d, J=9.2), 6.85(1H, d, J=8.6), 2.74(3H, s), 2.42(3H, s), 2.27(3H, s) | CDCl3 | 110~112 |
| 228 | 8.45(1H, s), 7.81(1H, s), 7.50(1H, d, J=8.6), 7.04(1H, s), 7.01(1H, d, J=8.6), 2.74(3H, s), 2.34(3H, s), 2.27(3H, s) | CDCl3 | 123~125 |
| 247 | 8.15(1H, s, J=9.1), 7.28-6.76(4H, m), 2.73(3H, s), 2.42(3H, s), 2.26(3H, s) | CDCl3 | 100~101.5 |
| 248 | 8.42(1H, s), 7.18-6.86(4H, m), 2.74(3H, s), 2.36(3H, s), 2.27(3H, s) | CDCl3 | 104~105 |
| 249 | 7.89(1H, d, J=9.0), 7.39-6.99(3H, m), 6.64(1H, d, J=9.0), 2.71(3H, s), 2.62(3H, s), 2.45(3H, s), 2.24(3H, s) | CDCl3 | 149~151 |
| 250 | 7.91(1H, d, J=9.2), 7.39-6.99(3H, m), 6.63(1H, d, J=9.0), 3.97(3H, s), 3.02(2H, q, J=7.1), 2.61(3H, s), 2.33(3H, s), 1.38(3H, t, J=7.1) | CDCl3 | 112~114 |
| 252 | 7.77-7.76(2H, m), 7.36-7.33(2H, m), 6.88(1H, d, J=9.2), 2.35(3H, s), 1.95(3H, s) | DMSO-d6 | — |
| 253 | 8.12(1H, d, J=9.2), 7.41-7.10(4H, m), 6.88(1H, d, J=9.2), 2.73(3H, s), 2.43(3H, s), 2.27(3H, s) | CDCl3 | 78~80 |
| 254 | 8.17(1H, d, J=9.1), 7.41-7.09(3H, m), 6.87(1H, d, J=9.1), 3.96(3H, s), 3.03(2H, q, J=7.2), 2.36(3H, s), 1.39(3H, t, J=7.2) | CDCl3 | oil |
| 256 | 7.91(1H, s), 7.42-6.85(4H, m), 2.70(3H, s), 2.42(3H, s), 2.34(3H, s), 2.22(3H, s) | CDCl3 | 126~128 |
| 257 | 7.95(1H, s), 7.41-6.85(4H, m), 3.88(3H, s), 3.00(2H, q, J=7.7), 2.44(3H, s), 2.31(3H, s), 1.37(3H, t, J=7.7) | CDCl3 | 117~118.5 |
| 259 | 8.42(1H, s), 7.46-7.11(4H, m), 6.80(1H, s), 2.72(3H, s), 2.28(3H, s), 2.25(3, s) | CDCl3 | 110~111 |

TABLE 20-continued

| | | | |
|---|---|---|---|
| 260 | 8.46(1H, s), 7.44-7.09(3H, m), 6.93(1H, s), 3.86(3H, s), 3.02(2H, q, J=7.5), 2.33(3H, s), 1.39(3H, t, J=7.5) | CDCl3 | 119~121 |

TABLE 21

| | | | |
|---|---|---|---|
| 262 | 7.84(1H, s), 7.39(1H, d, J=1.7), 6.92(1H, dd, J=9.0, J=1.7), 6.32(1H, d, J=9.0), 3.94(3H, s), 30.1(2H, q, J=7.5), 2.50(3H, s), 2.31(3H, s), 2.26(3H, s)1.38(3H, t, J=7.5) | CDCl3 | 116~117 |
| 269 | 8.16(1H, d, J=9.1), 7.32-6.85(4H, m), 2.74(3H, s), 2.42(3H, s), 2.27(3H, s) | CDCl3 | 115~117 |
| 275 | 8.43(1H, s), 7.35-6.96(4H, m), 2.74(3H, s), 2.37(3H, s), 2.27(3H, s) | CDCl3 | 116~118 |
| 277 | 7.84(1H, s), 7.20(1H, d, J=8.9), 6.87(1H, d, J=2.8), 6.65(1H, dd, J=8.9, J=2.8), 3.95(3H, s), 3.01(2H, q, J=7.3), 2.50(3H, s), 2.31(3H, s), 2.26(3H, s), 1.38(3H, t, J=7.3) | CDCl3 | 164~165 |
| 279 | 8.12(1H, d, J=9.1), 7.31-6.97(4H, m), 2.72(3H, s), 2.42(3H, s), 2.26(3H, s) | CDCl3 | 71~72.5 |
| 280 | 8.41(1H, s), 7.32-6.87(4H, m), 2.72(3H, s), 2.28(3H, s), 2.24(3H, s) | CDCl3 | 119.5~121 |
| 281 | 8.17(1H, d, J=9.1), 7.94(1H, s), 7.51(1H, d, J=8.3), 7.22(1H, d, J=9.1), 6.81(1H, d, J=8.3), 2.74(3H, s), 2.43(3H, s), 2.27(3H, s) | CDCl3 | oil |
| 282 | 8.46(1H, s), 7.97(1H, s), 7.55(1H, d, J=8.5), 7.06(1H, d, J=9.1), 6.98(1H, d, J=8.5), 2.74(3H, s), 2.35(3H, s), 2.27(3H, s) | CDCl3 | 108~109 |
| 308 | 8.08(1H, d, J=9.1), 7.16-7.01(3H, m), 6.75(1H, d, J=9.1), 2.72(3H, s), 2.43(3H, s), 2.33(3H, s), 2.26(3H, s) | CDCl3 | 85.5~86.5 |
| 312 | 8.40(1H, s), 7.21-7.04(3H, m), 6.67(1H, s), 2.71(3H, s), 2.23(9H, s) | CDCl3 | 103~104 |
| 314 | 7.83(1H, s), 7.12(1H, s), 6.81(1H, d, J=8.8), 6.16(1H, d, J=8.8), 3.94(3H, s), 3.01(2H, q, J=7.5), 2.48(3H, s), 2.47(3H, s), 2.31(3H, s), 2.23(3H, s), 1.28(3H, t, J=7.5) | CDCl3 | 126~127 |
| 324 | 7.91(1H, d, J=9.2), 7.38(1H, d, J=2.4), 7.24(H1, d, J=9.2), 7.00(1H, tt, J=8.9, J=2.4), 6.64(1H, d, J=8.9), 5.90(1H, tt, J=53.1, J=2.8), 3.97(3H, s), 3.02(2H, q, J=7.3), 2.62(3H, s), 2.33(3H, s), 1.38(3H, t, J=7.3) | CDCl3 | 94~95.5 |
| 328 | 8.15(1H, d, J=9.1), 7.40-6.97(3H, m), 6.86(1H, d, J=9.1), 5.92(1H, tt, J=53.0, J=2.6), 3.03(2H, q, J=7.4), 2.43(3H, s), 2.29(3H, s), 1.38(3H, t, J=7.4) | CDCl3 | oil |
| 332 | 7.95(1H, s), 7.40(1H, d, J=2.6), 7.08(1H, dd, J=9.0, J=2.6), 7.01(1H, s), 6.88(1H, d, J=9.0), 5.93(1H, tt, J=52.9, J=2.5), 3.88(3H, s), 3.00(2H, q, J=7.5), 2.45(3H, s), 2.31(3H, s), 1.37(3H, t, J=7.5) | CDCl3 | 116~117 |
| 337 | 7.84(1H, s), 7.38(1H, d, J=2.4), 6.90(1H, dd, J=9.0, J=2.4), 6.31(1H, d, J=9.0), 5.89(1H, tt, J=53.0, J=2.7), 3.94(3H, s), 3.01(2H, q, J=7.6), 2.51(3H, s), 2.31(3H, s), 2.26(3H, s), 1.38(3H, t, J=7.6) | CDCl3 | 157.5~159 |
| 351 | 8.05(1H, br.d), 7.71(2H, s), 6.82(1H, d), 2.71(3H, s), 2.45(3H, s), 2.26(3H, s) | CDCl3 | — |
| 352 | 8.45(1H, br.d), 7.76(2H, s), 6.45(2H, s), 2.71(3H, s), 2.23(6H, s) | CDCl3 | — |
| 353 | 8.05(1H, d, J=9.3), 7.35(2H, s), 6.84(1H, d, J=9.3), 2.71(3H, s), 2.45(3H, s), 2.26(3H, s) | CDCl3 | 116~118 |
| 354 | 8.43(1H, s), 7.41(2H, s), 6.45(1H, s), 2.71(3H, s), 2.23(6H, s) | CDCl3 | 139~140.5 |
| 363 | 8.11(1H, d, J=9.2), 7.60-7.00(9H, m), 2.72(3H, s), 2.43(3H, s), 2.26(3H, s) | CDCl3 | 129~130 |
| 364 | 8.41(1H, s), 7.60-7.04(9H, m), 2.73(3H, s), 2.34(3H, s), 2.26(3H, s) | CDCl3 | 120~124 |
| 365 | 8.13(1H, d, J=9.2), 7.68-7.07(8H, m), 2.73(3H, s), 2.43(3H, s), 2.27(3H, s) | CDCl3 | 132~134 |
| 366 | 8.43(1H, s), 7.70-7.16(8H, m), 2.74(3H, s), 2.32(3H, s), 2.26(3H, s) | CDCl3 | 180~181 |

TABLE 22

| | | | |
|---|---|---|---|
| 367 | 7.91(1H, d, J=9.0), 7.44-7.35(5H, m), 5.21(2H, s), 2.68(3H, s), 2.47(3H, s), 2.25(3H, s) | CDCl3 | 132~134 |
| 368 | 8.07(1H, s), 7.44(2H, s, J=8.3), 7.39(2H, d, J=8.3), 6.97(2H, s), 5.49(2H, s), 2.67(3H, s), 2.46(3H, s), 2.22(3H, s) | CDCl3 | 195~197 |
| 369 | 8.06(1H, d, J=8.6), 7.76(2H, d, J=8.3), 7.51(1H, d, J=8.6), 7.44(2H, d, J=8.3), 2.76(3H, s), 2.41(3H, s), 2.28(3H, s) | CDCl3 | 179~181 |
| 370 | 8.12(1H, s), 7.76(2H, d, J=8.3), 7.75(1H, s), 7.46(2H, d, J=8.3), 2.76(3H, s), 2.44(3H, s), 2.27(3H, s) | CDCl3 | 186~188 |
| 371 | 7.75(1H, d, J=9.0), 7.45(2H, d, J=8.6), 7.40(2H, d, J=8.6), 7.08(1H, d, J=9.0), 2.68(3H, s), 2.48(3H, s), 2.25(3H, s) | CDCl3 | 143~144 |
| 372 | 8.05(1H, s), 7.43(4H, s), 7.02(1H, s), 2.68(3H, s), 2.23(3H, s), 2.19(3H, s) | CDCl3 | 162~163 |
| 373 | 8.21(1H, d, J=8.7), 8.15(1H, d, J=8.7), 7.70(2H, d, J=8.7), 7.42(2H, d, J=8.7), 2.72(3H, s), 2.46(3H, s), 2.24(3H, s) | CDCl3 | 158~159.5 |
| 374 | 8.56(1H, d, J=9.0), 8.13(1H, d, J=9.0), 7.87, 2H, d, J=8.3), 7.48(2H, d, J=8.3), 2.74(3H, s), 2.40(3H, s), 2.23(3H, s) | CDCl3 | 234~237 |
| 375 | 8.60(1H, d, J=8.9), 8.21(1H, d, J=8.9), 7.87(2H, d, J=8.5), 7.49(2H, d, J=8.5), 5.39(2H, s), 2.42(3H, s), 2.26(3H, s), 2.20(3H, s) | CDCl3 | 163~165 |
| 376 | 8.78(1H, s), 8.05(1H, s), 7.89(2H, d, J=8.7), 7.49(2H, d, J=8.7), 2.75(3H, s), 2.59(3H, s), 2.29(3H, s) | CDCl3 | 161~164 |
| 377 | 7.88(1H, d, J=8.7), 7.41(1H, d, J=8.7), 7.25(2H, d, J=8.3), 7.11(2H, d, J=8.3), 4.24(2H, s), 2.70(3H, s), 2.46(3H, s), 2.25(3H, s) | CDCl3 | 173~174 |
| 378 | 8.06(1H, s), 7.30-7.11(5H, m), 4.20(2H, s), 2.70(3H, s), 2.38(3H, s), 2.23(3H, s) | CDCl3 | 178~180 |

TABLE 22-continued

| | | | |
|---|---|---|---|
| 397 | 7.71(1H, s), 7.57(2H, d, J=8.7), 7.01(2H, d, J=8.7), 4.32(2H, t, J=6.0), 3.98-3.94(5H, m), 2.97(2H, q, J=7.2), 2.59(3H, s), 2.39(3H, s), 2.34-2.31(2H, m), 2.27(3H, s), 1.34(3H, s) | CDCl3 | 101.5~102.5 |
| 424 | 7.90(1H, br, s), 7.44(1H, d, J=8.3), 7.30(1H, d, J=9.0), 7.13(1H, d, J=2.9), 6.93(1H, dd, J=9.0, J=2.9), 3.95(3H, s), 2.76(3H, s), 2.31(3H, s) | CDCl3 | — |
| 425 | 7.81(1H, d, J=11.5), 7.35(1H, d, J=6.3), 7.29(1H, dq, J=9.0, J=1.2), 7.10(1H, d, J=2.9), 6.91(1H, dd, J=9.0, J=2.9), 2.73(3H, s), 2.44(3H, s), 2.25(3H, s) | CDCl3 | — |
| 433 | 7.52(1H, s), 7.38(1H, d, J=1.7), 7.21(1H, s), 7.04(1H, d, J=9.0), 6.79(1H, d, J=9.0), 3.95(3H, s), 3.91(3H, s), 3.01(2H, q, 7.4), 2.30(3H, s), 1.38(3H, t, J=7.4) | CDCl3 | 107~108 |
| 435 | 8.40(1H, s), 7.49(2H, d, J=8.4), 7.29(2H, d, J=8.4), 7.25(1H, s), 2.72(3H, s), 2.24(3H, s), 2.22(3H, s) | CDCl3 | 126.5~128.5 |
| 436 | 8.46(1H, s), 7.58(1H, s), 7.42(2H, d, J=8.6), 7.28(2H, d, J=8.6), 2.78(3H, s), 2.47(3H, s), 2.30(3H, s) | CDCl3 | 183~185 |
| 437 | 8.90(1H, s), 8.51(1H, s), 7.89(2H, d, J=8.5), 7.32(2H, d, J=8.5), 2.81(3H, s), 2.60(3H, s), 2.36(3H, s) | CDCl3 | 173~175 |
| 438 | 8.38(1H, s), 7.28(2H, d, J=9.2), 7.15(2H, d, J=9.2), 7.00(1H, s), 3.03(3H, s), 2.94(3H, s), 2.71(3H, s), 2.28(3H, s) | CDCl3 | 88~89.5 |
| 439 | 8.40(1H, s), 7.32-7.18(5H, m), 3.18(3H, s), 2.74(3H, s), 2.46(3H, s) | CDCl3 | 148~149 |
| 440 | 8.33(1H, s), 7.52(2H, d, J=8.6), 7.27(2H, d, J=8.6), 5.25(2H, s), 2.71(3H, s), 2.48(3H, s), 2.26(3H, s) | CDCl3 | 183~184 |
| 441 | 8.39(1H, s), 7.42(1H, s), 7.25(2H, d, J=9.1), 7.11(2H, d, J=9.1), 3.80(3H, s), 2.69(3h, s), 2.38(3H, s) | CDCl3 | 106~108 |

TABLE 23

| | | | |
|---|---|---|---|
| 442 | 8.35(1H, s), 7.29-6.87(5H, m), 2.72(3H, s), 2.30(3H, s), 2.24(3H, s) | CDCl3 | 95~96 |
| 443 | 8.40(1H, s), 7.27-6.88(5H, m), 3.86(3H, s), 3.02(2H, q, J=7.5), 2.33(3H, s), 1.40(3H, t, J=7.5) | CDCl3 | 115~116.5 |
| 444 | 8.64(1H, s), 7.26-7.16(3H, m), 6.99(2H, d, J=8.9), 3.84(3H, s), 2.73(3H, s), 2.26(3H, s), 2.26(3H, s) | CDCl3 | 165~167 |
| 447 | 7.76(1H, s), 7.29-7.26(1H, d), 7.23(2H, d, J=9.1), 7.03(2H, d, J=9.1), 2.73(3H, s), 2.39(3H, s), 2.24(3H, s) | CDCl3 | — |
| 448 | 11.60(1H, s), 7.67(1H, d, J=9.0), 7.42-7.38(3H, m), 7.14(2H, d, J=9.3), 2.36(3H, s), 1.93(3H, s) | DMSO-d6 | — |
| 449 | 7.81(1H, br, s), 7.34(1H, d, J=9.5), 7.22(2H, d, J=8.9), 7.04(2H, d, J=8.9), 3.92(3H, s), 2.73(3H, s), 2.36(3H, s) | CDCl3 | — |
| 450 | 7.67(1H, d, J=10.2), 7.17(2H, d, J=8.8), 6.97(2H, d, J=8.8), 3.94(3H, s), 2.73(3H, s), 2.34(3H, s) | CDCl3 | — |
| 451 | 7.65(1H, br, s), 7.17(2H, d, J=9.0), 6.95(2H, d, J=9.0), 2.73(3H, s), 2.41(3H, s), 2.28(3H, s) | CDCl3 | |
| 452 | 7.26(2H, d, J=8.8), 7.04(2H, d, J=8.8), 7.01(1H, s), 2.79(3H, s), 2.31(3H, s), 2.26(3H, s) | CDCl3 | 123.5~125.5 |
| 453 | 7.88(1H, d, J=9.0), 7.49(2H, d, J=8.7), 7.27-7.22(3H, m), 2.70(3H, s), 2.42(3H, s), 2.24(3H, s) | CDCl3 | 104.5~106.5 |
| 454 | 8.16(1H, d, J=8.7), 7.52(1H, d, J=8.7), 7.43(2H, d, J=8.6), 7.29(2H, d, J=8.6), 2.76(3H, s), 2.43(3H, s), 2.28(3H, s) | CDCl3 | 128~130 |
| 455 | 8.45(1H, d, J=8.9), 8.31(1H, d, J=8.9), 8.01(2H, d, J=8.6), 7.37(2H, d, J=8.69), 2.77(3H, s), 2.41(3H, s), 2.26(3H, s) | CDCl3 | 131~133 |
| 456 | 8.11(1H, d, J=9.4), 7.26-6.96(5H, m), 3.24(3H, s), 3.04(3H, s), 2.71(3H, s), 2.29(3H, s) | CDCl3 | 110~112 |
| 457 | 8.08(1H, d, J=9.2), 7.32-7.02(5H, m), 3.28(3H, s), 2.73(3H, s), 2.54(3H, s) | CDCl3 | 123~125 |
| 458 | 8.07(1H, d, J=9.2), 7.24(1H, d, J=9.2), 7.21(2H, d, J=8.2), 7.00(2H, d, J=8.2), 3.73(3H, s9, 2.69(3H, s), 2.44(3H, s) | CDCl3 | 93~85 |
| 459 | 8.03(1H, d, J=9.0), 7.26-7.02(5H, m), 3.95(3H, s), 2.72(3H, s), 2.40(3H, s), 2.22(3H, s) | CDCl3 | 113~114 |
| 460 | 7.85(1H, d, J=8.8), 7.38(1H, t, J=8.8), 7.18(2H, d, J=9.1), 6.98(2H, d, J=9.1), 2.73(3H, s), 2.42(3H, s), 2.30(3H, s) | CDCl3 | — |
| 461 | 8.15(1H, d, J=9.3), 7.28(1H, d, J=9.3), 7.22(2H, d, J=8.8), 6.99(2H, d, J=8.8), 4.45(2H, s), 3.56(3H, s), 2.74(3H, s), 2.27(3H, s) | CDCl3 | — |
| 462 | 8.15(1H, d, J=8.9), 7.28(1H, d, J=8.9), 7.22(2H, d, J=9.2), 6.99(2H, d, J=9.2), 4.98(2H, s), 2.74(3H, s), 2.30(3H, s), 2.21(3H, s) | CDCl3 | — |
| 464 | 7.77(1H, s), 7.52(2H, d, J=8.6), 7.27(2H, d, J=8.6), 4.82(2H, s), 3.97(3H, s), 2.99(2H, q, J=7.3), 2.63(3H, s), 2.46(3H, s), 2.29(3H, s), 1.36(3H, t, J=7.3) | CDCl3 | 121~122 |
| 465 | 7.94(1H, s), 7.20(2H, d, J=8.6), 6.99(2H, d, J=8.6), 3.00(2H, q, J=7.2), 2.59(2H, t, J=7.6), 2.41(3H, s), 2.23(3H, s), 1.70(2H, m), 1.39-1.28(10H, m), 0.89(3H, t, J=7.2) | CDCl3 | — |
| 466 | 7.96(1H, s), 7.21(2H, d, J=8.8), 6.99(2H, d, J=8.8), 6.97(1H, s), 4.33(2H, s), 3.46(3H, s), 3.01(2H, q, J=7.5), 2.42(3H, s), 2.25(3H, s), 1.38(3H, t, J=7.5) | CDCl3 | — |
| 467 | 7.95(1H, s), 7.21(2H, d, J=8.8), 7.08(1H, s), 6.98(2H, d, J=8.8), 4.86(2H, s), 3.00(2H, q, J=7.6), 2.41(3H, s), 2.26(3H, s), 2.14(3H, s), 1.37(3H, t, J=7.6) | CDCl3 | — |

TABLE 24

| | | | |
|---|---|---|---|
| 468 | 7.94(1H, s), 7.46(1H, s), 7.19(2H, d, J=8.9), 6.98(2H, d, J=8.9), 4.51(2H, s), 3.75(3H, s), 2.98(2H, q, J=7.5), 2.41(3H, s), 2.40(3H, s), 1.36(3H, t, J=7.5) | CDCl3 | — |
| 469 | 7.92(1H, s), 7.22(2H, d, J=8.8), 7.02(2H, d, J=8.8), 6.98(1H, s), 3.00(2H, q, J=7.6), 2.42(3H, s), 2.25(3H, s), 1.89(1H, m), 1.36(3H, t, J=7.6), 1.10(2H, m), 1.02(2H, m) | CDCl3 | — |
| 470 | 7.94(1H, s), 7.41(1H, s), 7.19(2H, d, J=8.8), 6.97(2H, d, J=8.8), 3.83(3H, s), 3.99(2H, q, J=7.6), 2.40(3H, s), 2.38(3H, s), 1.36(3H, t, J=7.6) | CDCl3 | — |
| 471 | 7.94(1H, s), 7.38(1H, s), 7.19(2H, d, J=8.8), 6.99(2H, d, J=8.8), 5.17(2H, s), 3.83(2H, t, J=4.6), 3.47(2H, t, J=4.6), 3.33(3H, s), 3.00(2H, q, J=7.6), 2.41(3H, s), 2.39(3H, s), 1.36(3H, t, J=7.6) | CDCl3 | — |
| 472 | 7.49(1H, s), 7.19(2H, s, J=8.7), 7.12(1H, s), 6.98(2H, d, J=8.7), 3.95(3H, s), 2.70(3H, s), 2.36(3H, s), 2.21(3H, s) | CDCl3 | 126~128 |
| 473 | 7.52(1H, s), 7.24(1H, s), 7.18(2H, d, J=8.8), 6.98(2H, d, J=8.8), 3.96(3H, s), 3.90(3H, s), 3.01(2H, q, J=7.3), 2.30(3H, s), 1.38(3H, t, J=7.3) | CDCl3 | 115~116 |
| 496 | 8.45(1H, s), 7.45-7.10(3H, m), 6.78(1H, s), 5.95(1H, tt, J=53.1, J=2.8), 3.01(2H, q, J=7.7), 2.28(3H, s), 2.27(3H, s), 1.39(3H, t, J=7.7) | CDCl3 | 126~128 |
| 497 | 7.52(1H, s), 7.22(1H, s), 7.17(2H, d, J=9.1), 6.99(2H, d, J=9.1), 5.91(1H, tt, J=52.9, J=2.3), 3.97(3H, s), 3.90(3H, s), 3.01(2H, q, J=7.3), 2.30(3H, s), 1.38(3H, s, J=7.3) | CDCl3 | 107.5~108.5 |
| 539 | 7.90(1H, d, J=9.0), 7.29(1H, d, J=9.0), 7.11(2H, d, J=9.0), 6.86(2H, d, J=9.0), 6.06(1H, dt, J=53.4, J=2.5), 3.97(3H, s), 3.02(2H, q, J=7.7), 2.60(3H, s), 2.32(3H, s), 1.38(3H, t, J=7.7) | CDCl3 | oil |
| 540 | 7.94(1H, s), 7.17(1H, s), 7.13(2H, d, J=7.2), 6.97(2H, d, J=7.2), 6.08(1H, dt, J=53.4, J=2.5), 3.87(3H, s), 3.00(2H, q, J=7.6), 2.41(3H, s), 2.31(3H, s), 1.37(3H, t, J=7.6) | CDCl3 | 84~86 |
| 541 | 7.83(1H, s), 7.07(2H, d, J=8.9), 6.74(2H, d, J=8.9), 6.05(1H, dt, J=53.4, J=2.4), 3.94(3H, s), 3.01(2H, q, J=7.2), 2.50(3H, s), 2.26(3H, s), 1.38(3H, t, J=7.2). | CDCl3 | 86~88 |
| 569 | 7.81(1H, J=11.2), 7.43(1H, d, J=8.9), 7.12(1H, d, J=2.9), 6.88(1H, dd, J=8.9, J=2.9), 3.96(3H, s), 2.74(3H, s), 2.30(3H, s) | CDCl3 | — |
| 572 | 8.04(2H, d, J=8.9), 7.83(1H, br, s), 7.40(1H, d, J=8.5), 7.01(2H, d, J=8.9), 4.73(2H, q, J=7.2), 2.73(3H, s), 2.43(3H, s), 2.25(3H, s), 1.39(3H, t, J=7.2) | CDCl3 | — |
| 573 | 8.01(1H, d, J=8.9), 7.87(1H, dd, J=9.0, J=1.5), 7.42(1H, t, J=9.0), 6.97(2H, d, J=8.9), 4.36(2H, q, J=7.1), 2.73(3H, s), 2.40(3H, s), 2.30(3H, s), 1.38(3H, t, J=7.1) | CDCl3 | — |
| 574 | 7.83(1H, d, J=9.0), 7.26(1H, d, J=9.0), 7.10(2H, d, J=8.5), 6.78(2H, d, J=8.5), 2.70(3H, s), 2.62(3H, s), 2.44(3H, s), 2.31(3H, s), 2.23(3H, s) | CDCl3 | 106~107 |
| 575 | 7.87(1H, s), 7.15(2H, d, J=8.6), 6.99(1H, s), 6.87(2H, d, J=8.6), 2.68(3H, s), 2.42(3H, s), 2.34(3H, s), 2.32(3H, s), 2.21(3H, s) | CDCl3 | 143~144 |
| 576 | 7.76(1H, d, J=11.7), 7.29(1H, d, J=8.5), 7.10(1H, d, J=8.3), 6.8(1H, d, J=2.7), 6.77(1H, dd, J=8.3, J=2.7), 3.90(3H, s), 2.71(3H, s), 2.27(3H, s), 2.25(3H, s), 2.24(3H, s) | CDCl3 | — |
| 577 | 7.76(1H, d, J=11.2), 7.19(2H, d, J=8.6), 7.16(1H, d, J=8.5), 6.96(2H, d, J=8.6), 2.70(3H, s), 2.65(2H, q, J=7.7), 2.35(3H, s), 2.22(3H, s), 1.24(3H, t, J=7.7) | CDCl3 | — |
| 578 | 7.83(1H, br, s), 7.64(2H, d, J=8.9), 7.47(1H, d, J=8.3), 7.03(2H, d, J=8.9), 3.94(3H, s), 2.74(3H, s), 2.30(3H, s) | CDCl3 | — |
| 579 | 7.68(1H, d, J=11), 7.61(2H, d, J=8.8), 6.99(2H, d, J=8.8), 3.94(3H, s), 2.74(3H, s), 2.34(3H, s) | CDCl3 | — |
| 580 | 7.65(1H, d, J=11), 7.61(2H, d, J=8.8), 6.99(2H, d, J=8.8), 2.72(3H, s), 2.40(3H, s), 2.28(3H, s) | CDCl3 | — |
| 581 | 7.82(1H, d, J=11.0), 7.64(2H, d, J=8.5), 7.34(1H, d, J=8.3), 7.03(2H, d, J=8.5), 2.73(3H, s), 2.42(3H, s), 2.25(3H, s) | CDCl3 | — |
| 582 | 7.90(1H, br, s), 7.61(2H, d, J=8.8), 7.46(1H, t, J=6.9), 6.99(2H, d, J=8.8), 3.94(3H, s), 2.76(3H, s), 2.36(3H, s) | CDCl3 | — |

TABLE 25

| | | | |
|---|---|---|---|
| 617 | 7.81(1H, d, J=11.2), 7.43(1H, d, J=8.5), 7.36(1H, t, J=8.5), 7.00(1H, m), 6.93(2H, m), 3.93(3H, s), 2.73(3H, s), 2.29(3H, s) | CDCl3 | — |
| 618 | 7.87(1H, d, J=9.0), 7.42(1H, t, J=8.7), 7.33(1H, t, J=8.4), 6.96(1H, m), 6.89(3H, m), 3.95(3H, s), 2.74(3H, s), 2.36(3H, s) | CDCl3 | — |
| 634 | 7.81(1H, d, J=10.2), 7.43(1H, d, J=2.0), 7.42(1H, m), 7.41(1H, m), 7.34(1H, br.s), 7.14(1H, m), 3.92(3H, s), 2.73(3H, s), 2.29(3H, s) | CDCl3 | — |
| 635 | 7.81(1H, d, J=10.5), 7.44-7.41(2H, m), 7.34(1H, s), 7.29(1H, d, J=8.3), 7.14(1H, m), 2.72(3H, s), 2.39(3H, s), 2.24(3H, s) | CDCl3 | — |
| 636 | 7.88(1H, s), 7.39-7.36(3H, m), 7.28(1H, br.s), 7.10(1H, m), 3.95(3H, s), 2.75(3H, s), 2.36(3H, s) | CDCl3 | — |
| 644 | 7.89(1H, d, J=9.2), 7.31-6.74(5H, m), 2.72(3H, s), 2.59(3H, s), 2.45(3H, s), 2.24(3H, s) | CDCl3 | 84~85 |
| 645 | 7.91(1H, s), 7.36-7.74(5H, m), 2.70(3H, s), 2.38(3H, s), 2.37(3H, s), 2.22(3H, s) | CDCl3 | — |
| 646 | 8.10(1H, d, J=9.2), 7.40-7.14(4H, m), 6.89(1H, d, J=7.5), 2.72(3H, s), 2.43(3H, s), 2.26(3H, s) | CDCl3 | — |
| 647 | 8.41(1H, s), 7.44-7.11(4H, m), 2.72(3H, s), 2.28(3H, s), 2.24(3H, s) | CDCl3 | 118~119 |

TABLE 25-continued

| | | | |
|---|---|---|---|
| 648 | 7.95(1H, s), 7.19(1H, s), 7.10(1H, d, J=8.8), 6.79-6.74(2H, m), 3.90(3H, s), 3.01(2H, q, J=7.7), 2.39(3H, s), 2.31(3H, s), 1.38(3H, t, J=7.7) | CDCl3 | 132~133.5 |
| 649 | 7.92(1H, d, J=9.2), 7.28(1H, d, J=9.2), 7.06(1H, d, J=8.9), 6.71-6.64), 3.97(3H, s), 3.02(2H, q, J=7.6), 2.58(3H, s), 2.33(3H, s9, 1.38(3H, t, J=7.6) | CDCl3 | 129~130.5 |
| 650 | 7.80(1H, d, J=11.2), 7.41(1H, d, J=8.3), 7.13(1H, d, J=8.1), 6.83(1H, m), 6.81(1H, s), 2.73(3H, s), 2.30(3H, s), | CDCl3 | — |
| 651 | 7.80(1H, d, J=11), 7.33(1H, d, J=8.6), 7.12(1H, d, J=9.0), 6.81(1H, m), 6.79(1H, s), 2.72(3H, s), 2.43(3H, s), 2.25(3H, s) | CDCl3 | — |
| 652 | 7.87(1H, d, J=9.1), 7.40(1H, dd, J=9.1, J=8.3), 7.10(1H, d, J=8.8), 6.80(1H, dd, J=8.8, J=2.8), 6.77(1H, d, J=2.8), 3.95(3H, s), 2.74(3H, s), 2.36(3H, s) | CDCl3 | — |
| 653 | 7.83(1H, s), 7.03(1H, d, J=8.9), 6.59-6.53(2H, m), 3.95(3H, s), 3.01(2H, q, J=7.7), 2.49(3H, s), 2.30(3H, s), 2.26(3H, s), 1.38(3H, t, J=7.7) | CDCl3 | 127.5~128.5 |
| 679 | 8.05-7.98(2H, m), 7.69(1H, d, J=8.8), 7.47(1H, d, J=9.4, 7.00(1H, d, J=8.8), 2.72(3H, s), 2.43(3H, s), 2.26(3H, s) | CDCl3 | 239~240 |
| 680 | 8.15(1H, s), 8.05(1H, s), 7.69(1H, d, J=8.7), 7.51(1H, s), 6.99(1H, d, J=8.7), 2.72(3H, s), 2.46(3H, s), 2.25(3H, s) | CDCl3 | 170~171.5 |
| 683 | 7.85(1H, s), 7.74(1H, s), 7.49(1H, dd, J=9.6, J=2.2), 6.66(1H, d, J=9.6), 4.30(1H, t, J=7.3), 3.98(3H, s), 3.84(1H, t, J=5.7), 2.98(2H, q, J=7.2), 2.61(3H, s), 2.43(3H, s), 2.32(2H, tt, J=7.3, J=5.7), 2.28(3H, s), | CDCl3 | 140~141 |
| 685 | 8.19(1H, s), 8.02(1H, s), 7.84(1H, s), 3.94(3H, s), 3.01(2H, q, J=7.6), 2.48(3H, s), 2.30(3H, s), 2.24(3H, s), 1.36(3H, t, J=7.6) | CDCl3 | 185~186.5 |
| 687 | 8.41(1H, s), 7.96(1H, s), 7.93(1H, dd, J=8.8, J=2.7), 7.52(1H, s), 7.05(1H, d, J=8.8), 3.94(3H, s), 2.73(3H, s), 2.32(3H, s), 2.30(3H, s) | CDCl3 | — |
| 694 | 8.50(1H, d, J=2.7), 8.00(1H, s), 7.62(1H, d, J=8.7), 7.31(1H, s), 7.24(1H, dd, J=8.7, J=2.7), 3.92(3H, s), 3.02(2H, q, J=7.5), 2.38(3H, s), 2.33(3H, s), 1.39(3H, t, J=7.5) | CDCl3 | — |
| 700 | 8.23(1H, q, J=1.1), 8.02(1H, br.s), 7.80(1H, d, J=10.1), 7.70(1H, d), 3.98(3H, s), 2.74(3H, s), 2.31(3H, s) | CDCl3 | — |

Reference Example 1

Synthesis of 4-nitro-1-(4-trifluoromethoxyphenoxy)-2-trifluoromethylbenzene (Compound Represented By Formula (7)

A mixed solution composed of 44.3 g of 1-chloro-4-nitro-2-trifluoromethylbenzene, 98 mL of N,N-dimethylacetamide, 35 g of 4-trifluoromethoxyphenol, and 20.4 g of potassium carbonate was stirred with heating at 90 to 100° C. for 3 hr. This reaction solution was concentrated under the reduced pressure. Ethyl acetate was then added to and dissolved in the residue, and the solution was washed with brine. The solution was then concentrated under the reduced pressure. n-Hexane was added to the residue, and the precipitated crystals were collected by filtration to give 66.9 g of 4-nitro-1-(4-trifluoromethoxyphenoxy)-2-trifluoromethylbenzene (yield 92.7%).

Reference Example 2

Synthesis of 4-(4-trifluoromethoxyphenoxy)-3-trifluoromethylaniline (Compound Represented By Formula (5))

Iron powder (72.7 g), 251 mL of ethanol, 103 mL of distilled water, and 0.55 mL of 35% hydrochloric acid were mixed together, and the mixture was heated to reflux. Subsequently, a solution of 66.9 g of 4-nitro-1-(4-trifluoromethoxyphenoxy)-2-trifluoromethylbenzene dissolved in 77 mL of ethanol was added dropwise to the mixed solution, and the mixture was heated under reflux for 2.5 hr. The reaction solution was cooled to room temperature, sodium bicarbonate water was added thereto, and the mixture was filtered. The filtrate was concentrated under the reduced pressure, and ethyl acetate and brine were added to the residue, followed by separation. The ethyl acetate layer was washed with brine and was then concentrated under the reduced pressure to give 61.0 g of 4-(4-trifluoromethoxyphenoxy)-3-trifluoromethylaniline (yield 99%).

Reference Example 3

Synthesis of 2-chloro-1-(4-chlorophenylthio)-4-nitrobenzene (Compound Represented By Formula (7b))

Potassium carbonate (10.4 g) was added to a mixture composed of 50 mL of N,N-dimethylacetamide, 19.2 g of 1,2-dichloro-4-nitrobenzene, and 14.5 g of 4-chlorobenzenethiol. This mixed solution was stirred at 35 to 40° C. for 2.5 hr. This reaction solution was poured into 500 mL of iced water, and the precipitated crystals were collected by filtration to give 27.8 g of 2-chloro-1-(4-chlorophenylthio)-4-nitrobenzene (yield 92.5%).

Reference Example 4

Synthesis of 1-(4-chlorobenzenesulfonyl)-4-nitrobenzene (Compound Represented By Formula (7d))

A 35% aqueous hydrogen peroxide solution (13.6 g) was added dropwise to a mixture composed of 14.0 g of 1-(4-chlorophenylthio)-4-nitrobenzene and 47 mL of acetic acid. The mixed solution was stirred with heating at 70 to 80° C. for 1.5 hr. Thereafter, this reaction solution was cooled and was poured into water, and the precipitated crystals were collected by filtration to give 22.0 g of 1-(4-chlorobenzene sulfonyl)-4-nitrobenzene.

Reference Example 5

Synthesis of 2-chloro-1-(4-chlorobenzyloxy)-4-nitrobenzene (Compound Represented By Formula (7e))

N,N-Dimethylacetamide (42 mL), 16.2 g of 1,2-dichloro-4-nitrobenzene, 12 g of 4-chlorobenzyl alcohol, and 8.7 g of potassium carbonate were mixed together, and the mixture was stirred with heating at 100 to 140° C. for 30 hr. This reaction solution was concentrated under the reduced pressure. The residue was dissolved in 100 mL of ethyl acetate and 100 mL of toluene, and the solution was washed with water and brine. The organic layer was concentrated under the reduced pressure, and the residue was recrystallized from ethanol to give 11.77 g of 2-chloro-1-(4-chlorobenzyloxy)-4-nitrobenzene (yield 46.9%).

Reference Example 6

Synthesis of (2-chloro-4-nitrophenyl)-(4'-chlorophenyl)methanone (Compound Represented By Formula (7f))

2-Chloro-4-nitrobenzoyl chloride (23.1 g) was added dropwise to a mixture composed of 11.8 g of monochlorobenzene and 13.3 g of aluminum chloride. The mixed solution was stirred with heating at 40° C. for 6 hr and was then added dropwise to 45 mL of warm water. Further, toluene and ethyl acetate were added to the mixed solution followed by separation and washing with sodium bicarbonate water and brine. The organic layer was concentrated under the reduced is pressure. n-Hexane was added to the residue, and the precipitated crystals were collected by filtration to give 24.0 g of (2-chloro-4-nitrophenyl)-(4'-chlorophenyl)methanone (yield 81%).

Reference Example 7

Synthesis of (4-amino-2-chlorophenyl)-(4'-chlorophenyl)methanone (Compound Represented By Formula (5f))

Iron powder (12 g), 42 mL of ethanol, 17 mL of distilled water, and 0.09 mL of 35% hydrochloric acid were mixed together, and the mixture was heated to reflux. Subsequently, (2-chloro-4-nitrophenyl)-(4'-chlorophenyl)methanone (8.9 g) dissolved in 12.8 mL of ethanol was added dropwise to the mixed solution, and the mixture was heated under reflux for one hr. This mixed solution was then cooled to room temperature, sodium bicarbonate water was then added thereto, and the mixture was filtered. The filtrate was concentrated under the reduced pressure, and ethyl acetate and brine were added to the residue, followed by separation. The ethyl acetate layer was washed with brine and was then concentrated under the reduced pressure to give 7.56 g of (4-amino-2-chlorophenyl)-(4'-chlorophenyl)methanone (yield 95%).

Reference Example 8

Synthesis of 3-chloro-4-(4-chlorobenzyl)aniline (compound represented by formula (5 g))

Iodine (1 g) and 50 mL of acetic acid were mixed together, 2.53 g of 50% phosphoric acid was added thereto, and the mixture was heated with stirring to reflux. Subsequently, a mixture composed of 3.2 g of (4-amino-2-chlorophenyl)-(4'-chlorophenyl)methanone and 15 mL of acetic acid were added dropwise to the mixed solution. This solution was heated under reflux for 134 hr, was then cooled and was poured into water. Ethyl acetate was added to the mixed solution followed by separation and washing with brine. The ethyl acetate layer was concentrated to give 3.0 g of 3-chloro-4-(4-chlorobenzyl)aniline (yield 100%).

Reference Example 9

Synthesis of 4-nitro-4'-trifluoromethoxy-2-trifluoromethylbiphenyl (Compound Represented By Formula (7h))

1-Bromo-4-nitro-3-trifluorobenzene (2.5 g), 2.1 g of 4-trifluoromethoxyphenylboric acid, 9.3 mL of ethanol, and 18.3 g of toluene were mixed together to prepare a solution. An aqueous solution of 0.93 g of sodium carbonate dissolved in 9 g of water was added to the solution. Tetrakis(triphenylphosphine)palladium(0) (0.067 g) was added thereto, and the mixture was heated under reflux for 4 hr. The reaction mixture was cooled, ethyl acetate and distilled water were then added thereto, followed by separation and washing with brine. The ethyl acetate layer was concentrated to give 3.54 g of 4-nitro-4'-trifluoromethoxy-2-trifluoromethylbiphenyl (yield 100%).

Reference Example 10

Synthesis of 3-chloro-2-(2.6-dimethyl-4-nitrophenoxy)-5- trifluoromethylpyridine (Compound Represented By Formula (7a))

2,3-Dichloro-5-trifluoromethylpyridine (1.04 g), 0.8 g of 2,6-dimethyl-4-nitrophenol, and 0.5 g of potassium carbonate were added to 3 mL of dimethylacetamide, and the mixture was allowed to react at 155 to 165° C. for one hr. The reaction mixture was cooled, ethyl acetate and distilled water were then added thereto, followed by separation and washing with brine. The ethyl acetate layer was concentrated to give 2.01 g of 3-chloro-2-(2,6-dimethyl-4-nitrophenoxy)-5-trifluoromethylpyridine (yield 100%).

Reference Example 11

Synthesis of 5-chloro-2-(2-chloro-4-nitrophenoxy)pyridine (Compound Represented By Formula (7a))

1,2-Dichloro-4-nitrobenzene (19.2 g), 12.9 g of 5-chloropyridine-2-ol, and 10.4 g of potassium carbonate were added to 50 mL of dimethylacetamide, and the mixture was allowed to react at 90 to 110° C. for 15 hr. The reaction mixture was cooled, ethyl acetate and brine were then added thereto, followed by separation and washing with brine. The ethyl acetate layer was concentrated, and the precipitated crystals were collected by filtration. The filtrate was concentrated, and the crude product thus obtained was purified by column chromatography on silica gel (BW300, manufactured by Fuji Sylysia Chemical Ltd., solvent: n-hexane/ethyl acetate) to give 15.75 g of 5-chloro-2-(2-chloro-4-nitrophenoxy)pyridine (yield 55.2%).

Reference Example 12

Synthesis of 1,3-Dimethyl-5-nitro-2-(3-(4-trifluoromethylphenoxy)-propoxy)benzene (compound represented by formula (7i))

2,6-Dimethyl-4-nitrophenol (5.2 g) and 12.6 g of 1,3-dibromopropane were added to 19 mL of distilled water, the mixture was stirred, and 7.51 g of a 16.6% aqueous sodium hydroxide solution was then added thereto. Further, the mixture was heated under reflux while adding 2.46 g of a 30% aqueous sodium hydroxide solution for 5 hr. The reaction mixture was cooled, and ethyl acetate and brine were added thereto, followed by separation and washing with brine. The ethyl acetate layer was concentrated under the reduced pressure, and the crude product was purified by column chromatography on silica gel (BW300, manufactured by Fuji Sylysia Chemical Ltd., solvent: n-hexane/ethyl acetate) to give 4.97 g of 2-(3-bromopropoxy)-1,3-dimethyl-5-nitrobenzene. Next, 1.0 g of the product, 0.57 g of 4-trifluoromethylphenol, 2 mL of dimethylacetamide, and 0.36 g of potassium carbonate were mixed together, and the mixture was heated at 90 to 100° C. for one hr. The reaction solution was cooled and was then poured into water, and the mixture was extracted with ethyl acetate. The ethyl acetate layer was washed with a 2% aqueous sodium hydroxide solution and brine and was then concentrated under the reduced pressure to give 1.28 g of 1,3-dimethyl-5-nitro-2-(3-(4-trifluoromethylphenoxy)propoxy)benzene.

Preparation Example 1

Wettable Powder

| | |
|---|---|
| Compound 90 | 30 wt % |
| Clay | 30 wt % |
| Diatomaceous earth | 35 wt % |
| Calcium lignin sulfonate | 4 wt % |
| Sodium laurylsulfate | 1 wt % |

The above ingredients were intimately mixed together, and the mixture was ground to prepare wettable powder.

Preparation Example 2

Dust

| | |
|---|---|
| Compound 90 | 2 wt % |
| Clay | 60 wt % |
| Talc | 37 wt % |
| Calcium stearate | 1 wt % |

The above ingredients were intimately mixed together to prepare dust.

Preparation Example 3

Emulsifiable Concentrate

| | |
|---|---|
| Compound 90 | 20 wt % |
| N,N-Dimethylformamide | 20 wt % |
| Solvesso 150 (Exxon Mobil Corporation) | 50 wt % |
| Polyoxyethylene alkylaryl ether | 10 wt % |

The above ingredients were homogeneously mixed and dissolved to prepare emulsifiable concentrate.

Preparation Example 4

Granules

| | |
|---|---|
| Compound 2 | 5 wt % |
| Bentonite | 40 wt % |
| Talc | 10 wt % |
| Clay | 43 wt % |
| Calcium lignin sulfonate | 2 wt % |

The above ingredients were homogeneously ground and intimately mixed together. Water was added to the mixture, followed by thorough kneading. Thereafter, the kneaded product was granulated and dried to prepare granules.

Preparation Example 5

Floables

| | |
|---|---|
| Compound 2 | 25 wt % |
| POE polystyrylphenyl ether sulfate | 5 wt % |
| Propylene glycol | 6 wt % |
| Bentonite | 1 wt % |
| 1% aqueous xanthan gum solution | 3 wt % |
| PRONAL EX-300 | 0.05 wt % |
| (Toho Chemical Industry Co., Ltd.) | |
| ADDAC 827 | 0.02 wt % |
| (K.I. Chemical Industry Co., Ltd.) | |
| Water | 59.93 wt % |

All the above ingredients except for the 1% aqueous xanthan gum solution and a suitable amount of water were premixed together, and the mixture was then ground by a wet grinding mill. Thereafter, the 1% aqueous xanthan gum solution and the remaining water were added to the ground product to prepare 100 wt % floables.

Test Example 1

Pesticidal Effect Against *Plutella xylostella*

A cabbage leaf disk having a diameter of 5 cm was placed in a plastic cup. Test compounds, which had been diluted to designated concentrations by the addition of a 50% aqueous acetone solution (Tween 20, 0.05%), were spread over the cabbage leaf disk by means of a spray gun, and the cabbage leaf disk was then air dried. Five larvae at the second instar of *Plutella xylostella* were released in the cup. The cup was then lidded, and the larvae were reared in a chamber at a constant temperature (25° C.). Three days after the treatment, the larvae were observed for survival or death, and the death rate of larvae was calculated based on the observation results. As a result, for the compounds according to the present invention shown in Tables 15 to 25 exhibited a death rate of not less than 80% at a concentration of not more than 200 ppm.

Test Example 2

Pesticidal Effect Against *Spodoptera litura*

A cabbage leaf disk having a diameter of 5 cm was placed in a plastic cup. Test compounds, which had been diluted to designated concentrations by the addition of a 50% aqueous acetone solution (Tween 20, 0.05%), were spread over the cabbage leaf disk by means of a spray gun, and the cabbage leaf disk was then air dried. Five larvae at the third instar of *Spodoptera litura* were released in the cup. The cup was then lidded, and the larvae were reared in a chamber at a constant temperature (25° C.). Three days after the treatment, the larvae were observed for survival or death, and the death rate of larvae was calculated based on the observation results. As a result, for the compounds according to the present invention shown in Tables 15 to 25 exhibited a death rate of not less than 80% at a concentration of not more than 200 ppm.

Test Example 3

Pesticidal Effect Against *Myzus persicae*

A cabbage leaf disk having a diameter of 2.8 cm was placed in a plastic schale. Test compounds, which had been diluted to designated concentrations by the addition of a 50% aqueous acetone solution (Tween 20, 0.05%), were spread over the cabbage leaf disk by means of a spray gun, and the cabbage leaf disk was then air dried. Thereafter, ten larvae at the first instar of *Myzus persicae* were released in the schale. The schale was then lidded, and the larvae were reared in a chamber at a constant temperature (25° C.). Two days after the treatment, the larvae were observed for survival or death, and the death rate of larvae was calculated based on the observation results. As a result, for the compounds according to the present invention shown in Tables 15 to 25 exhibited a death rate of not less than 80% at a concentration of not more than 500 ppm.

Test Example 4

Miticidal Effect Against *Tetranychus cinnabarinus*

A kidney leaf disk having a diameter of 2 cm was placed on agar. Seven female adult mites of *Tetranychus cinnabarinus* were released on the kidney leaf disk. The female adult mites were allowed to oviposit in a chamber kept at a constant temperature (25° C.) for 24 hr. The female adult mites were then removed from the kidney leaf disk. Test compounds, which had been diluted to designated concentrations by the addition of a 50% aqueous acetone solution (Tween 20, 0.05%), were spread over the leaf disk by means of a spray gun, and the leaf disk was then air dried. Thereafter, the leaf disk was stored in a constant-temperature chamber of 25° C. Seven days after the treatment, the test system was observed for hatching of eggs and survival or death of larva ticks and nymphs, and the unhatching rate of eggs and the death rate of larva ticks/nymphs were calculated based on the observation results. The sum of the unhatching rate of eggs and the death rate of larva ticks/nymphs was determined as the total death rate. As a result, for the compounds according to the present invention shown in Tables 15 to 25 exhibited a death rate of not less than 80% at a concentration of not more than 500 ppm.

Test Example 5

Control Effect Against *Laodel phax striatellus*

Test compounds, which had been diluted to designated concentrations by the addition of a 50% aqueous acetone solution (Tween 20, 0.05%), were spread over four rice seedlings (7 days after sowing) sowed in a plastic pot by means of a spray gun, followed by air drying. Thereafter, this pot was covered by a plastic cylinder, and ten larvae at the second instar of *Laodel phax striatellus* were released in the pot. The pot was then lidded, and the larvae were reared in a chamber at a constant temperature (25° C.). Three days after the treatment, the larvae were observed for survival or death, and the death rate of larvae was calculated based on the observation results. As a result, for the compounds according to the present invention shown in Tables 15 to 25 exhibited a death rate of not less than 80% at a concentration of not more than 500 ppm.

Test Example 6

Control Effect Against *Trigonotylus caelestialium*

One wheat seedling was immersed in test compounds which had been diluted to designated concentrations by the addition of a 50% aqueous acetone solution (Tween 20, 0.05%) for 30 sec. This wheat seedling was air dried and was then placed in a glass cylinder. Two larvae at the second instar of *Trigonotylus caelestialium* were released in the glass cylinder. Thereafter, the cylinder was lidded, and the larvae were reared in a chamber at a constant temperature (25° C.). During the test, the wheat was allowed to suck water through the bottom of the glass cylinder for feeding water to the wheat. Three days after the treatment, the larvae were observed for survival or death, and the death rate of larvae was calculated based on the observation results. As a result, for the compounds according to the present invention shown in Tables 15 to 25 exhibited a death rate of not less than 80% at a concentration of not more than 500 ppm.

Test Example 7

Pesticidal Effect Against *Bemisia tabaci Genn*

A cucumber leaf was cut into a size of 6.0 cm in diameter and was placed on a water-wetted absorbent cotton. Test compounds which had been diluted to designated concentrations by the addition of a 50% aqueous acetone solution (Tween 20, 0.05%) were sprayed in an amount of 2 mL over the cucumber leaf from a spraying tower. After air drying, this cucumber leaf was placed in a plastic cup, and 20 female adults of *Bemisia tabaci Genn.* were released in the cup. The cup was turned upside down and was allowed to stand in a chamber kept at a constant temperature (25° C.). Five days after the treatment, the pests were observed for survival or death, and the death rate of the pests was calculated based on the observation results. As a result, for the compounds according to the present invention shown in Tables 15 to 25 exhibited a death rate of not less than 80% at a concentration of not more than 500 ppm.

Test Example 8

Pestcidal Effect Against *Thrips palmi KARNY*

A cucumber leaf was cut into a size of 2.5 cm square and was placed on a water-wetted absorbent cotton. Test compounds which had been diluted to designated concentrations by the addition of a 50% aqueous acetone solution (Tween 20, 0.05%) were sprayed in an amount of 2 mL over the cucumber leaf from an spraying tower. After air drying, this cucumber leaf was placed in a plastic cup, and ten larvae at the first instar of *Thrips palmi KARNYU* were released in the cup. The cup was allowed to stand in a chamber kept at a constant temperature (25° C.). Two days after the treatment, the larvae were observed for survival or death, and the death rate of larvae was calculated based on the observation results. As a result, for the compounds according to the present invention shown in Tables 15 to 25 exhibited a death rate of not less than 80% at a concentration of not more than 500 ppm.

Comparative Example

Compound No. 136 described in WO 98/055460 and compound No. 46 described in Japanese Patent No. 2633377 were tested for insecticidal activity according to the methods described in Test Examples 1 to 5. The results were as shown in Table 26.

$X_1$ and $X_2$, each independently represent a hydrogen atom, a halogen atom, $C_{1-4}$ alkyl optionally substituted by halogen atom, $C_{1-4}$ alkyloxy, or $C_{1-4}$ alkyloxycarbonyl, provided that $X_1$ and $X_2$ do not simultaneously represent a hydrogen atom, $X_3$ represents a hydrogen atom, $W_1$ represents a nitrogen atom or C—$Y_1$, $W_2$ represents a nitrogen atom or C—$Y_2$, $W_3$ represents a nitrogen atom or C—$Y_3$, provided that, when $W_1$ represents a nitrogen atom, $W_2$ and $W_3$ represent C—$Y_2$ and C—$Y_3$, respectively; when $W_2$ represents a nitrogen atom, $W_1$ and $W_3$ represent C—$Y_1$ and C—$Y_3$, respectively; and when $W_3$

TABLE 26

| | Concentration, ppm | Death rate, % | | | | |
| --- | --- | --- | --- | --- | --- | --- |
| | | Plutella xylostella 200 | Spodoptera litura 200 | Myzus persicae 500 | Laodelphax striatellus 500 | Tetranychus cinnabarinus 500 |
| WO 98055460 Compund No. 136 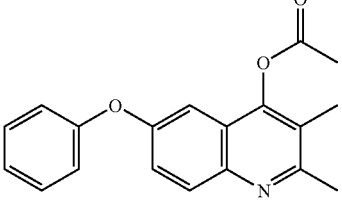 | | 0 | 0 | 0 | 0 | 0 |
| JP 2633377 Compund No. 46 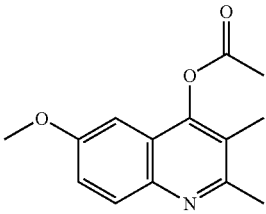 | | 0 | 10 | 0 | 0 | 0 |

The invention claimed is:

1. A compound represented by formula (I) or an agriculturally and horticulturally acceptable acid addition salt thereof:

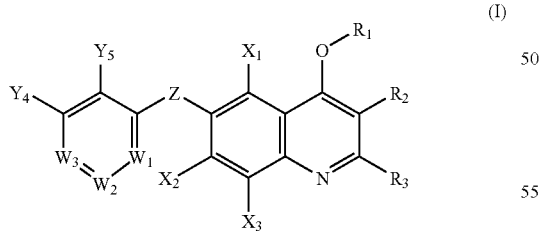

wherein $R_1$ represents a hydrogen atom; or $COR_4$ wherein $R_4$ represents $C_{1-4}$ alkyl, $OR_5$ wherein $R_5$ represents $C_{1-4}$ alkyl, or $NR_6R_7$ wherein $R_6$ and $R_7$ each independently represent a hydrogen atom or $C_{1-18}$ alkyl, $R_2$ represents $C_{1-4}$ alkyl, $R_3$ represents $C_{1-4}$ alkyl, alternatively $R_2$ and $R_3$ together represent —$(CH_2)_m$— wherein m is 3 or 4, represents a nitrogen atom, $W_1$ and $W_2$ represent C—$Y_1$ and C—$Y_2$, respectively, $Y_1$, $Y_2$, $Y_3$, $Y_4$, and $Y_5$ each independently represent a hydrogen atom, A, or B, provided that $W_1$, $W_2$, and $W_3$ respectively represent C—$Y_1$, C—$Y_2$, and C—$Y_3$, and, when Z represents a bond, methylene optionally substituted by one or two methyl groups, or an oxygen atom, at least one of $Y_1$, $Y_2$, $Y_3$, $Y_4$, and $Y_5$ represents A, wherein A represents a group selected from the group consisting of:

$C_{1-8}$ alkyl which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{2-8}$ alkenyl which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{1-8}$ alkyloxy which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{2-8}$ alkenyloxy which is substituted by one or more groups selected from one or more halogen atoms which may be the same or different, $C_{1-4}$ alkyloxy substituted by one or more halogen atoms which may be the same or different, and $C_{2-4}$ alkenyloxy substituted by one or more halogen atoms which may be the same or different;

$C_{1-8}$ alkyloxycarbonyl which is optionally substituted by one or more halogen atoms which may be the same or different, and/or $C_{1-4}$ alkyloxy substituted by one or more halogen atoms which may be the same or different;

$C_{1-8}$ alkylthio which is optionally substituted by one or more halogen atoms which may be the same or different, and/or $C_{1-4}$ alkyloxy substituted by one or more halogen atoms which may be the same or different;

$C_{2-8}$ alkenylthio which is optionally substituted by one or more halogen atoms which may be the same or different, and/or $C_{1-4}$ alkyloxy substituted by one or more halogen atoms which may be the same or different;

$C_{1-8}$ alkylsulfinyl which is optionally substituted by one or more halogen atoms which may be the same or different, and/or $C_{1-4}$ alkyloxy substituted by one or more halogen atoms which may be the same or different;

$C_{2-8}$ alkenylsulfinyl which is optionally substituted by one or more halogen atoms which may be the same or different, and/or $C_{1-4}$ alkyloxy substituted by one or more halogen atoms which may be the same or different;

$C_{1-8}$ alkylsulfonyl which is optionally substituted by one or more halogen atoms which may be the same or different, and/or $C_{1-4}$ alkyloxy substituted by one or more halogen atoms which may be the same or different;

$C_{2-8}$ alkenylsulfonyl which is optionally substituted by one or more halogen atoms which may be the same or different, and/or $C_{1-4}$ alkyloxy substituted by one or more halogen atoms which may be the same or different;

phenyl which is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different; and phenoxy which is substituted by one or more halogen atoms which may be the same or different, $C_{1-4}$ alkyl substituted by one or more halogen atoms which may be the same or different, or $C_{1-4}$ alkyloxy substituted by one or more halogen atoms which may be the same or different, B represents a group selected from the group consisting of a halogen atom, $C_{1-4}$ alkyl, $C_{1-4}$ alkyloxy, nitro, and cyano, alternatively adjacent two of $Y_1$, $Y_2$, $Y_3$, $Y_4$, and $Y_5$ may together represent —O—$(CH_2)_n$—O— optionally substituted by halogen atom, —$(CH_2)_n$——O— optionally substituted by halogen atom, —S—$(CH_2)_n$—S— optionally substituted by halogen atom, —$(CH_2)_n$—S— optionally substituted by halogen atom, or —$(CH_2)_n$— optionally substituted by halogen atom, wherein n is 1, 2, or 3, Z represents an oxygen atom, $OCH_2$, or $O(CH_2)_3O$.

2. The compound according to claim 1, wherein $W_1$, $W_2$, and $W_3$ represent C—$Y_1$, C—$Y_2$, and C—$Y_3$, respectively, $Y_1$, $Y_2$, $Y_3$, $Y_4$, and $Y_5$ each independently represent a hydrogen atom, A or B, provided that, when Z represents a bond, methylene optionally substituted by one or two methyl, or an oxygen atom, at least one of $Y_1$, $Y_2$, $Y_3$, $Y_4$, and $Y_5$ represents A, wherein A represents a group selected from the group consisting of:

$C_{1-8}$ alkyl which is substituted by one or more halogen atoms which may be the same or different;

$C_{1-8}$ alkyloxy which is substituted by one or more halogen atoms which may be the same or different, and/or $C_{1-4}$ alkyloxy substituted by one or more halogen atoms which may be the same or different;

$C_{1-8}$ alkyloxycarbonyl;

$C_{1-8}$ alkylthio which is substituted by one or more halogen atoms which may be the same or different;

$C_{1-8}$ alkylsulfonyl which is subsituted by one or more halogen atoms which may be the same or different;

phenyl which is substituted by one or more halogen atoms which may be the same or different, or $C_{1-4}$ alkyl substituted by one or more halogen atoms which may be the same or different; and phenoxy which is substituted by one or more halogen atoms which may be the same or different, or $C_{1-4}$ alkyl substituted by one or more halogen atoms which may be the same or different, B represents a group selected from the group consisting of a halogen atom, $C_{1-4}$ alkyl, $C_{1-4}$ alkyloxy, and cyano, alternatively adjacent two of $Y_1$, $Y_2$, $Y_3$, $Y_4$, and $Y_5$ may together represent —O—$(CH_2)_n$—O— substituted by one or more halogen atoms, wherein n is 1 or 2.

3. The compound according to claim 1, wherein any one of $W_1$, $W_2$, and $W_3$ represents a nitrogen atom, and the other two groups represent the corresponding C—$Y_1$, C—$Y_2$, or C—$Y_3$, and $Y_1$, $Y_2$, $Y_3$, $Y_4$, and $Y_5$ each independently represent a hydrogen atom; $C_{1-8}$ alkyl substituted by one or more halogen atoms which may be the same or different; or a halogen atom.

4. The compound according to claim 1, wherein $W_1$, $W_2$, and $W_3$ represent C—$Y_1$, C—$Y_2$, and C—$Y_3$, respectively, and $Y_1$, $Y_2$, $Y_3$, $Y_4$, and $Y_5$ each independently represent a hydrogen atom; $C_{1-8}$ alkyl which is substituted by one or more halogen atoms which may be the same or different; $C_{1-8}$ alkyloxy which is substituted by one or more halogen atoms which may be the same or different, and/or $C_{1-4}$ alkyloxy substituted by one or more halogen atoms which may be the same or different; $C_{1-8}$ alkylthio which is substituted by one or more halogen atoms which may be the same or different; or a halogen atom, provided that at least one of $Y_1$, $Y_2$, $Y_3$, $Y_4$, and $Y_5$ represents $C_{1-8}$ alkyl which is substituted by one or more halogen atoms which may be the same or different; $C_{1-8}$ alkyloxy which is substituted by one or more halogen atoms which may be the same or different, and/or $C_{1-4}$ alkyloxy substituted by one or more halogen atoms which may be the same or different; or $C_{1-8}$ alkylthio which is substituted by one or more halogen atoms which may be the same or different, alternatively adjacent two of $Y_1$, $Y_2$, $Y_3$, $Y_4$, and $Y_5$ may together represent $-O-(CH_2)_n-O-$ substituted by one or more halogen atoms, wherein n is 1 or 2.

5. The compound according to claim 1, wherein
$R_1$ represents a hydrogen atom; or $COR_4$ wherein $R_4$ represents $C_{1-4}$ alkyl, $OR_5$ wherein $R_5$ represents $C_{1-4}$ alkyl, or $NR_6R_7$ wherein $R_6$ and $R_7$ each independently represent a hydrogen atom or $C_{1-18}$ alkyl, $R_2$ represents $C_{1-4}$ alkyl, $R_3$ represents $C_{1-4}$ alkyl, alternatively $R_2$ and $R_3$ together represent $-(CH_2)_m-$ wherein m is 3 or 4, $X_1$ and $X_2$ each independently represent a hydrogen atom, a halogen atom, $C_{1-4}$ alkyl optionally substituted by halogen atom, $C_{1-4}$ alkyloxy, or $C_{1-4}$ alkyloxycarbonyl, provided that $X_1$ and $X_2$ do not simultaneously represent a hydrogen atom, $X_3$ represents a hydrogen atom, $W_1$, $W_2$, and $W_3$ represent $C-Y_1$, $C-Y_2$, and $C-Y_3$, respectively, and $Y_1$, $Y_2$, $Y_3$, $Y_4$, and $Y_5$ each independently represent a hydrogen atom; $C_{1-8}$ alkyl which is substituted by one or more halogen atoms which may be the same or different; $C_{1-8}$ alkyloxy which is substituted by one or more halogen atoms which may be the same or different, and/or $C_{1-4}$ alkyloxy substituted by one or more halogen atoms which may be the same or different; $C_{1-8}$ alkylthio which is substituted by one or more halogen atoms which may be the same or different; or a halogen atom, provided that at least one of $Y_1$, $Y_2$, $Y_3$, $Y_4$, and $Y_5$ represents $C_{1-8}$ alkyl which is substituted by one or more halogen atoms which may be the same or different; $C_{1-8}$ alkyloxy which is substituted by one or more halogen atoms which may be the same or different, and/or $C_{1-4}$ alkyloxy substituted by one or more halogen atoms which may be the same or different; or $C_{1-8}$ alkylthio which is substituted by one or more halogen atoms which may be the same or different, alternatively adjacent two of $Y_1$, $Y_2$, $Y_3$, $Y_4$, and $Y_5$ may together represent $-O-(CH_2)_n-O-$ substituted by one or more halogen atoms, wherein n is 1 or 2, and Z represents an oxygen atom, $OCH_2$, or $O(CH_2)_3O$.

6. The compound according to claim 1, wherein
$R_1$ represents $COR_4$ or $COOR_5$ wherein $R_4$ and $R_5$ represent $C_{1-4}$ alkyl, $R_2$ represents $C_{1-4}$ alkyl, $R_3$ represents $C_{1-4}$ alkyl, $X_1$ and $X_2$ each independently represent a hydrogen atom, or $C_{1-4}$ alkyl optionally substituted by halogen atom, provided that $X_1$ and $X_2$ do not simultaneously represent a hydrogen atom, $X_3$ represents a hydrogen atom, $W_1$, $W_2$, and $W_3$ represent $C-Y_1$, $C-Y_2$, and $C-Y_3$, respectively, $Y_1$, $Y_2$, $Y_3$, $Y_4$, and $Y_5$ each independently represent a hydrogen atom; $C_{1-8}$ alkyloxy which is substituted by one or more halogen atoms which may be the same or different, and/or $C_{1-4}$ alkyloxy substituted by one or more halogen atoms which may be the same or different; or a halogen atom, provided that at least one of $Y_1$, $Y_2$, $Y_3$, $Y_4$, and $Y_5$ represents $C_{1-8}$ alkyloxy which is substituted by one or more halogen atoms which may be the same or different, and/or $C_{1-4}$ alkyloxy substituted by one or more halogen atoms which may be the same or different, alternatively adjacent two of $Y_1$, $Y_2$, $Y_3$, $Y_4$, and $Y_5$ may together represent $-O-(CH_2)_n-O-$ substituted by one or more halogen atoms, wherein n is 1 or 2, and Z represents an oxygen atom.

7. An agricultural or horticultural insecticide composition comprising as an active ingredient a compound according to any one of claims 2, 3, and 4 to 6 or an agriculturally and horticulturally acceptable acid addition salt thereof, and a suitable carrier, surfactant, dispersant and/or adjuvant.

8. A method for controlling an agricultural and horticultural insect pest, comprising the step of applying an effective amount of a compound according to any one of claims 2, 3, and 4 to 6 or an agriculturally and horticulturally acceptable acid addition salt thereof to a plant or soil.

9. The method according to claim 8, wherein said insect pest is selected from the group consisting of Lepidoptera, Hemiptera, Coleoptera, Acari, Hymenoptera, Orthoptera, Diptera, Thysanoptera, and plant parasitic nematoda.

* * * * *